US008412460B2

(12) United States Patent
Stoughton et al.

(10) Patent No.: US 8,412,460 B2
(45) Date of Patent: Apr. 2, 2013

(54) METHODS AND SYSTEMS FOR CHARACTERIZING A CELLULAR CONSTITUENT USING RESPONSE PROFILES

(75) Inventors: Roland Stoughton, San Diego, CA (US); Timothy Hughes, Toronto (CA)

(73) Assignee: Microsoft Corporation, Redmond, WA (US)

( * ) Notice: Subject to any disclaimer, the term of this patent is extended or adjusted under 35 U.S.C. 154(b) by 0 days.

(21) Appl. No.: 12/686,311

(22) Filed: Jan. 12, 2010

(65) Prior Publication Data

US 2011/0251081 A1    Oct. 13, 2011

Related U.S. Application Data

(62) Division of application No. 10/332,305, filed as application No. PCT/US01/20928 on Jul. 2, 2001, now Pat. No. 7,657,379.

(60) Provisional application No. 60/215,936, filed on Jul. 5, 2000.

(51) Int. Cl.
| G06F 19/00 | (2011.01) |
| C12Q 1/68 | (2006.01) |
| C12N 15/09 | (2006.01) |
| G06G 7/58 | (2006.01) |

(52) U.S. Cl. ............. 702/19; 702/20; 435/6.1; 435/174; 703/11

(58) Field of Classification Search ........................ None
See application file for complete search history.

(56) References Cited

U.S. PATENT DOCUMENTS

| 4,946,778 | A | 8/1990 | Ladner et al. |
| 5,300,425 | A | 4/1994 | Kauvar |
| 5,510,270 | A | 4/1996 | Fodor et al. |
| 5,539,083 | A | 7/1996 | Cook et al. |
| 5,541,070 | A | 7/1996 | Kauvar |
| 5,556,752 | A | 9/1996 | Lockhart et al. |
| 5,569,588 | A | 10/1996 | Ashby et al. |
| 5,578,832 | A | 11/1996 | Trulson et al. |
| 5,769,074 | A | 6/1998 | Barnhill et al. |
| 5,965,352 | A | 10/1999 | Stoughton et al. |
| 6,028,189 | A | 2/2000 | Blanchard |
| 6,132,969 | A | 10/2000 | Stoughton et al. |
| 6,165,709 | A | 12/2000 | Friend et al. |
| 6,203,987 | B1 | 3/2001 | Friend et al. |
| 6,263,287 | B1 | 7/2001 | Zheng et al. |
| 6,271,002 | B1 | 8/2001 | Linsley et al. |
| 6,324,479 | B1 | 11/2001 | Friend et al. |
| 6,468,476 | B1 | 10/2002 | Friend et al. |
| 6,801,859 | B1 | 10/2004 | Friend et al. |
| 2002/0045197 | A1 | 4/2002 | Friend et al. |
| 2004/0048264 | A1 | 3/2004 | Stoughton et al. |

FOREIGN PATENT DOCUMENTS

| EP | 0534858 A1 | 9/1992 |
| WO | WO 88/09810 | 12/1988 |
| WO | WO 89/12690 | 12/1989 |
| WO | WO 90/11364 | 10/1990 |
| WO | WO 98/38329 | 9/1998 |
| WO | WO 98/41531 | 9/1998 |
| WO | WO 00/24963 | 5/2000 |

OTHER PUBLICATIONS

Heyer et al. (Genome Research (1999) vol. 9, pp. 1106-1115).*
Affymetrix, Inc., "Pioneering an Industry," [date unavailable] visited on Sep. 17, 2008, http://affymetrix.com/support/technical/other/pioneer_brochure.pdf.
Alberts et al., "Mevinolin: A highly potent competitive inhibitor of hydroxymethylglutaryl-coenzyme A reductase and a cholesterol-lowering agent," Proc. Natl. Acad. Sci., 1980, vol. 77, pp. 3957-3961.
Anderson et al., "Involvement of the protein tyrosine kinase p56lck in T cell signaling and thymocyte development," Adv. Immunol, 1994, vol. 56, pp. 171-178.
Anderson "Mutagenesis," Methods Cell Biol., 1995, vol. 48, pp. 31-58.
Bard et al., "Biochemical and genetic aspects of nystatin resistance in *Saccharomyces cerevisiae*," J. Bacteriol., 1972, vol. 111, pp. 649-657.
Baudin et al., "A simple and efficient method for direct gene deletion in *Saccharomyces cerevisiae*," Nucl. Acids Res., 1993, vol. 21, pp. 3329-3330.
Belshaw et al., "Controlling protein association and subcellular localization with a synthetic ligand that includes heterodimerization of proteins," Proc. Natl. Acad. Sci USA, 1996, vol. 93, pp. 4604-4607.
Benoist et al., "In vivo sequence requirements of the SV40 early promoter region," Nature, 1981, vol. 290, pp. 304-310.
Biocca et al., "Intracellular immunization: antibody targeting to subcellular compartments," Trends in Cell Biology, 1995, vol. 5, pp. 248-252.
Blanchard et al., "Sequence to array: probing the genome's secrets," Nature Biotechnology, 1996, vol. 14, p. 1649.
Blanchard et al., "High-density oligonucleotide arrays," Biosensors & Bioelectronics, 1996, vol. 11, pp. 687-690.
Blancard, "Synthectic DNA Arrays in Genetic Engineering," J.K. Setlow, Ed., Plenum Press, New York, 1998, vol. 20, pp. 111-123.
Brazma et al., "One-stop shop for microarray data, Nature, Feb. 17, 2000, vol. 403, pp. 699-700.
Brinster et al., "Regulation of metallothionein-thymidine kinase fusion plasmids injected into mouse eggs," Nature, 1982, vol. 296, pp. 39-42.

(Continued)

*Primary Examiner* — Lori A Clow
(74) *Attorney, Agent, or Firm* — Klarquist Sparkman, LLP

(57) ABSTRACT

The invention relates to methods and systems (e.g., computer systems and computer program products) for characterizing cellular constituents, particularly genes and gene products. In particular, the invention provides methods for assigning or determining the biological function of uncharacterized genes and gene products by using "response profiles," i.e., measurements of pluralities of cellular constituents in cells having a modified gene or gene product, as phenotypic markers for the gene or gene product. Methods are provided for clustering such response profiles so that similar or correlated response profiles are organized into the same cluster. The invention also provides databases or "compendiums" of response profiles to which the response profile of an uncharacterized gene or gene product can compared.

41 Claims, 28 Drawing Sheets

OTHER PUBLICATIONS

Brunel et al., "Mutual information, Fisher information and population coding," Neural Computation, 1998, vol. 10, pp. 1731-1757.

Bryant et al., "Gene Expression and Genetic Networks," Pacific Symposium on Biocomputing, 1998, vol. 3, pp. 3-5.

Burke et al., "Microinjection of mRNA coding for an anti-Golgi antibody inhibits intracellular transport of a viral membrane protein," Cell, 1984, vol. 36, pp. 847-858.

Bussey et al., "The nucleotide sequence of chromosome I from *Saccharomces cerevisiae*," Proc. Natl. Acad. Sci USA, 1995, vol. 92, pp. 3809-3813.

Cardenas et al., "Yeast as model T cells," Perspectives in Drug Discovery and Design, 1994, vol. 2, pp. 103-126.

Carr et al., "Templates for Looking at Gene Expression Clustering," Statistical Computing & Statistical Graphics Newsletter, 1997, vol. 4, pp. 20-29.

Cech, "The Chemistry of self-splicing RNA and RNA enzymes," Science, 1987, vol. 236 pp. 1532-1539.

Chirgwin et al., "Isolation of biologically active ribonucleic acid from sources enriched in ribonuclease," Biochemistry, 1979, vol. 18, pp. 5294-5299.

Chu et al., "The transcriptional program of sporulation in budding yeast," Science, 1998, vol. 282, pp. 699-705.

Cote et al., "Generation of human monoclonal antibodies reactive with cellular antigens," Proc. Natl. Acad. Sci. USA, 1983, vol. 80, pp. 2026-2030.

Cotton et al., "Ribozyme mediated destruction of RNA in vivo," EMBO J., 1989, vol. 8, pp. 3861-3866.

Daum et al., "Biochemistry, cell biology and molecular biology of lipids of *Saccharomyces cerevisiae*," Yeast, 1998, vol. 14, pp. 1471-1510.

DeRisi et al., "Use of a cDNA microarray to analyse gene expression patterns in human cancer," Nature Genetics, 1997, vol. 14, pp. 457-460.

DeRisi et al., "Exploring the metabolic and genetic control of gene expression on a genomic scale," Science, 1997, vol. 278, pp. 680-686.

D'haeseleer et al., "Mining the gene expression matrix: Inferring gene relationships from large scale gene expression data," Information Processing in Cells and Tissues, 1998, pp. 203-212 [online]. http://www.cs.unm.edu/~patrik/networks/IPCAT/ipcat.html.

Dohmen et al., "Heat-inducible degron: a method for constructing temperature-sensitive mutants," Science, 1994, vol. 263, pp. 1273-1276.

Dujon et al., "Complete DNA sequence of yeast chromosome XI," Nature, 1994, vol. 369, pp. 371-378.

Egholm et al., "PNA hybridizes to complementary oligonucleotides obeying the Watson-Crick hydrogen-bonding rules," Nature, 1993, vol. 365, pp. 566-568.

Eide et al., "The vacuolar H(+)-ATPase of *Saccharomyces cerevisiae* is required for efficient copper detoxification mitochondrial function and iron metabolism," Mol. Gen. Genet., 1993, vol. 241, pp. 447-456.

Feldmann et al., "Complete DNA sequence of yeast chromosome II," E.M.B.O. J., 1994, vol. 13, pp. 5795-5809.

Ferguson et al., "A fiber-optic DNA biosensor microarray for the analysis of gene expression," Nature Biotech, 1996, vol. 14, pp. 1681-1684.

Fodor et al., "Light-directed, spatially addressable parallel chemical synthesis," Science, 1991, vol. 251, pp. 767-773.

Froehler et al., "Synthesis of DNA via deoxynucleoside H-phosphonate intermediates," Nucleic Acid Res., 1986, vol. 14, pp. 5399-5407.

Gari et al., "A set of vectors with a tetracycline-regulatable promoter system for modulated gene expression in *Saccharomyces cerevisiae*," Yeast, 1997, vol. 13, pp. 837-848.

Galibert et al., "Complete nucleotide sequence of *Saccharomyces cerevisiae* chromosome X," E.M.B.O. J, 1996, vol. 15, pp. 2031-2049.

Gautier et al., "Alpha-DNA IV: Alpha-anomeric and beta-anometric tetrathymidylates covalently linked to intercalating oxazolopyridocarbazole. Synthesis, physicochemical properties and poly (rA) binding," Nucleic Acids Res, 1987, vol. 15, pp. 6625-6641.

Gibson, "Antisense approaches to the gene therapy of cancer—'Recnac'," Cancer and Metastasis Reviews, 1996, vol. 15, pp. 287-299.

Goffeau et al., "Life with 6000 genes," Science, 1996, vol. 274, pp. 546-567.

Golub et al., "Molecular classification of cancer: class discovery and class prediction by gene expression monitoring," Science, 1999, vol. 286, pp. 531-537.

Good et al., "Expression of small, therapeutic RNAs in human cell nuclei," Gene Therapy, 1997, vol. 4, pp. 45-54.

Gossen et al., "Tight control of gene expression in mammalian cells by tetracycline-responsive promoters," Proc. Nat. Acad. Sci. USA, 1992, vol. 89, pp. 5547-5551.

Grassi et al., "Ribozymes: structure, function, and potential therapy for dominant genetic disorders," Annals of Medicine, 1996, vol. 28, pp. 499-510.

Gray et al., "Exploiting chemical libraries, structure, and genomics in the search for kinase inhibitors," Science, 1998, vol. 281, pp. 533-538.

Griffiths et al., "Isolation of high affinity human antibodies directly from large synthetic repertoires," EMBO J, 1994, vol. 13, pp. 3245-3260.

Hanner et al., "Prification, molecular cloning, and expression of the mammalian sigma 1-binding site," Proc. Natl. Acad. Sci. USA, 1996, vol. 93, pp. 8072-8077.

Hanke JH, "Discovery of a novel potent and Src family-selective tyrosine kinase inhibitor. Study of Lck- and FynT-dependent T cell activation," J. Biol. Chem, 1996, vol. 271, pp. 695-701.

Haseloff et al., "Simple RNA enzymes with new and highly specific endoribonuclease activities," Nature, 1988, vol. 334, pp. 585-591.

Hayden et al., "Antibody engineering," Current opinion in immunology, 1997, vol. 9, pp. 210-212.

Hershkowitz, "Functional inactivation of genes by dominant negative mutations," Nature,, 1987, vol. 329, pp. 219-222.

Hoffmann et al., "A novel tetracycline-dependent expression vector with low basal expression and potent regulatory properties in various mammalian cell lines," Nucl. Acids. Res., 1997, vol. 25, pp. 1078-1079.

Hoffmann et al. "Rapid retroviral delivery of tetracycline-inducible genes in a single autoregulatory cassette," Proc. Natl. Acad. Sci, USA, 1996, vol. 93, pp. 5185-5190.

Holstege et al., "Dissecting the regulatory circuitry of a eukaryotic genome," Cell, 1998, vol. 95, pp. 717-728.

Huse et al., "Generation of a large combinatorial library of the immunoglobulin repertoire in phage lambda," Science, 1989, vol. 246, pp. 1275-1281.

Inoue et al., "Synthesis and hybridizations studies on two complementary nona(2'-O-methyl)ribonucleotides," Nucleic Acids Res., 1987, vol. 15, pp. 6131-6148.

Inoue et al., "Sequence-dependent hydrolysis of RNA using modified oligonucleotide splints and RNase H," FEBS Lett, 1987, vol. 215, pp. 327-330.

Jasney, BR, "The Universe of Drosophila Genes," Science, 2000, vol. 287, p. 2181.

Johnston et al. "Complete nucleotide sequence of *Saccharomyces cerevisiae* chromosome VIII," Science, 1994, vol. 265, pp. 2077-2082.

Johnston et al., "Sequences that regulate the divergent GAL1-GAL10 promoter in *Saccharomyces cerevisiae*," Mol. Cell. Boil., 1984, vol. 8, pp. 1440-1448.

Jungmann et al., "CAM1, a nuclear regulatory protein related to Cu-dependent transcription factors is involved in Cu/Fe utilization and stress resistance in yeast," EMBO J., 1993, vol. 12, pp. 5051-5056.

Kekuda et al., "Cloning and functional expression of the human type 1 sigma receptor (hSigmaR1)," Biochem. Biophys. Res. Commun, 1996, vol. 229, pp. 553-558.

Kleher et al., "Ssn6-Tup1 is a general repressor of transcription in yeast," Cell, 1992, vol. 68, pp. 709-719.

Kerjan et al., "Nucleotide sequence of the *Saccharomyces cerevisiae* MET25 gene," Nucl. Acids. Res., 1986, vol. 14, pp. 7861-7871.

Kohler et al., "Continuous cultures of fused cells secreting antibody of predefined specificity," Nature, 1975, vol. 256, pp. 495-497.

Koizumi et al., "Construction of a series of several self-cleaving RNA duplexes using synthetic 21-mers," FEBS Lett., 1988, vol. 228, pp. 228-230.

Koizumi et al., "Cleavage of specific sites of RNA by designed ribozymes," FEBS Lett., 1988, vol. 239, pp. 285-288.

Kozbor et al., "The production of monoclonal antibodies from human lymphocytes," Immunol Today, 1983, vol. 4, pp. 72-79.

Lander, "The new genomics: global views of biology," Science, 1996, vol. 274, pp. 536-539.

Lemaitre et al., "Specific antiviral activity of a poly(L-lysine)-conjugated loigodeoxyribonucleotide sequence complementary to vesicular stomatitis virus N protein mRNA initiation site," Proc. Natl. Acad. Sci. USA, 1987, vol. 84, pp. 648-652.

Letsinger et al., "Cholesteryl-conjugated oligonucleotides: synthesis, properties, and activity as inhibitors of replication of human immunodeficiency virus in cell culture," Proc. Natl. Acad. Sci. USA, 1989, vol. 86, pp. 6553-6556.

Lin et al., "Antiproliferative Effects of Oxygenated Sterols: Positive Correlation with Binding Affinities for the Anti-estrogen Binding Site," Biochimica et Biophysica Acta., 1991, vol. 1082, pp. 177-184.

Link et al., "Direct analysis of protein complexes using mass spectrometry," Nat. Biotechnol. 1999, vol. 17, pp. 676-682.

Lipke et al., "Morphogenic effects of a factor on *Saccharomyces cerevisiae* a cells," J. Bacteriol., 1976, vol. 127, pp. 610-618.

Lockhart et al., "Expression monitoring by hybridization to high-density oligonucleotide arrays," Nature Biotechnology, 1996, vol. 14, pp. 1675-1680.

Lussier et al., "Large scale identification of genes involved in cell surface biosynthesis and architecture in *Saccharomyces cerevisiae*," Genetics, 1997, vol. 147, pp. 435-450.

Marks et al., "Molecular evolution of proteins on filamentous phage. Mimicking the strategy of the immune system," J. Biol. Chem., 1992, vol. 267, pp. 16007-16010.

Marton et al., "Drug target validation and identification of secondary drug target effects using DNA microarrays," Nat. med., 1998, vol. 4, pp. 1293-1301.

Mascorro-Gallardo et al., "Construction of a CUP1 promoter-based vector to modulate gene expression in *Saccharomyces cerevisiae*," Gene, 1996, vol. 172, pp. 169-170.

Maskos et al., "Oligonucleotide hybridiazations on glass supports: a novel linker for oligonucleotide synthesis and hybridization properties of oligonucleotides synthesized in situ," Nucl. Acids Res., 1992, vol. 20, pp. 1679-1684.

McBride et al., "An investigation of several deoxynucleoside phosphoramidites useful for synthesizing deoxyoligonucleotides," Tetrahedron Lett., 1983, vol. 24, pp. 246-248.

Mewes et al., "MIPS: a database for protein sequences, homology data and yeast genome information," Nucl. Acids Res., 1997, vol. 25, pp. 28-30.

Michaels et al., "Cluster analysis and data visualization of large-scale gene expression data," Pac. Symp Biocomput, 1998, pp. 42-53.

Moebius et al., "Yeast sterol C8-C7 isomerase: identification and characterization of a high-affinity binding site for enzyme inhibitors," Biochemistry, 1996, vol. 35, pp. 16871-16878.

Moebius et al., "High affinity of signal-binding sites for sterol isomerization inhibitors: evidence for a pharmacological relationship with the yeast sterol C8-C7 isomerase," Br. J. Pharmacol., 1997, vol. 121, pp. 1-6.

Molzahn et al., "Polyene resistance and the isolation of sterol mutants in *Saccharomyces cerevisiae*," J. Gen. Microbiol., 1972, vol. 72, pp. 339-348.

Morgan et al., "Analysis of intracellular protein function by antibody injection," Immunology Today, 1988, vol. 9, pp. 84-86.

Morrison et al., "Chimeric human antibody molecules: mouse antigen-binding domains with human constant region domains," Proc. Natl. Acad. Sci. USA, 1984, vol. 81, pp. 6851-6855.

Mumberg et al., "Regulatable promoters of *Saccharomyces cerevisiae*: comparison of transcriptional activity and their use for heterologous expression," Nucl. Acids. Res., 1994, vol. 22, pp. 5767-5768.

Nakajima et al., "FR901228, a potent antitumor antibiotic, is a novel histone deacetylase inhibitor," Exp. Cell. Res., 1998, vol. 241, pp. 126-133.

Nelson et al., "A bovine cDNA and a yeast gene (VMA8) encoding the subunit D of the vacuolar H(+)-ATPase," Proc. Natl. Acad. Sci. USA, 1995, vol. 92, pp. 497-501.

Neuberger et al., "Recombinant antibodies possessing novel effector functions," Nature, 1984, vol. 312, pp. 604-608.

Nguyen et al., "Differential Gene Expression in the Murine Thymus Assayed by Quantitative Hybridization of Arrayed cDNA clones," Geonomics, 1995, vol. 29, pp. 207-216.

Nguyen et al., "σ-Binding site ligands inhibit K+ currents in rat locus coeruleus neurons in vitro," Eur. J. Pharmacol., 1998, vol. 361, pp. 157-163.

No et al., "Ecdysone-inducible gene expression in mammalian cells and transgenic mice," Proc. Natl. Acad. Sci. USA, 1996, vol. 93, pp. 3346-3351.

Nocka et al., "Molecular bases of dominant negative and loss of function mutations at the murine c-kit/white spotting locus: W37, Wv, W41 and W," EMBO J., 1990, vol. 9, pp. 1805-1813.

Ohya et al., "Calcium-sensitive cls mutants of *Saccharomyces cerevisiae* showing a pet-phenotype are ascribable to defects of vacuolar membrane H+-AtPase activity," J. Biol. Chem., 1991, vol. 266, pp. 13971-13977.

Okada et al., "Syntergistic Activation of PtdIns 3-Kinase by Tyrosine-phosphorylated Peptide and beta gamma subunits of GTP-binding Proteins," Biochemical Journal, 1996, vol. 317, pp. 475-480.

Ovalle et al., "A spheroplast rate assay for determination of cell wall integrity in yeast," Yeast, 1998, vol. 14, pp. 1159-1166.

Parks et al., "Biochemical and physiological effects of sterol alterations in yeast—a review," Lipids, 1995, vol. 30, pp. 227-230.

Paulus et al., "Self-Contained, Tetracycline-Regulated Retroviral Vector System for Gene Delivery to Mammalian Cells," Journal of Virology, 1996, vol. 70, pp. 62-67.

Pease et al., "Light-generated oligonucleotide arrays for rapid DNA sequence analysis," Proc. Natl. Acad. Sci. USA, 1994, vol. 91, pp. 5022-5026.

Perlmutter et al., "The use of dominant-negative mutations to elucidate signal transduction pathways in lymphocytes," Current Opinion in Immunology, 1996, vol. 8, pp. 285-290.

Perou et al., "Distinctive gene expression patterns in human mammary epithelial cells and breast cancers," Proc. Nat. Acad. Sci. USA, 1999, vol. 96, pp. 9212-9217.

Pettitt et al., "cdh-3, a gene encoding a member of the cadherin superfamily, functions in epithelial call morphogenesis in *Caenorhabditis elegans*," Development, 1996, vol. 122, pp. 4149-4157.

Prashar et al., "Analysis of differential gene expression by display of 3' end restriction fragments of cDNAs," Proc. Natl. Acad. Sci. USA, 1996, vol. 93, pp. 659-663.

Press et al., "Minimization or maximization of functions," Cambridge University Press, Numerical Recipes in C $2^{nd}$ Ed., 1996, pp. 290-352.

Press et al., "Modeling of Data," Cambridge University Press, Numerical Recipes in C $2^{nd}$ Ed., 1996, pp. 517-565.

Raguzzi et al., "Iron storage in *Saccharomyces cerevisiae*," FEBS Lett., 1988, vol. 231, pp. 253-258.

Ram et al., "A new approach for isolating cell wall mutants in *Saccharomyces cerevisiae* by screening for hypersensitivity to calcofluor white," Yeast, 1994, vol. 10, pp. 1019-1030.

Ramirez-Solis et al., "Gene targeting in embryonic stem cells," Methods Enzymol, 1993, vol. 225, pp. 855-878.

Roberts et al., "Signaling and circuitry of multiple MAPK pathways revealed by a matrix of global gene expression profiles," Science, 2000, vol. 287, pp. 873-880.

Roncero et al., "Isolation and characterization of *Saccharomyces cerevisiae* mutants resistant to Calcofluor white," J. Bacteriol., 1988, vol. 170, pp. 1950-1954.

Sagliocco et al., "Identification of proteins of the yeast protein map using genetically manipulated strains and peptide-mass fingerprinting," Yeast, 1996, vol. 12, pp. 1519-1533.

Sarin et al., "Inhibition of acquired immunodeficiency syndrome virus by oligodeoxynucleoside methylphhosphonates," Proc. Natl. Acad. Sci. USA, 1988, vol. 85, pp. 7448-7451.

Sarver et al., "Ribozymes as potential anti-HIV-1 therapeutic agents," Science, 1990, vol. 247, pp. 1222-1225.

Schena et al., "Parallel human genome analysis: microarray-based expression monitoring of 1000 genes," Proc. Natl. Acad. Sci. USA, 1995, vol. 93, pp. 10614-10619.

Schena et al., "quantitative monitoring of gene expression patterns with a complementary DNA microarray," Science, 1995, vol. 270, pp. 467-470.

Shalon et al., "A DNA microarray system for analyzing complex DNA samples using two-color fluorescent probe hybridization," Genome Res., 1996, vol. 6, pp. 639-645.

Shevchenko et al., Linking genome and proteome by mass spectrometry: large-scale identification of yeast proteins from two dimensional gels,: Proc. Natl. Acad. Sci. USA, 1996, vol. 93, pp. 1440-1445.

Shoemaker et al., "Quantitative phenotypic analysis of yeast deletion mutants using a highly parallel molecular bar-coding strategy," Nature Genetics, 1996, vol. 14, pp. 450-456.

Smith et al., "Functional analysis of the genes of yeast chromosome V by genetic footprinting," Science, 1996, vol. 274, pp. 2069-2074.

Spellman, "Comprehensive Identification of Cell Cycle-regulated Genes of the Yeast *Saccharomyces cerevisiae* by Microarray Hybridization," Mol. Biol. Of the Cell, Dec. 1998, vol. 9, pp. 3273-3297.

Spencer, "Creating conditional mutations in mammals," Trends Genet, 1996, vol. 12, pp. 181-187.

Spradling et al., "Gene disruptions using P transposable elements: an integral component of the Drosophila genome project," Proc. Natl. Acad. Sci. USA, 1995, vol. 92, pp. 10824-10830.

Stein et al., "Physicochemical properties of phosphorothioate oligodeoxynucleotides," Nucleic Acids Res., 1988, vol. 16, pp. 3209-3221.

Stormo et al., "Identifying protein-binding sites from unaligned DNA fragments," Proc. Natl. Acad. Sci, 1989, vol. 86, pp. 1183-1187.

Straus et al., "Genetic evidence for the involvement of the lck tyrosine kinase in signal transduction through the T cell antigen receptor," Cell, 1992, vol. 70, pp. 585-593.

Szczypka et al., "*Saccharomyces cerevisiae* mutants altered in vacuole function are defective in copper detoxification and iron-responsive gene transcription," Yeast, 1997, vol. 13, pp. 1423-1435.

Takeda et al., "Construction of chimaeric processed immunoglobulin genes containing mouse variable and human constant region sequences," Nature, 1985, vol. 314, pp. 452-454.

Thomas et al., "Site-directed mutagenesis by gene targeting in mouse embryo-derived stem cells," Cell, 1987, vol. 51, pp. 503-512.

Veitia et al., "A novel human gene, encoding a potential membrane protein conserved from yeast to man, is strongly expressed in testis and cancer cell lines," Cytogenet Cell Genet., 1999, vol. 85, pp. 217-220.

Van der Krol et al., "Modulation of Eukaryotic Gene Expression by Complementary RNA or DNA Sequences," BioTechniques, 1988, vol. 6, pp. 958-976.

Velculescu et al., "Serial analysis of gene expression," Science, 1995, vol. 270, pp. 484-548.

Wach et al., "New heterologous modules for classical or PCR-based gene disruptions in *Saccharomyces cerevisiae*," Yeast, 1994, vol. 10, pp. 1793-1808.

Wagner et al., "Nucleotide sequence of the thymidine kinase gene of herpes simplex virus type 1," Proc. Natl. Acad. Sci. USA, 1981, vol. 78, pp. 1441-1445.

Ward, "Hierarchial grouping to optimize an objective function," J. Am. Stat. Assn., 1963, vol. 58, pp. 236-244.

Wen et al., "Large-scale temporal gene expression mapping of central nervous system development," Proc. Natl. Acad. Sci. USA, 1998, vol. 95, pp. 334-339.

Wilke et al., "K+ channel modulation in rodent neurohypophysial nerve terminals by sigma receptors and not by dopamine receptors," J. Physiol. (Lond.), 1999, vol. 517, pp. 391-406.

Williams et al., "The CYC8 and TUP1 proteins involved in glucose repression in *Saccharomyces cerevisiae* are associated in a protein complex," Mol. Cell. Boil., 1991, vol. 11, pp. 3307-3316.

Winzeler et al., "Functional characterization of the *S. cerevisiae* genome by gene deletion and parallel analysis," Science, 1999, vol. 285, pp. 901-906.

Wittes et al., "Searching for evidence of altered gene expression: a comment on statistical analysis of microarray data," J. Natl. Cancer Inst., 1999, vol. 91, pp. 400-401.

Yamamoto et al., "Identification of a functional promoter in the long terminal repeat of Rous sarcoma virus," Cell, 1980, vol. 22, pp. 787-797.

Zhang et al., "Gene Expression Profiles in Normal and Cancer Cells," Science, 1997, vol. 276, pp. 1268-1272.

Zhou et al., "Isolation of crt Mutants Constitutive for transcription of the DNA damanage inducible gene RNR3 in *Saccharomyces cerevisiae*," Genetics, 1992, vol. 131, pp. 851-866.

Zon, "Oligonucleotide analogues as potential chemotherapeutic agents," Pharm Res., 1988, vol. 5, pp. 539-549.

* cited by examiner by experiments

METHODS AND SYSTEMS FOR CHARACTERIZING A CELLULAR CONSTITUENT USING RESPONSE PROFILES

This application is a divisional of U.S. patent application Ser. No. 10/332,305, filed Sep. 24, 2003, which is a 371 of PCT/US01/20928, filed Jul. 2, 2001, and claims the benefit of provisional U.S. Patent Application No. 60/215,936 filed Jul. 5, 2000, all of which are incorporated by reference herein in their entirety.

1. FIELD OF THE INVENTION

The present invention relates to methods for characterizing genes and their gene products. In particular, the invention relates to methods for assigning or determining biological functions of uncharacterized genes and gene products using biological expression patterns. The invention also relates to methods for analyzing biological expression patterns to assign or determine biological functions for individual cellular constituents (e.g., for individual genes or their gene products).

2. BACKGROUND OF THE INVENTION

Within the past decade, several technologies have made it possible to monitor the expression level of large numbers of transcripts at any one time (see, e.g., Schena et al., 1995, *Science* 270:467-470; Lockhart et al., 1996, *Nature Biotechnology* 14:1675-1680; Blanchard et al., 1996, *Nature Biotechnology* 14:1649; Ashby et al., U.S. Pat. No. 5,569,588, issued Oct. 29, 1996). In organisms for which the complete genome is known, it is possible to analyze the transcripts for all genes within the cell. Even with other organisms, including mammalian organisms such as humans, for which there is an increasing knowledge of the genome, it is possible to simultaneously monitor large numbers of the genes with a cell.

Such monitoring technologies have been applied, for example, to identify genes that are up-regulated or down-regulated in various diseased or physiological states, and to analyze members of signaling cellular states, and to identify targets for various drugs. See, e.g., Friend and Hartwell, U.S. Provisional Patent Application Ser. No. 60/039,134, filed on Feb. 28, 1997; Stoughton, U.S. patent application Ser. No. 09/099,722, filed on Jun. 19, 1998; Stoughton and Friend, U.S. patent application Ser. No. 09/074,983, filed on filed on May 8, 1998; Friend and Hartwell, U.S. Provisional Application Ser. No. 60/056,109, filed on Aug. 20, 1997; Friend and Hartwell, U.S. application Ser. No. 09/031,216, filed on Feb. 26, 1998; Friend and Stoughton, U.S. Provisional Application Ser. No. 60/084,742 (filed on May 8, 1998), 60/090,004 (filed on Jun. 19, 1998) and 60/090,046 (filed on Jun. 19, 1998).

Other methods have been described in the art for analyzing the large numbers of biological responses that can be measured using current array technology. In particular, methods are known in the art for "clustering" cellular constituents, such as gene transcripts (i.e., mRNAs) and gene products, according to their response to different "perturbations" (see, for example, Michaels et al., 1998, *Pac. Symp. Biocomput.*: 42-53; Wen et al., 1998, *Proc. Natl. Acad. Sci. U.S.A.* 95:334-339; DeRisi et al., 1997, *Science* 278:680-686; Bryant et al., 1998, *Pacific Symposium on Biocomputing* 3:3-5; Carr et al., 1997, *Statistical Computing & Statistical Graphics Newsletter* pp. 20-29; D'haeseleer et al., 1998, "Mining the Gene Expression Matrix: Inferring Gene Relationships From Large Scale Gene Expression Data".

Such analytical techniques include, for example, "clustering" cellular constituents according to the similarity of their responses to different perturbations, as well as clustering perturbations (e.g., genetic mutations, drug treatments, etc.) that similarly affect different cellular constituents, and/or two-dimensional clustering of both cellular constituents and perturbations (see, for example, U.S. patent application Ser. Nos. 09/179,569, 09/220,142, 09/220,275 and 09/428,427; filed on Oct. 27, 1998, Dec. 23, 1998, Dec. 23, 1998 and Oct. 27, 1999, respectively, and PCT International Publication WO 00/24936 published May 4, 2000).

To date, most expression profiling studies have focused on particular genes that respond to certain conditions or treatments of interest. For example, Chu et al. (1998, *Science* 282:699-705) have shown that several previously uncharacterized genes that are induced upon yeast sporulation are required for completion of the sporulation program. However, the idea that the global transcription response itself can be used to characterize cells has also received attention (see, for example, DeRisi et al., 1997 *Science* 278:680-686; Gray et al., 1998 *Science* 281:533-538; Holstege et al., 1998, *Cell* 95:717-728; Marton et al., 1998, *Nat. Med.* 4:1293-1301; Roberts et al., 2000, *Science* 287:873-880). For example, tumors have been classified by their expression profiles (Perou et al., 1999, *Proc. Natl. Acad. Sci. U.S.A.* 96:9212-9217; Golub et al., 1999, *Science* 286:531-537; Alizadeh et al., 2000, *Nature* 403:503-511).

There remain many genes that have been fully sequenced, but that have not been fully characterized and for which there is no known biological function. For example, although the genome of the yeast *Saccharomyces cerevisiae* has been fully sequenced, of the 6275 open reading frames (ORFs) identified in that organism's genome, approximately one-third have no known biological function. In higher organisms, the fraction of genes with unknown biological function is much higher.

As ongoing sequencing efforts such as the human genome project near completion and whole genome sequences for many organisms become known, there is an increasing need for high throughput methods for determining biological functions for such uncharacterized genes. Further, there remain methods for more robust high throughput data analysis techniques, particularly robust methods for clustering expression profiles, that can be used in such high throughput analytical methods. The methods and compositions of the present invention therefore solve these and other problems in the prior art.

Discussion or citation of a reference herein shall not be construed as an admission that such reference is prior art to the present invention.

3. SUMMARY OF THE INVENTION

The present invention provides methods for characterizing particular cellular constituents of a cell or organism, including methods for characterizing genes and gene products of a cell or organism. In particular, the invention provides improved, robust methods for detecting structures in the response of biological systems to various perturbations such as the response to a drug, a drug candidate or an experimental condition that probes one or more biological pathways. The various perturbations can also include changes in biological systems that correspond to a particular disease or disease state or to treatment of a particular disease or disease state.

The inventors have discovered that expression profiles can be used as indicators or markers of phenotype. Thus, novel mutants can be systematically characterized using a single genome-wide expression measurement. The invention is also partially premised upon the surprising discovery that mutants of a cell or organism can be systematically characterized using a database or "compendium" of perturbation profiles. In particular, the biological function or pathway perturbed by an uncharacterized mutation can be readily ascertained by using the methods of the present invention to determine which expression profiles in such a database most closely resemble the expression profile of the uncharacterized mutation.

The inventors have also discovered that perturbations to a cell or organism caused, e.g., by a disease states or pharmaceutical treatments, cause changes in transcription profiles that are substantially identical to changes which occur for genetic mutations. Thus, the methods and compositions of the present invention can be used, not only to characterize biological pathways or functions associated with genetic mutations, but also to identify biological pathways and/or functions that are targeted by particular diseases or by particular pharmaceutical (i.e., drug) treatments.

In a first embodiment, the present invention relates to a method for characterizing a cellular constituent as being associated or not being associated with a biological function, said method comprises identifying one or more response profiles associated with a known biological function as either correlating or not correlating with a response profile for the cellular constituent being characterized, wherein: (a) each of said one or more response profiles associated with said known biological function comprises changes of a plurality of cellular constituents in a biological sample in which a particular cellular constituent, other than the cellular constituent being characterized, that is associated with said known biological function is perturbed, (b) said response profile for the cellular constituent being characterized comprises changes of measured amounts of a plurality cellular constituents in a biological sample in which the cellular constituent being characterized is perturbed, and (c) either the cellular constituent being characterized is characterized as being associated with said known biological function if said response profile for said cellular constituent being characterized correlates with said response profile associated with said known biological function, or the cellular constituent being characterized is characterized as not being associated with said known biological function if said response profile for said cellular constituent being characterized does not correlate with said response profile associated with said known biological function.

In a second embodiment, the present invention relates to a method for characterizing a cellular constituent as being associated or not associated with a particular biological function, in which said method comprises: (a) clustering a plurality of response profiles, wherein each response profile in said plurality of response profiles comprises changes in measured amounts of a plurality of cellular constituents in a biological sample in which a particular cellular constituent is perturbed or modified, and said plurality of response profiles includes a response profile for the cellular constituent being characterized, said response profile for the cellular constituent being characterized comprising changes in measured amounts of a plurality of cellular constituents expressed in a biological sample in which the cellular constituent being characterized is perturbed or modified; and (b) identifying one or more response profiles in said plurality of response profiles that cluster with the response profiles for the cellular constituent being characterized, said identified response profiles being associated with a known biological function, or identifying one or more response profiles in said plurality of response profiles that do not cluster with the response profiles for the cellular constituent being characterized, said identified response profiles being associated with a known biological function, wherein if said response profile associated with the cellular constituent being characterized is identified as clustering with said response profiles being associated with a known biological function, said cellular constituent is characterized as being associated with said known biological function, and if said response profile associated with the cellular constituent being characterized is identified as not clustering with said response profiles being associated with a known biological function, said cellular constituent is characterized as not being associated with said known biological function.

In a third embodiment, the present invention relates to a computer system for characterizing cellular constituents, said computer system comprising: one or more processor units; and one or more memory units connected to said one or more processor units, said one or more memory units containing one or more programs which cause said one or more processor units to execute steps of: (a) receiving a data structure for a response profile of a cellular constituent to be characterized, said response profile of a cellular constituent to be characterized comprising changes of measured amounts of a plurality of cellular constituents in a biological sample in which the cellular constituent to be characterized is perturbed; and (b) identifying one or more response profiles associated with a known biological function that correlate or do not correlate with said response profile of the cellular constituent to be characterized, wherein each of the one or more response profiles associated with said known biological function comprises changes of a plurality of cellular constituents in a biological sample in which a particular cellular constituent, other than the cellular constituent to be characterized, that is associated with said known biological function is perturbed, wherein if said response profile of the cellular constituent to be characterized correlates with said one or more response profiles associated with a known biological function, the cellular constituent to be characterized is characterized as being associated with said known biological function, and if said response profile of the cellular constituent to be characterized does not correlate with said one or more response profiles associated with a known biological function, the cellular constituent to be characterized is characterized as not being associated with said known biological function.

In a fourth embodiment, the present invention relates to a computer program product for use in conjunction with a computer having one or more memory units and one or more processor units, the computer program product comprising a computer readable storage medium having a computer program mechanism encoded thereon, wherein said computer program mechanism can be loaded into the one or more memory units of a computer and cause the one or more processor units of the computer to execute steps of: (a) receiving a data structure for a response profile of a cellular constituent to be characterized, said response profile of a cellular constituent to be characterized comprising changes of measured amounts of a plurality of cellular constituents in a biological sample in which the cellular constituent to be characterized is perturbed; and (b) identifying one or more response profiles associated with a known biological function that correlate with said response profile of the cellular constituent to be characterized, wherein each of the one or more response profiles associated with said known biological function comprises changes of a plurality of cellular constituents in a biological sample in which a particular cellular constituent, other than the cellular constituent to be characterized, that is associated with said known biological function is perturbed.

In a fifth embodiment, the present invention relates to a method for determining a biological function with which a cellular constituent of a cell type or organism is associated, comprising: (a) determining measured amounts of a plurality of cellular constituents in a first cell of said cell type or of said organism in which said cellular constituent has been perturbed to create a first response profile; (b) comparing said first response profile, or a predicted response profile derived therefrom, to a database comprising a plurality of landmark response profiles to determine the one or more landmark response profiles most similar to said first or predicted response profile, each landmark response profile comprising measured amounts of a plurality of cellular constituents in a second cell of said cell type or type of organism having a perturbation in a cellular constituent associated with a known biological function, wherein the known biological function of the cellular constituent perturbed in the one or more landmark response profiles determined in step (b) is the biological function with which said cellular constituent is associated.

In a sixth embodiment, the present invention relates to a method for determining a biological function with which a cellular constituent of a cell type or organism is associated, comprising comparing a first response profile or a predicted response profile derived therefrom to a database comprising a plurality of landmark response profiles to determine the one or more landmark response profiles most similar to said first or predicted response profile; wherein said first response profile comprises measured amounts of a plurality of cellular constituents in a first cell of said cell type or of said organism in which said cellular constituent has been perturbed; wherein each landmark response profile comprises measured amounts of a plurality of cellular constituents in a second cell of said cell type or type of organism having a perturbation to a cellular constituent associated with a known biological function; and wherein the known biological function of the cellular constituent perturbed in the one or more landmark response profiles determined to be most similar is the biological function with which said cellular constituent is associated.

In a seventh embodiment, the present invention relates to a method for characterizing a cellular constituent as being associated with a particular biological function, comprising: (a) determining measured amounts of a plurality of cellular constituents in a first cell of a cell type or organism in which said cellular constituent being characterized is perturbed or modified to create a first response profile; (b) clustering a plurality of response profiles, which comprise said first response profile and a plurality of landmark response profiles, each landmark response profile comprising measured amounts of a plurality of cellular constituents in a second cell of said cell type or type of organism having a perturbation or modification in a cellular constituent associated with a known biological function; and (c) identifying one or more landmark response profiles in said plurality of landmark response profiles that cluster with the first response profile for the cellular constituent being characterized, said identified landmark response profiles being associated with a known biological function, wherein the cellular constituent being characterized is characterized as being associated with said known biological function.

In an eighth embodiment, the present invention relates to a method for characterizing a cellular constituent as being associated with a particular biological function, comprising: (a) clustering a plurality of response profiles, which comprise: (i) a first response profile comprising measured amounts of a plurality of cellular constituents in a first cell of a cell type or organism in which said cellular constituent being characterized is perturbed or modified; and (ii) a plurality of landmark response profiles, each landmark response profile comprising measured amounts of a plurality of cellular constituents in a second cell of said cell type or type of organism having a perturbation or modification in a cellular constituent associated with a known biological function; and (c) identifying one or more landmark response profiles in said plurality of landmark response profiles that cluster with the first response profile for the cellular constituent being characterized, said identified landmark response profiles being associated with a known biological function, wherein the cellular constituent being characterized is characterized as being associated with said known biological function.

In a ninth embodiment, the present invention relates to a computer system for identifying a biological function with which a cellular constituent is associated, said computer system comprising: one or more processor units; and one or more memory units connected to said one or more processor units, said one or more memory units containing one or more programs which cause said one or more processor units to execute steps of: (a) receiving a data structure for a first response profile comprising measured amounts of a plurality of cellular constituents in a first cell of said cell type or of said organism in which said cellular constituent has been perturbed; and (b) comparing said first response profile, or a predicted response profile derived therefrom, to a database comprising a plurality of landmark response profiles to determine the one or more landmark response profiles most similar to said first or predicted response profile, each landmark response profile comprising measured amounts of a plurality of cellular constituents in a second cell of said cell type or type of organism having a perturbation in a cellular constituent associated with a known biological function, wherein the known biological function of the cellular constituent perturbed in the one or more landmark response profiles determined in step (b) is the biological function with which said cellular constituent is associated.

In a tenth embodiment, the present invention relates to a computer system for identifying a biological function with which a cellular constituent is associated, said computer system comprising: one or more processor units; and one or more memory units connected to said one or more processor units, said one or more memory units containing one or more programs which cause said one or more processor units to execute steps of comparing a first response profile or a predicted response profile derived therefrom to a database comprising a plurality of landmark response profiles to determine the one or more landmark response profiles most similar to said first or predicted response profile; wherein said first response profile comprises measured amounts of a plurality of cellular constituents in a first cell of said cell type or of said organism in which said cellular constituent has been perturbed; wherein each landmark response profile comprises measured amounts of a plurality of cellular constituents in a second cell of said cell type or type of organism having a perturbation to a cellular constituent associated with a known biological function; and wherein the known biological function of the cellular constituent perturbed in the one or more landmark response profiles determined to be most similar is the biological function with which said cellular constituent is associated.

In an eleventh embodiment, the present invention relates to a computer program product for use in conjunction with a computer having one or more memory units and one or more processor units, the computer program product comprising a computer readable storage medium having a computer program mechanism encoded thereon, wherein said computer program mechanism can be loaded into the one or more memory units of a computer and cause the one or more processor units of the computer to execute steps of: (a) receiving a data structure for a first response profile comprising measured amounts of a plurality of cellular constituents in a first cell of said cell type or of said organism in which said cellular constituent has been perturbed; and (b) comparing said first response profile, or a predicted response profile derived therefrom, to a database comprising a plurality of landmark response profiles to determine the one or more landmark response profiles most similar to said first or predicted response profile, each landmark response profile comprising measured amounts of a plurality of cellular constituents in a second cell of said cell type or type of organism having a perturbation in a cellular constituent associated with a known biological function, wherein the known biological function of the cellular constituent perturbed in the one or more landmark response profiles determined in step (b) is the biological function with which said cellular constituent is associated.

In a twelfth embodiment, the present invention relates to a computer program product for use in conjunction with a computer having one or more memory units and one or more processor units, the computer program product comprising a computer readable storage medium having a computer program mechanism encoded thereon, wherein said computer program mechanism can be loaded into the one or more memory units of a computer and cause the one or more processor units of the computer to execute steps of: comparing a first response profile or a predicted response profile derived therefrom to a database comprising a plurality of landmark profiles to determine the one or more landmark response profiles most similar to said first or predicted response profile; wherein said first response profile comprises measured amounts of a plurality of cellular constituents in a first cell of said cell type or of said organism in which said cellular constituent has been perturbed; wherein each landmark response profile comprises measured amounts of a plurality of cellular constituents in a second cell of said cell type or type of organism having a perturbation to a cellular constituent associated with a known biological function; and wherein the known biological function of the cellular constituent perturbed in the one or more landmark response profiles determined to be most similar is the biological function with which said cellular constituent is associated.

4. BRIEF DESCRIPTION OF THE FIGURES

Figure 5A:
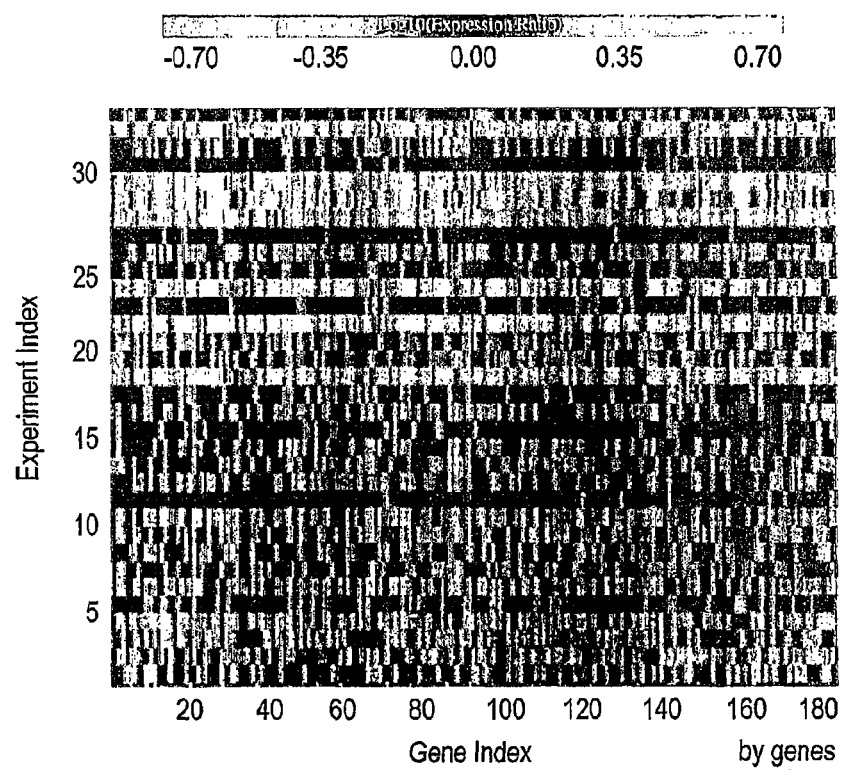
Figure 5B:
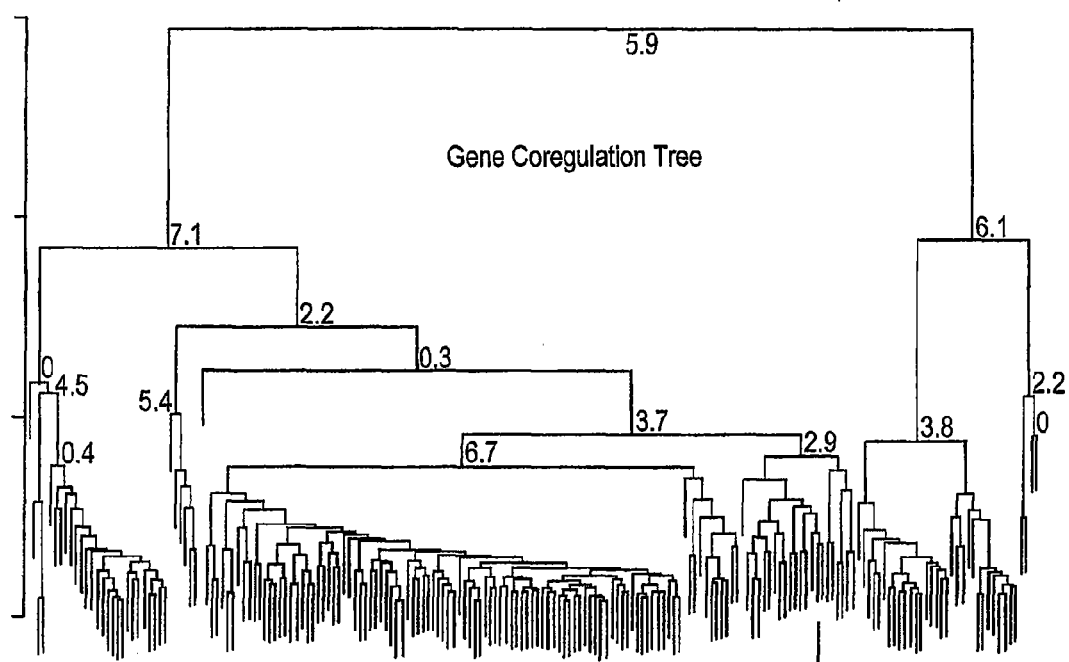
Figure 5C:
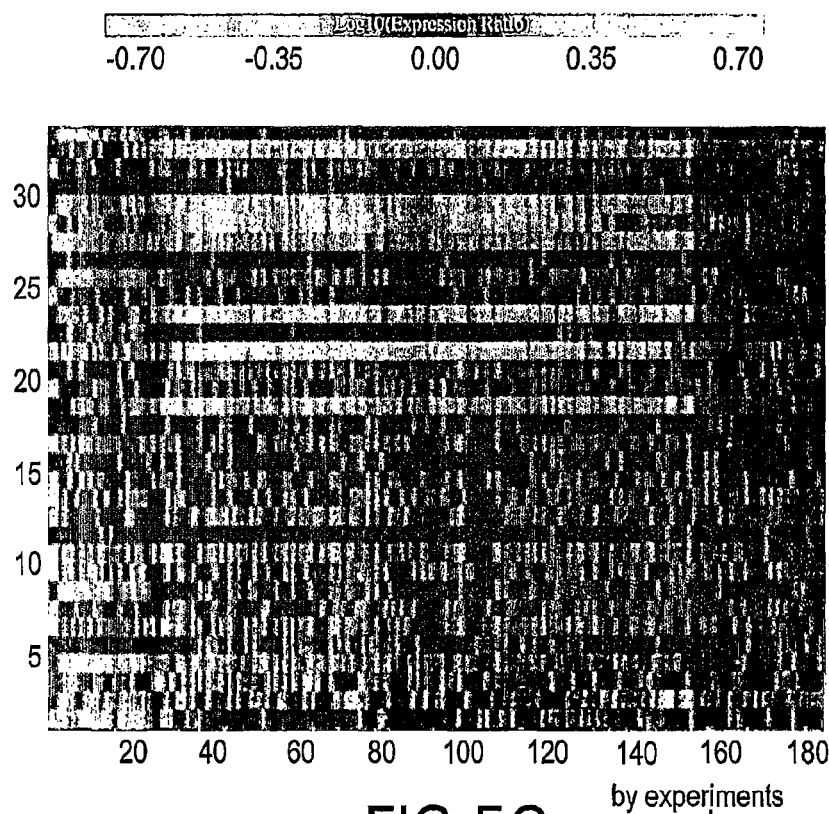
Figure 5D:
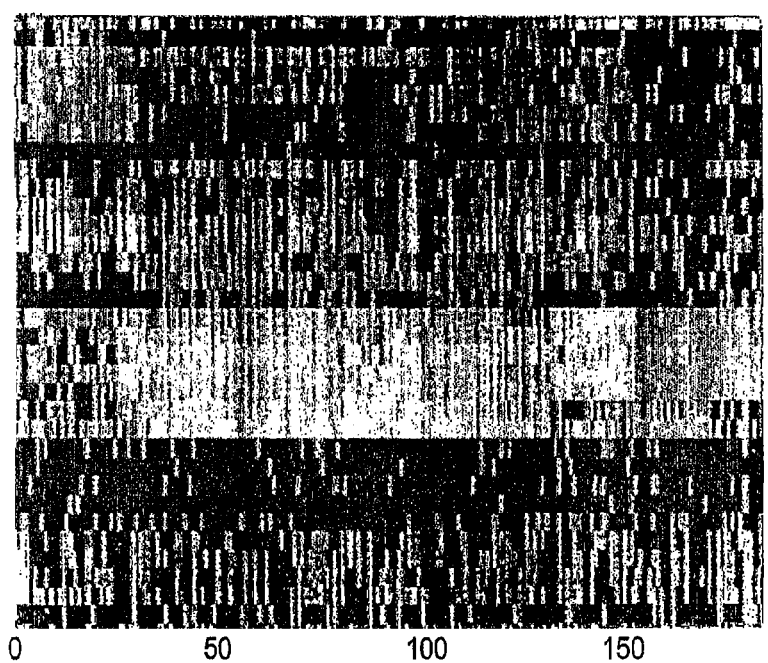

FIGS. 5A-D illustrate an exemplary application of the clustering methods described herein:

FIG. 5A is a display of 185 genetic transcripts of *S Cerevisiae* (horizontal axis) measured in 34 different perturbation experiments (vertical axis);

FIG. 5B shows the co-regulation tree obtained by clustering the genetic transcripts of FIG. 5A using the hclust clustering algorithm;

FIG. 5C is an illustration of the same experimental data in which the transcripts have been re-ordered according to the genesets defined from FIG. 5B;

FIG. 5D is another illustration of the experimental data in which the experimental index (vertical axis) has also been reordered according to clustering of the response profiles.

Figure 6:
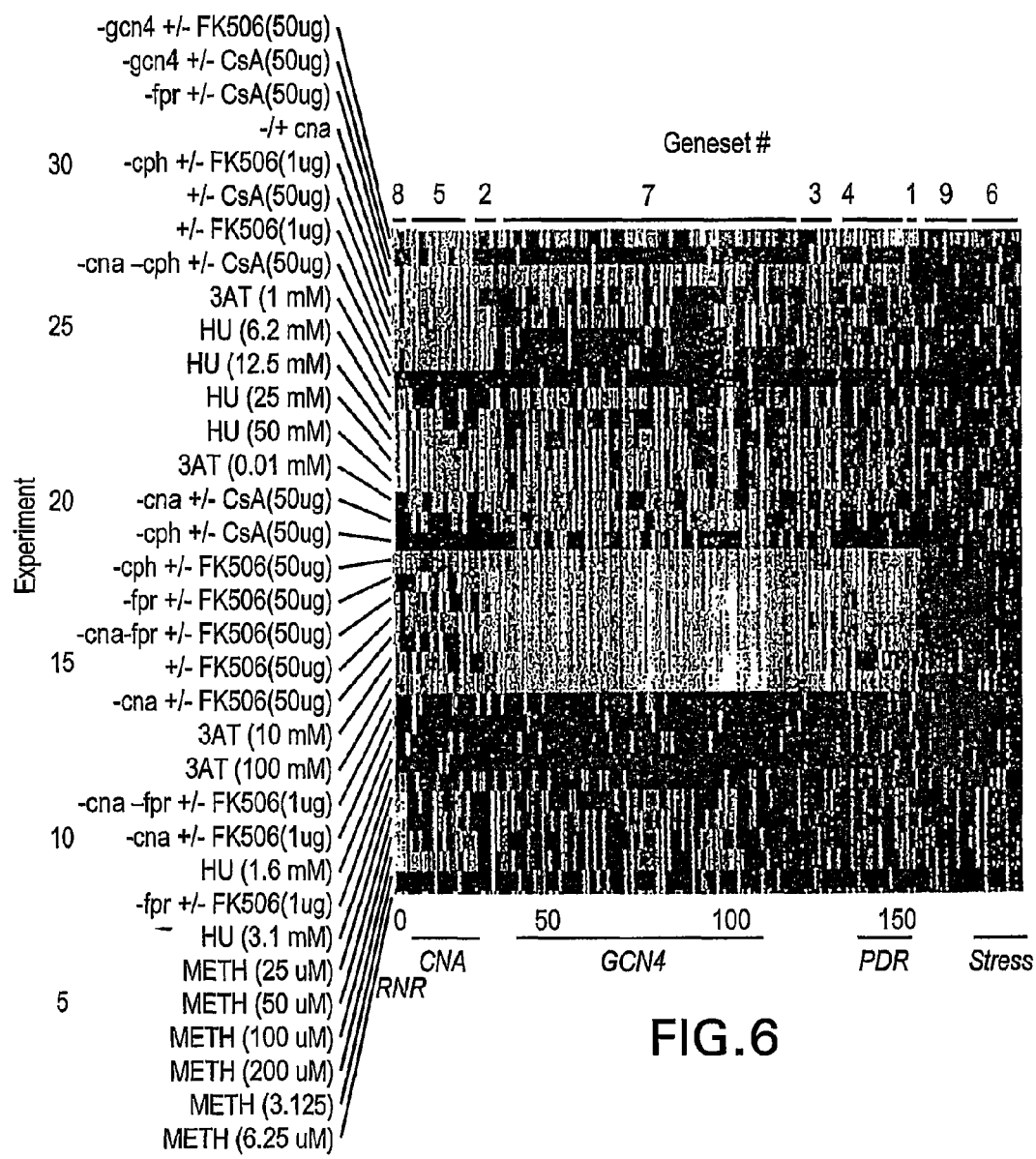
Figure 7A:
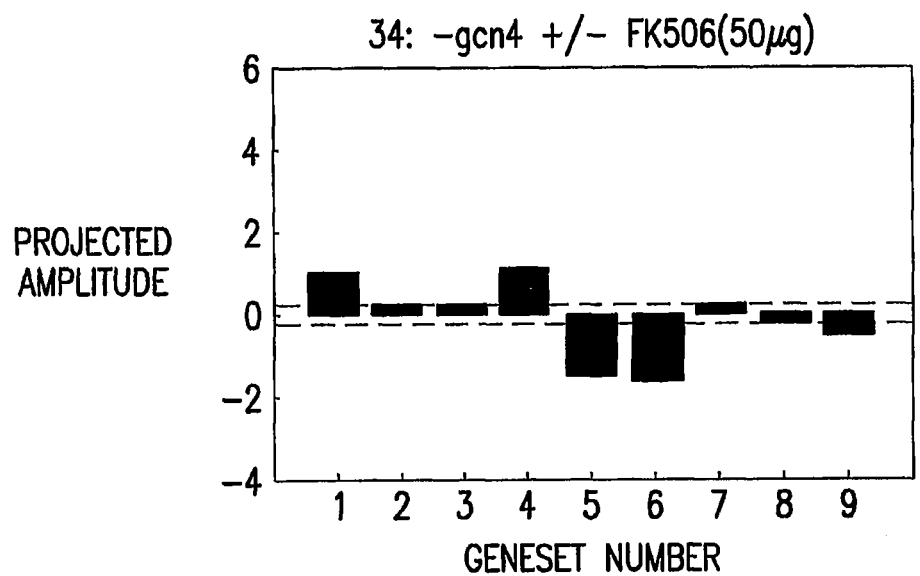
Figure 7B:
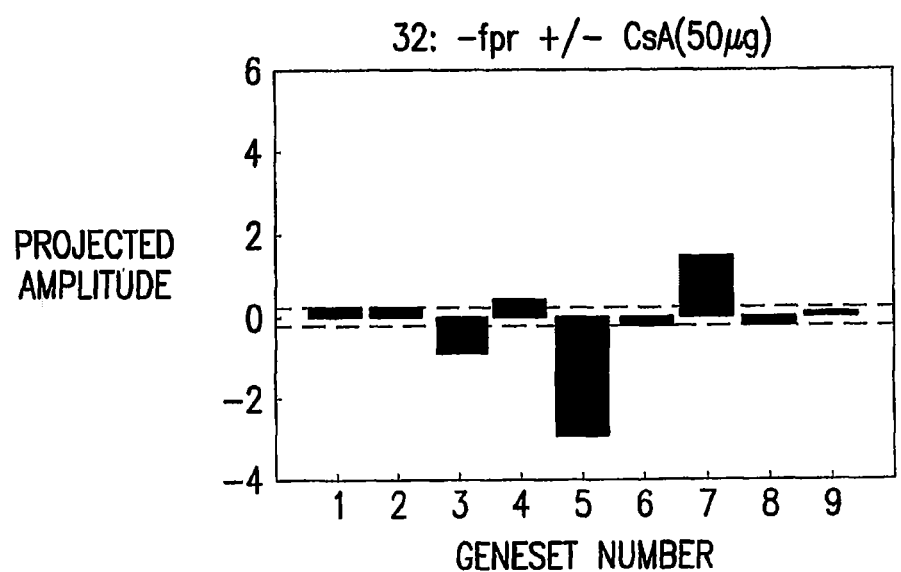
Figure 7C:
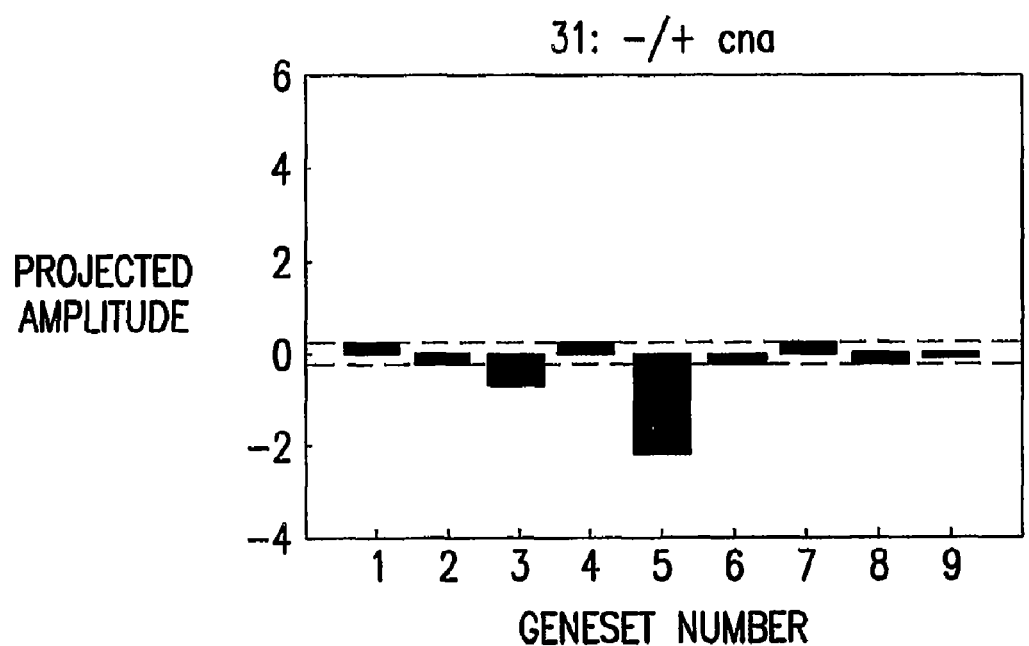
Figure 7D:
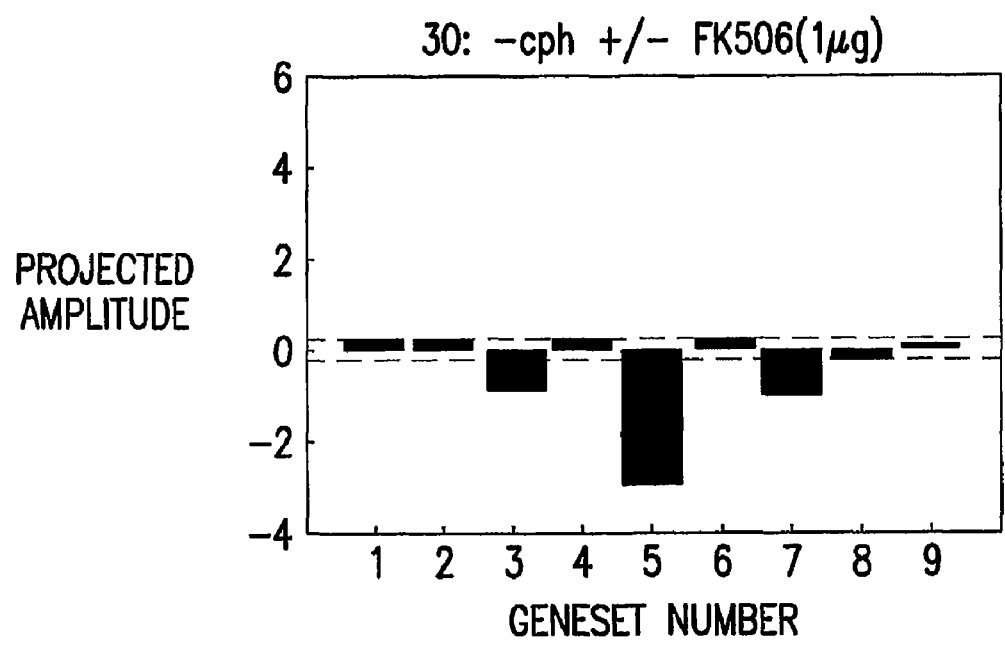
Figure 7E:
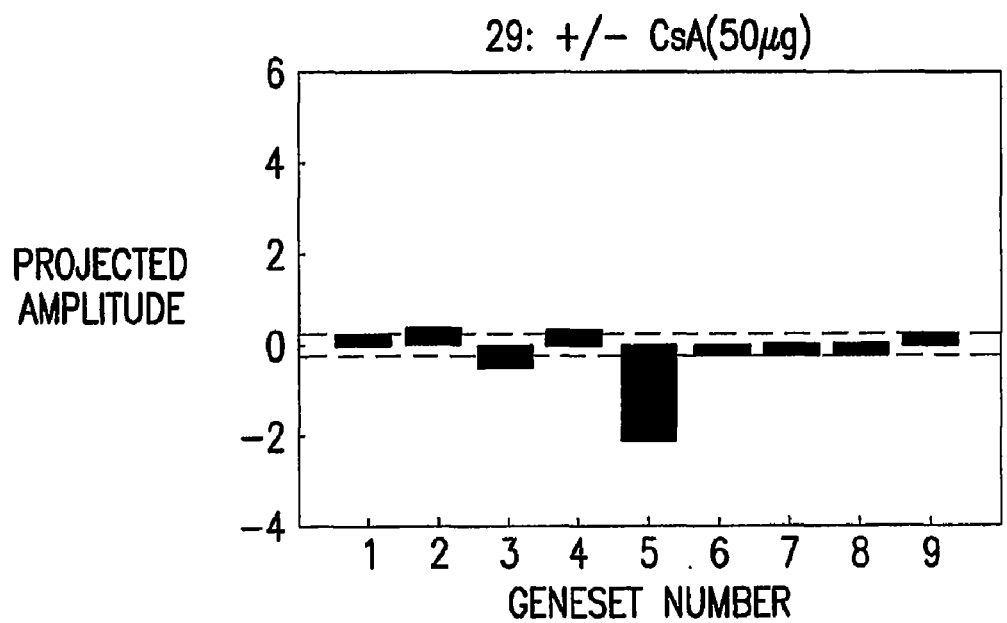
Figure 7F:
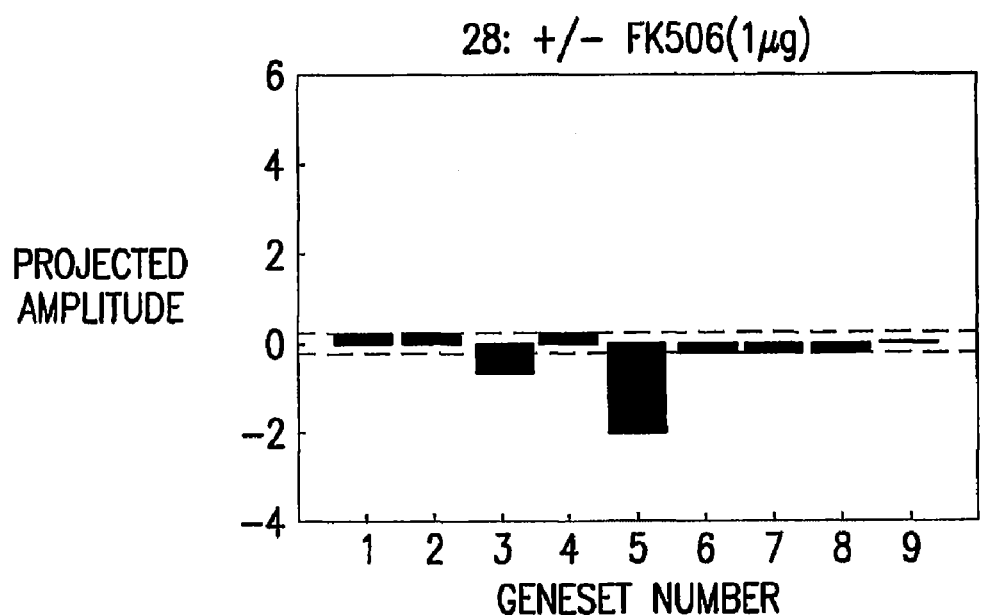
Figure 7G:
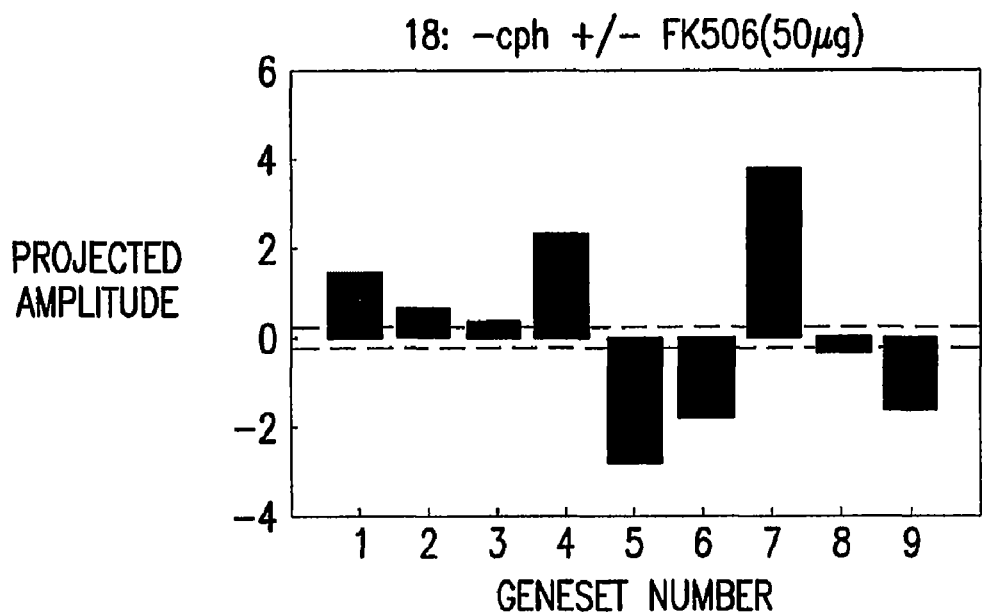
Figure 7H:
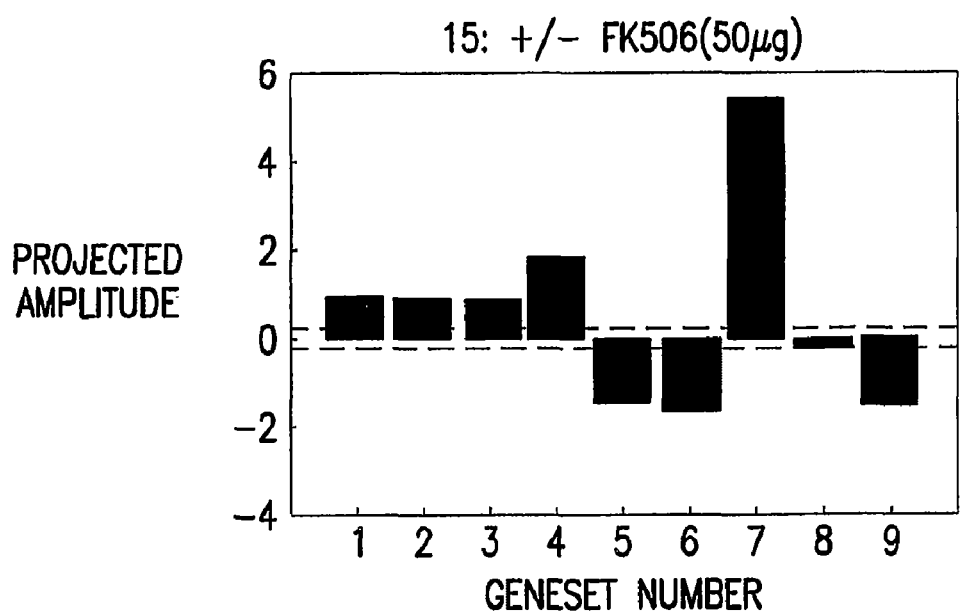

FIG. 6 is another illustration of the data in FIG. 5 in which the gene transcripts (horizontal axis) and experiments (vertical axis) are ordered according to similarity. Individual genesets are indicated above the image while the biological pathways and/or functions with which each geneset is associated are indicated below the image. The label of the vertical axis summarizes each experiments.

FIG. 7 shows bar charts indicating projected profiles for experiments 15, 18, 28-32 and 34 of FIG. 6.

Figure 8:
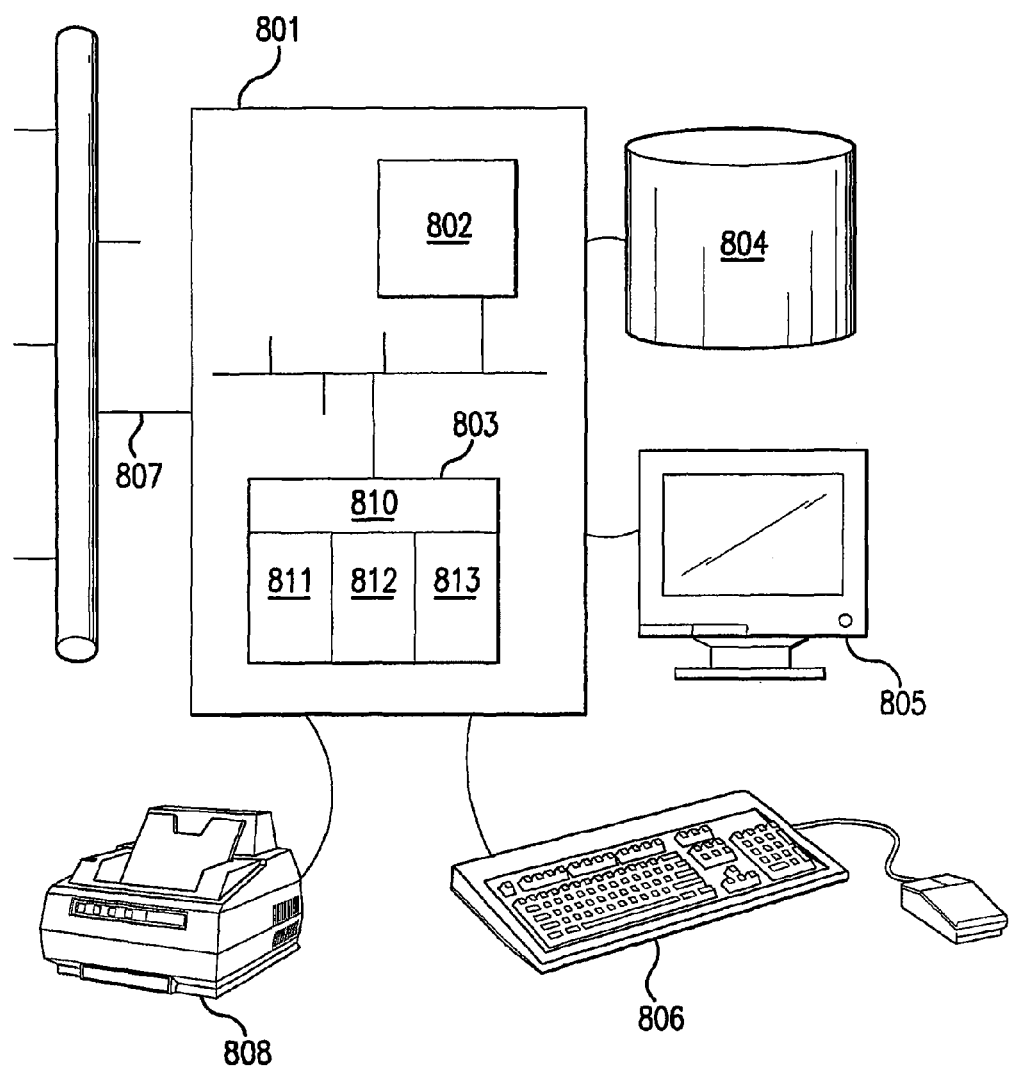

FIG. 8 illustrates an exemplary embodiment of a computer system useful for implementing the methods of the present invention.

Figure 9A:
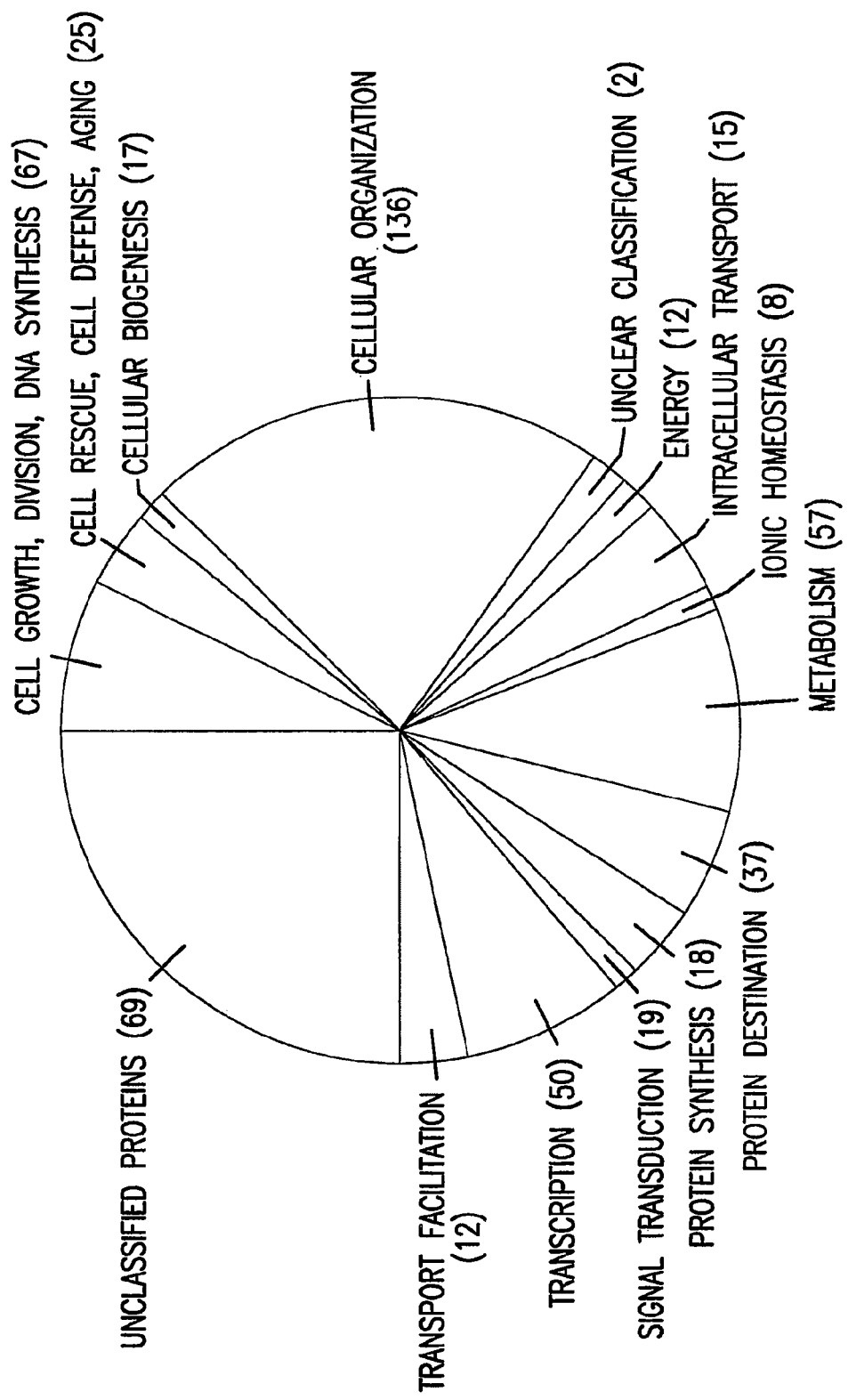
Figure 9B:
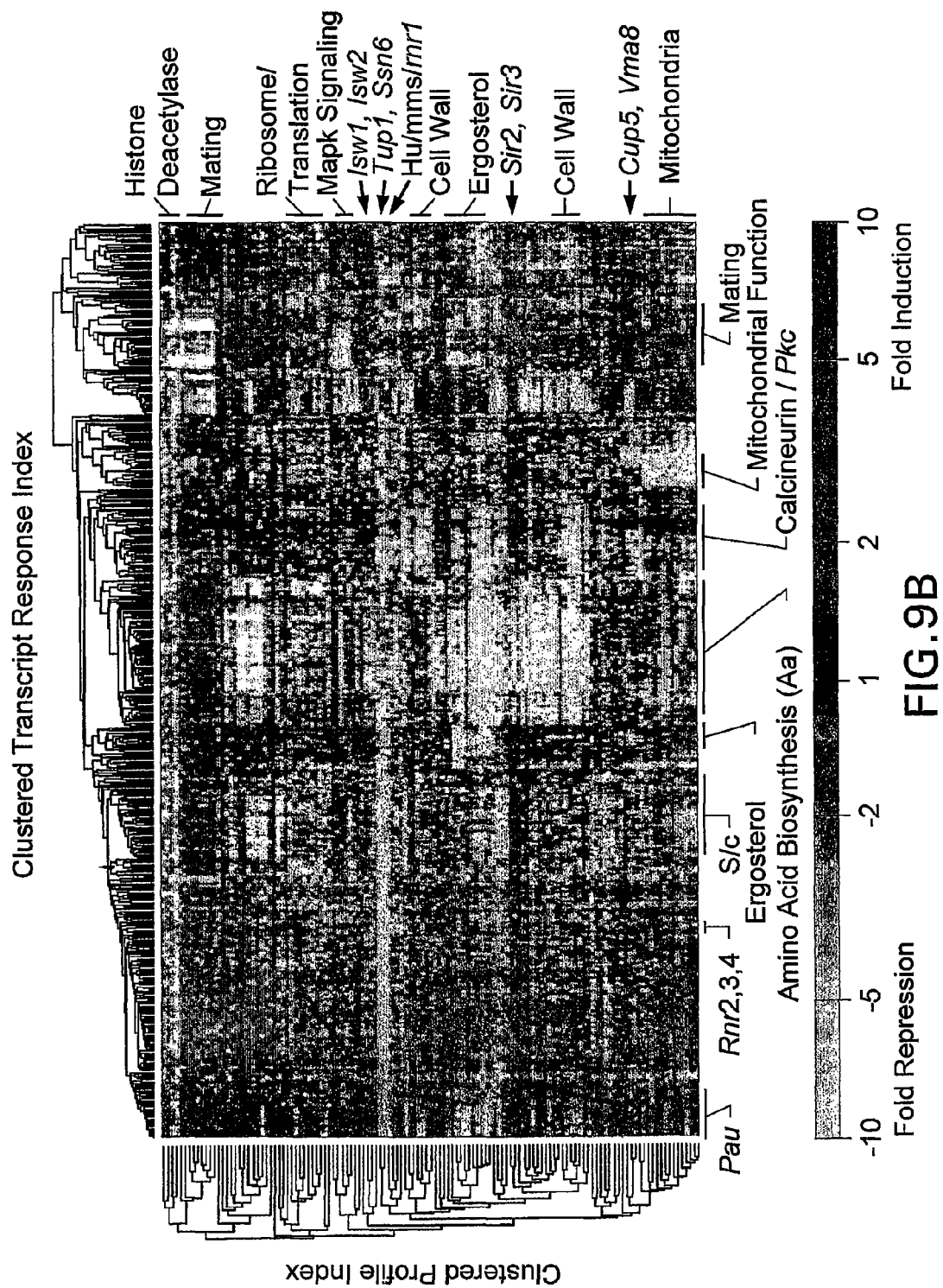
Figure 9C:
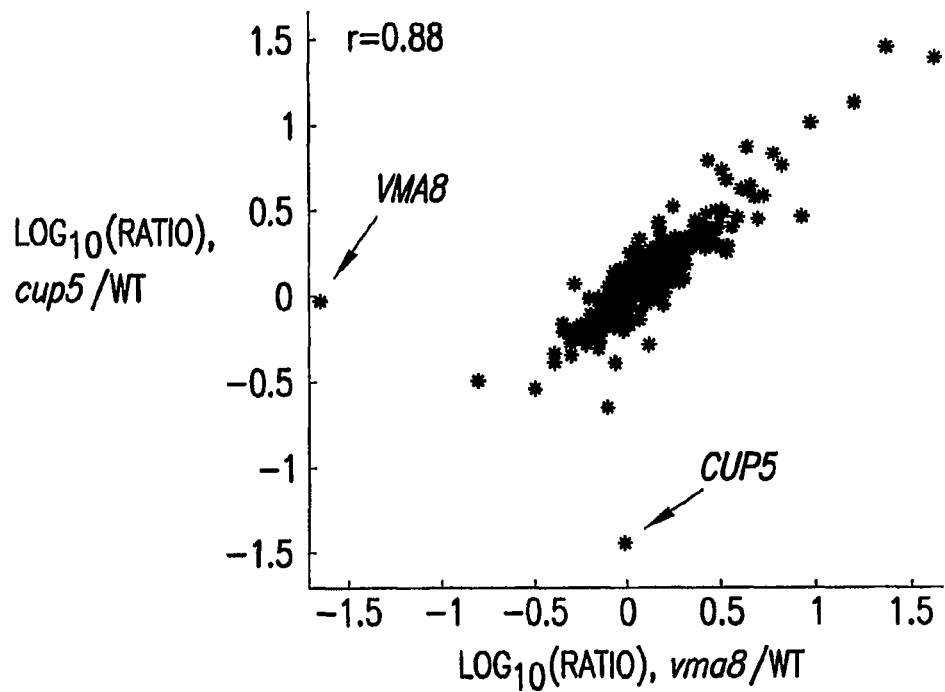

FIGS. 9A-E show expression profiles obtained from mutations in over 4% of all yeast genes:

FIG. 9A shows the distribution of mutants profiled among 15 major classes in the Munich Information Center for Protein Sequence (MIPS) (see Mewes et al., 1997, *Nucleic Acids Res.* 25:28-30) with the total number of genes profiled for each class indicated in parentheses (many genes are represented in multiple classes);

FIG. 9B illustrates the two-dimensional hierarchical clustering of 127 experiments (vertical axis) and 568 genes (horizontal axis) in the exemplary compendium of yeast response profiles described in Section 6.2, below;

FIG. 9C shows a comparison of the transcript profile ($Log_{10}$ of the expression ratio) of a homozygous cup5 disruption yeast strain to that of a homozygous vma8 disruption strain with genes that changed significantly from the wild-type at $P \leq 0.01$ in both strains indicated, genes changing significantly from wild-type at $P \leq 0.01$ in only cup5Δ or vma8Δ indicated, respectively, and anticorrelated genes at $P < 0.01$ in both experiments indicated.

Figure 9D:
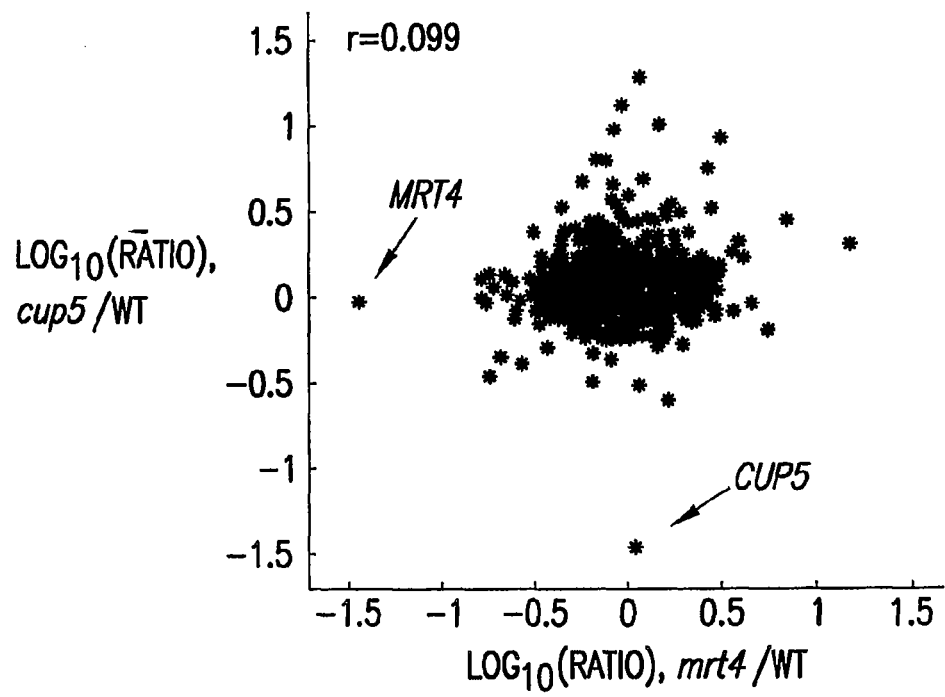
Figure 9E:
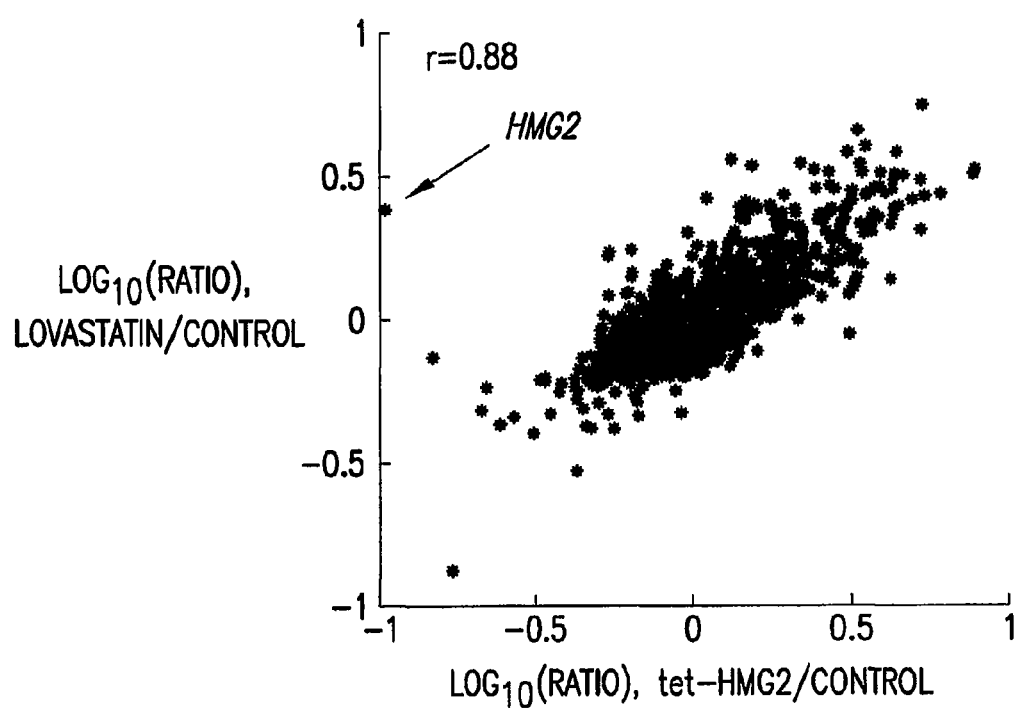

FIG. 9D shows a comparison of the transcript profile of the homozygous cup5 disruption yeast strain to that of a homozygous mrt4 disruption strain;

FIG. 9E shows a comparison of the transcript profile of lovastatin treatment to reduction in HMG2 transcript.

Figure 10A:
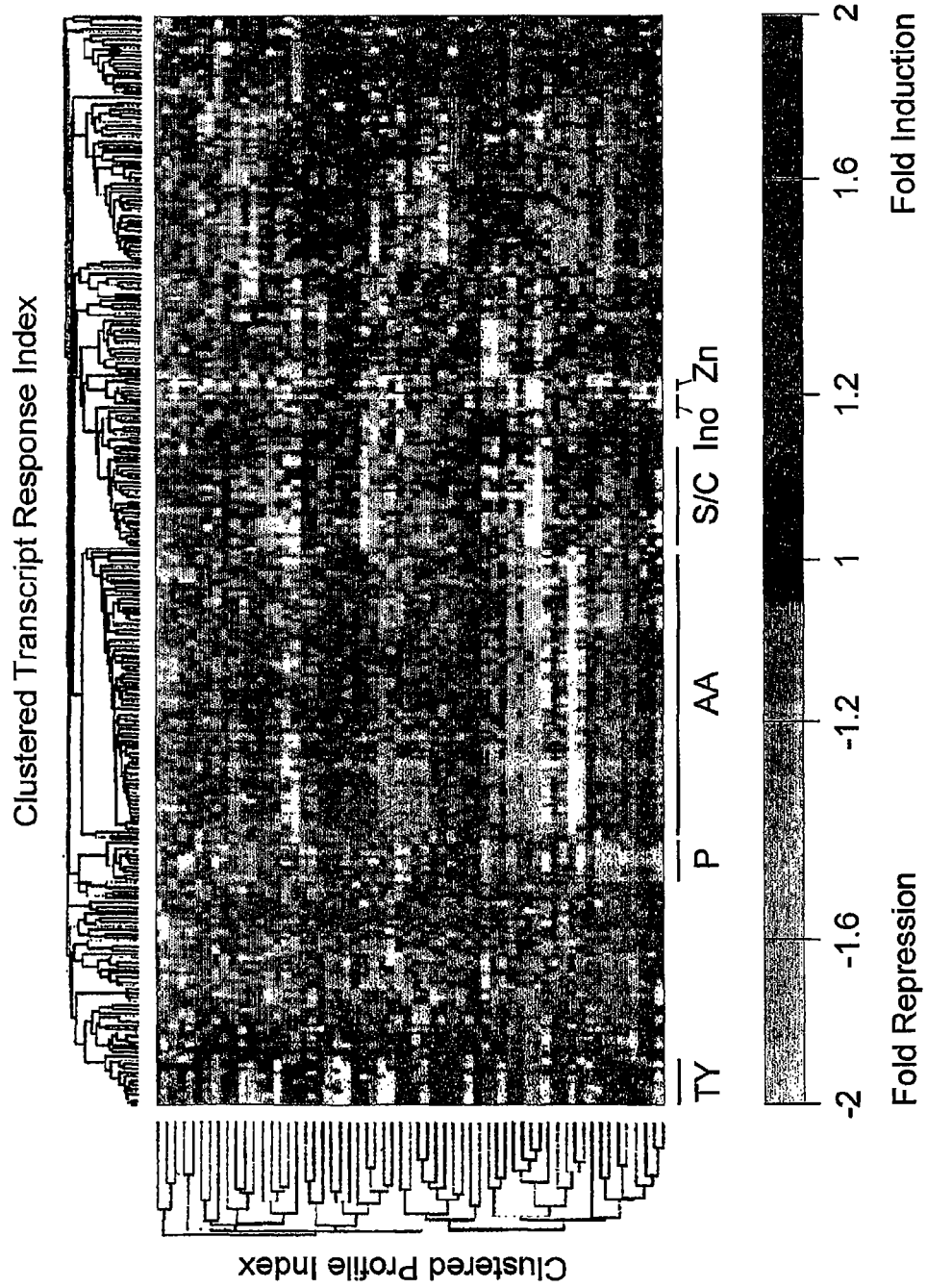
Figure 10B:
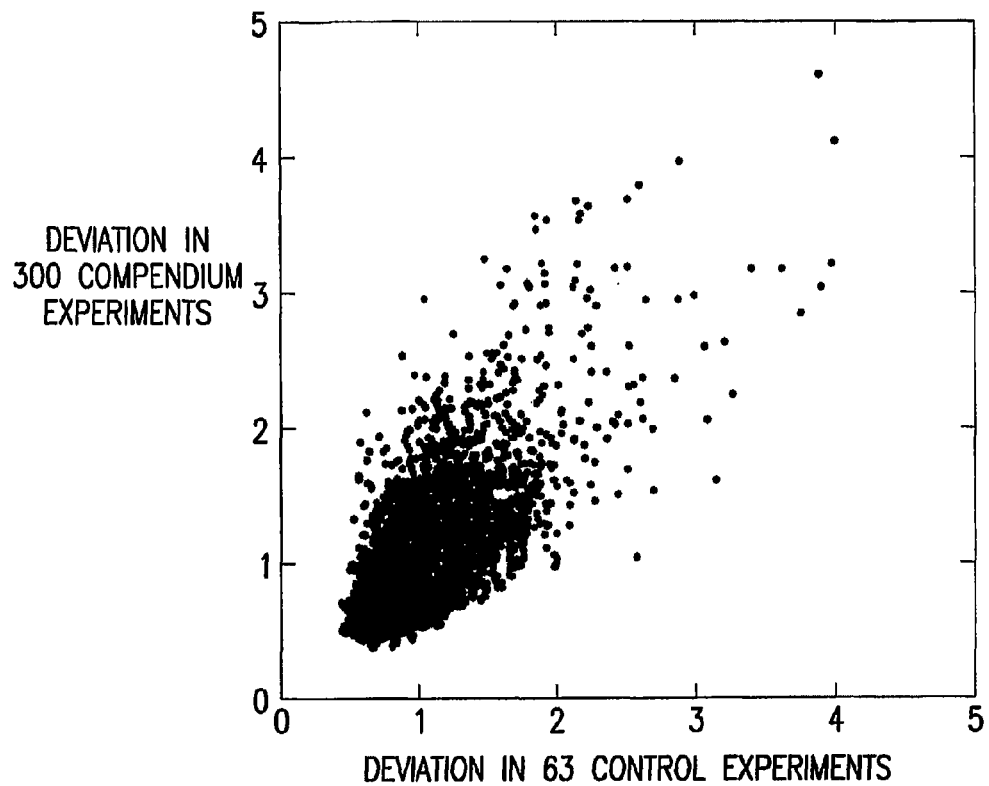
Figure 10C:
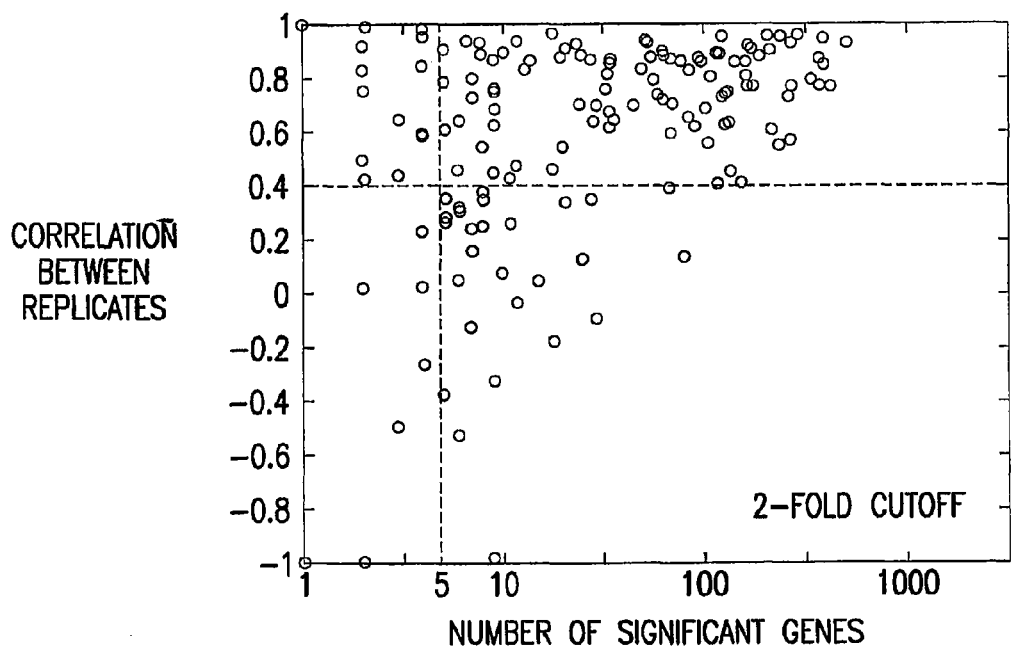
Figure 10D:
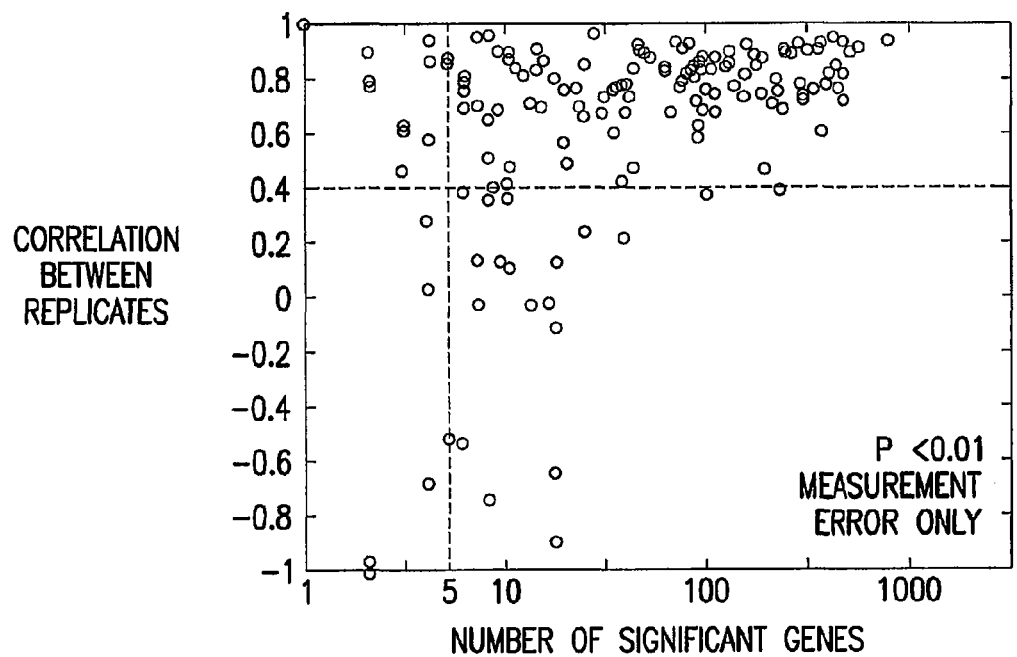
Figure 10E:
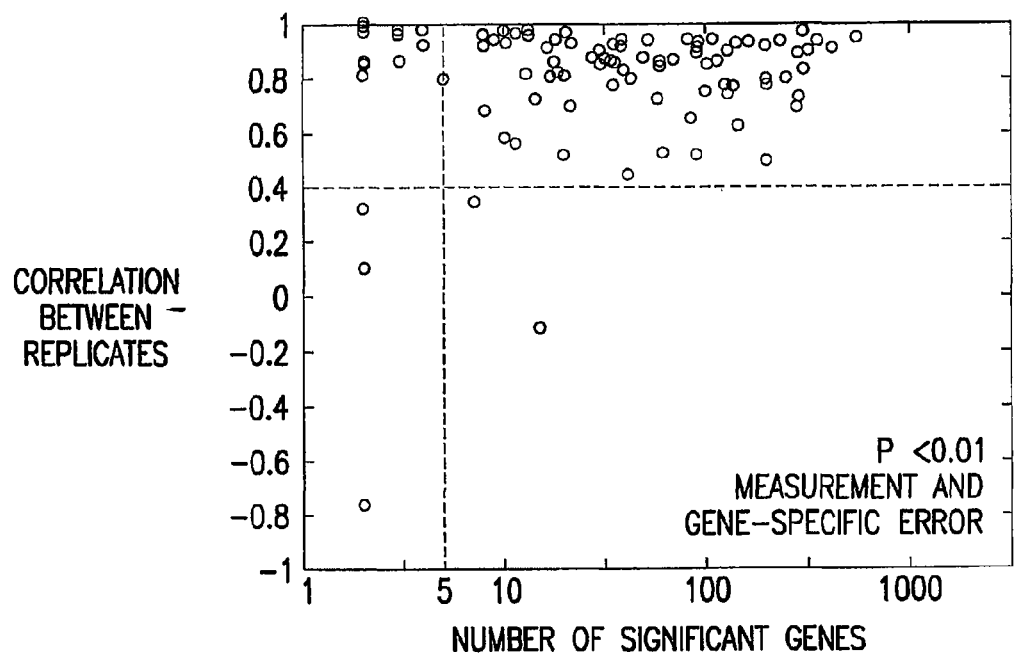

FIGS. 10A-E illustrate the improved reproducibility of expression profiles that is achieved by reducing the impact of commonly occurring transcriptional changes unrelated to experimental perturbations or modifications; specifically:

FIG. 10A shows the two-dimensional hierarchical clustering of 59 control experiments (vertical axis) and 278 genes (horizontal axis), selected to include only experiments in which two or more genes were up- or down-regulated at a statistical significance of $P \leq 0.15$ and only genes that are significant at $P \leq 0.15$ in two or more experiments using the statistical model described herein below to account for measurement error;

FIG. 10B shows a scatter plot comparing the scale factor Λ derived from 63 control experiments vs. Λ derived from 300 compendium experiments for each of 5835 yeast genes;

FIG. 10C shows the correlation between independent repeat measurements of 151 profiles from deletion mutants, using a 2-fold cutoff as the sole significance estimate;

FIG. 10D shows correlation between the same 151 repeat measurements with a significance cutoff of $P \leq 0.01$ using an error model accounting only for the quality of individual measurements (see Section 5.5.4 below);

FIG. 10E shows correlation between the same 151 repeats using an error model that accounts for both quality of individual measurements and for gene-specific variations in the 63 control experiments (see Section 5.5.4 below).

Figure 11A:
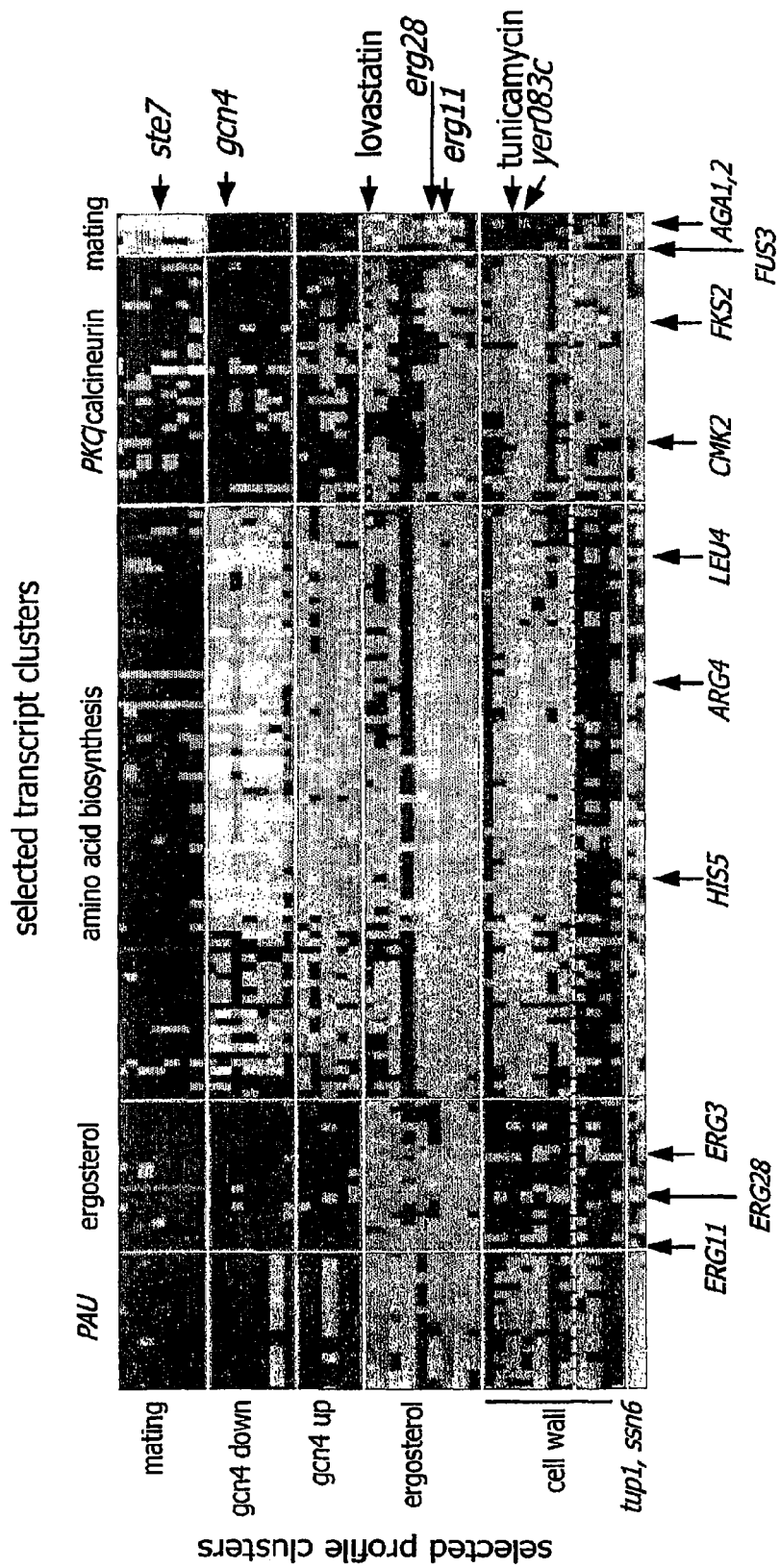
Figure 11B:
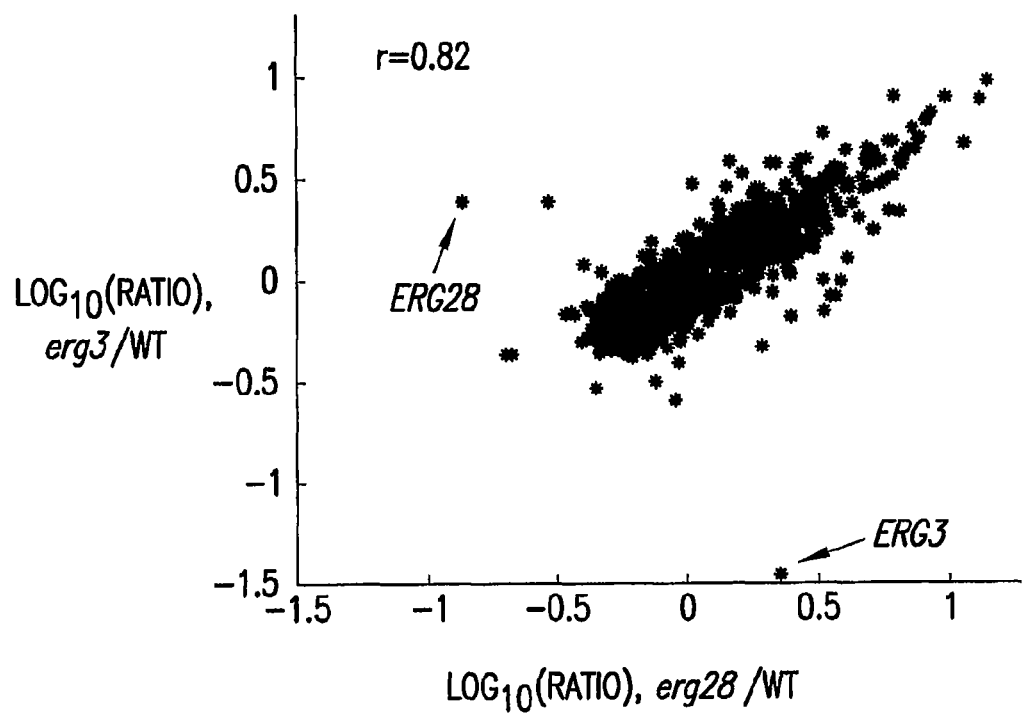
Figure 11C:
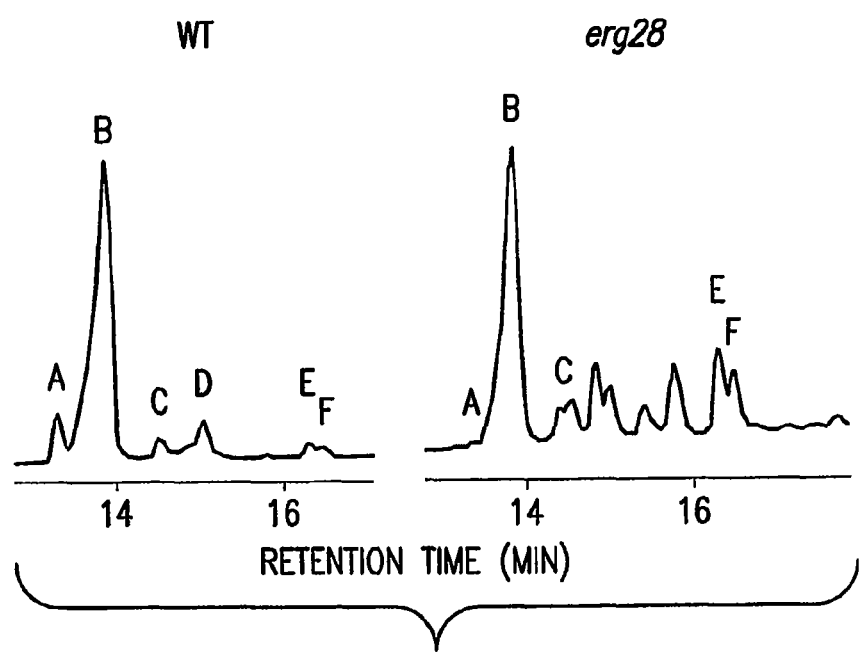
Figure 11D:
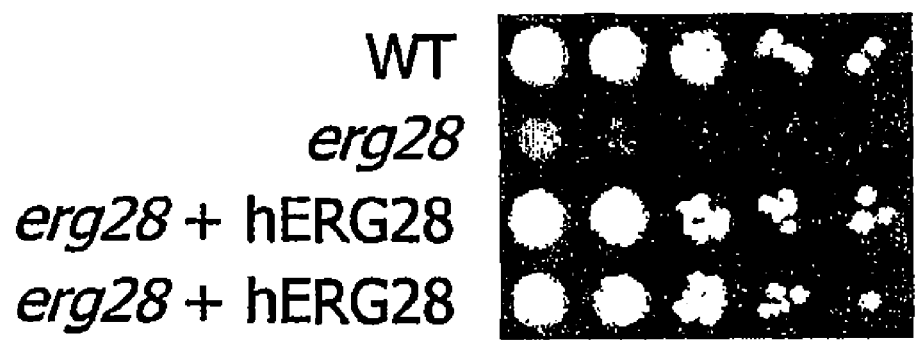
Figure 11E:
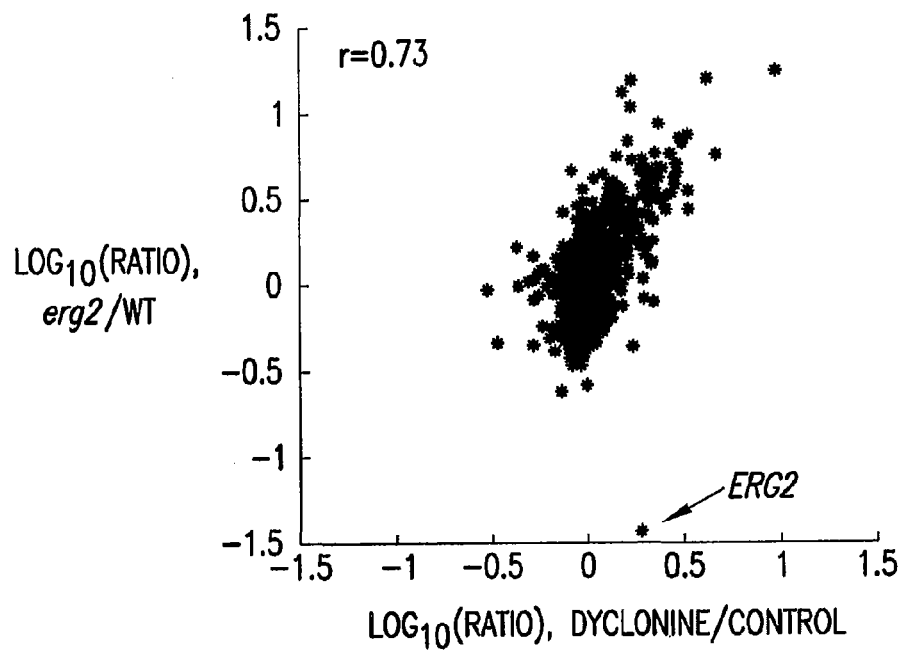
Figure 11F:
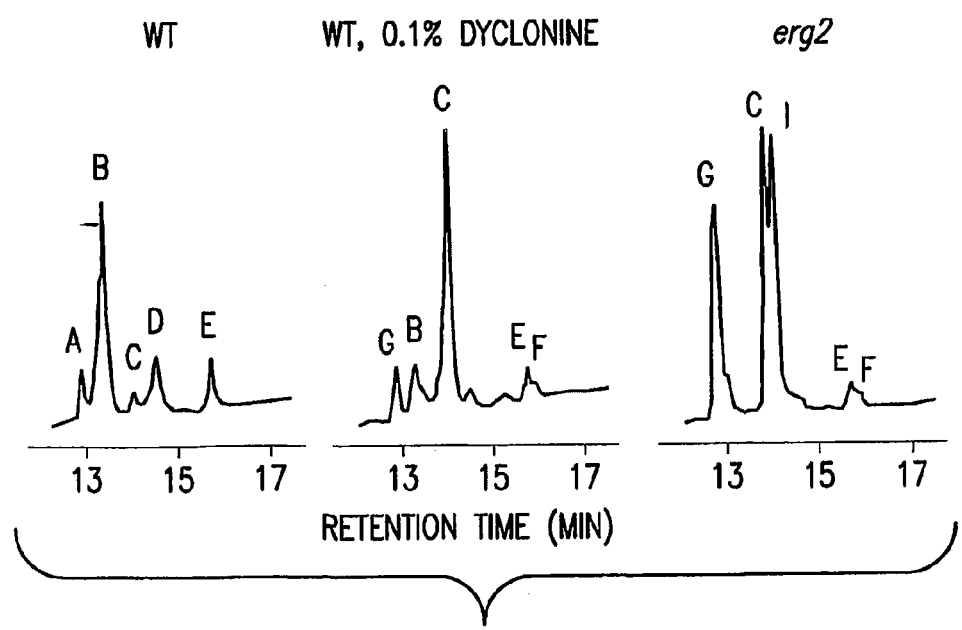

FIGS. 11A-F illustrate response profile similarities which identify sterol-pathway disturbances resulting from deletion of the previously uncharacterized ORF YER044c (also referred to herein as ERG28) and from cyclonine treatment:

FIG. 11A shows prominent gene clusters from FIG. 9B responding to modifications to cellular constituents involved in ergosterol biosynthesis;

FIG. 11B is a comparison of the transcript profile of an erg28Δ yeast strain to that of an erg3Δ yeast strain;

FIG. 11C shows the sterol profile of a wild-type yeast strain (left) and an erg28Δ deletion yeast strain (right);

FIG. 11D illustrates complementation of the erg28Δ strain's growth defect by plasmids expressing hERG28, the human homolog of ERG28;

FIG. 11E is a comparison of the transcript profile resulting from a six hour treatment with 0.063% dyclonine to that of an erg2Δ deletion yeast strain;

FIG. 11F shows sterol profile of wild-type (left), dyclonine-treated (middle) and erg2Δ (right) yeast strains.

Figure 12A:
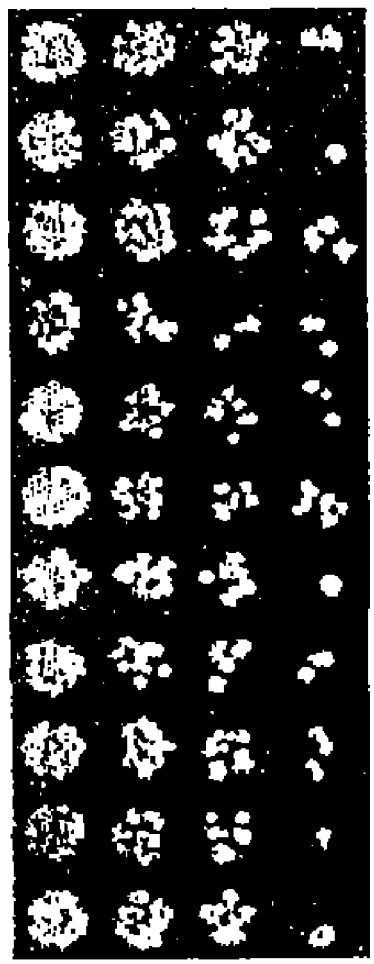
Figure 12A:
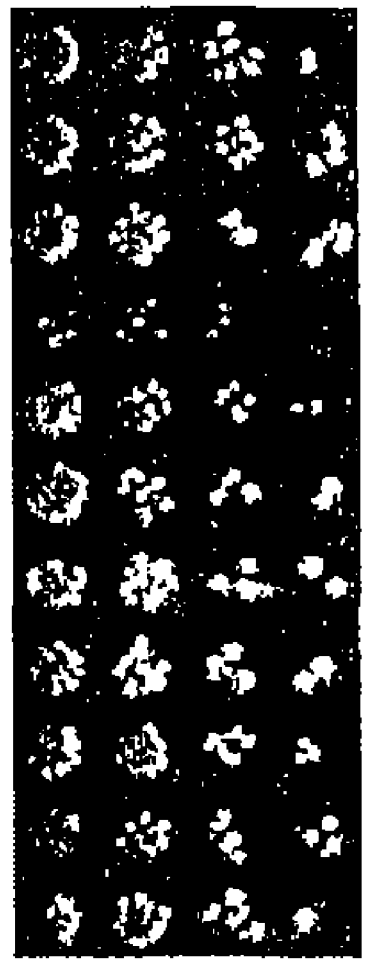
Figure 12B:
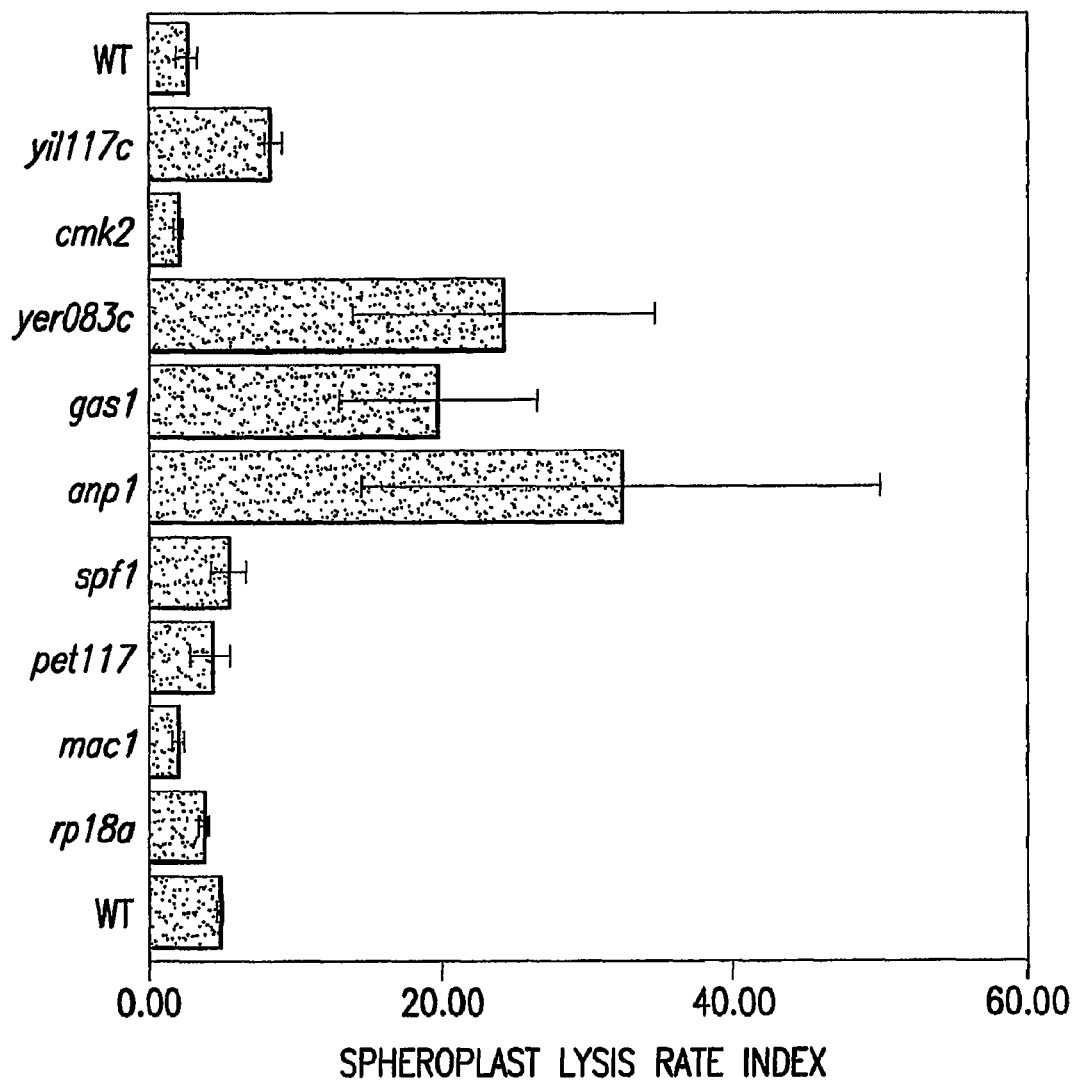

FIGS. 12A-B demonstrate the association of yer083cΔ with cell wall defects in yeast;

FIG. 12A illustrates the sensitivity of different yeast strains to calcofluor white;

FIG. 12B shows the rate index from spheroplast lysis assays conducted in parallel with different yeast strains.

Figure 13A:
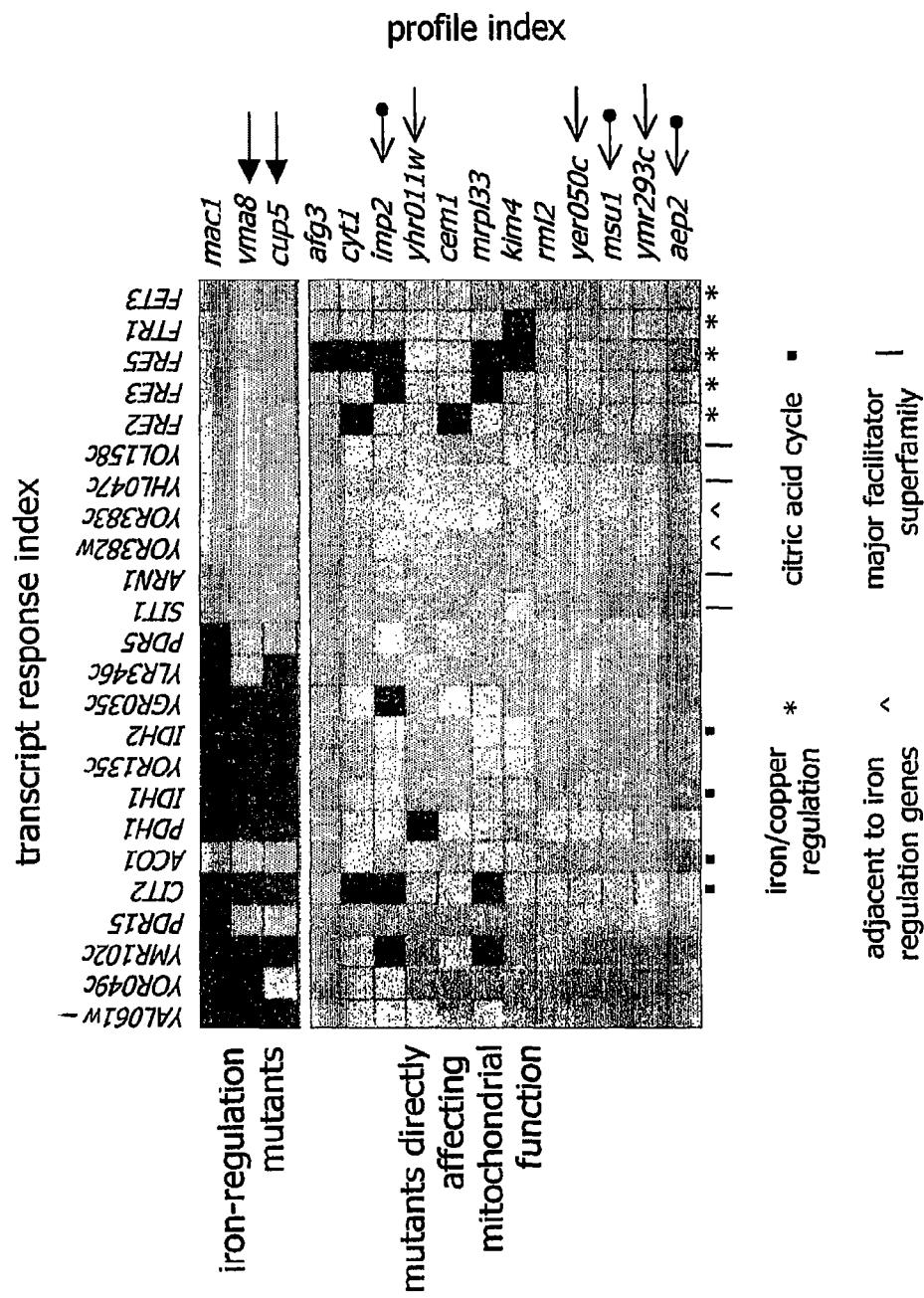
Figure 13B:
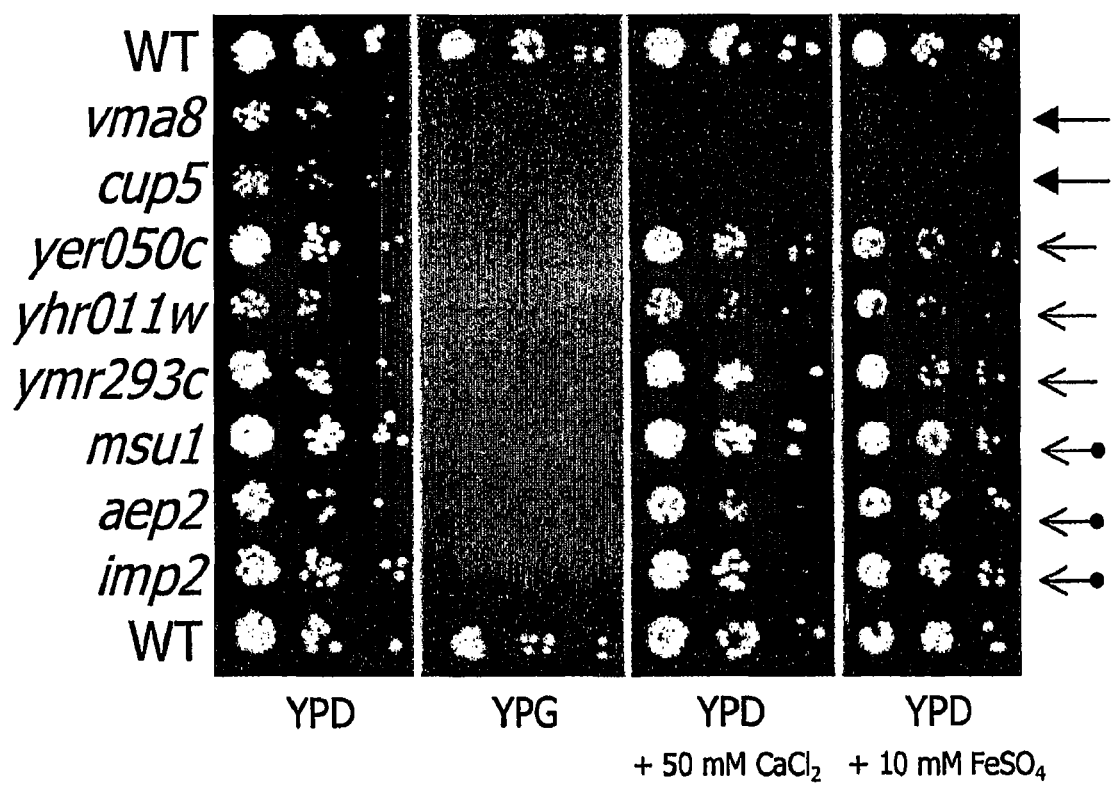

FIGS. 13A-B show the classification of mitochondrial dysfunction mutants by expression profiles:

FIG. 13A shows an enlarged view of two gene and experiment clusters from FIG. 9B;

FIG. 13B shows cell growth of different yeast strains (vertical axis) grown on plates containing either dextrose (YPD), glycerol (YPG), dextrose plus 50 mM $CaCl_2$ (YPD+50 mM $CaCl_2$), or dextrose plus 10 mM $FeSO_4$ (YPD+10 mM $FeSO_4$).

Figure 14A:
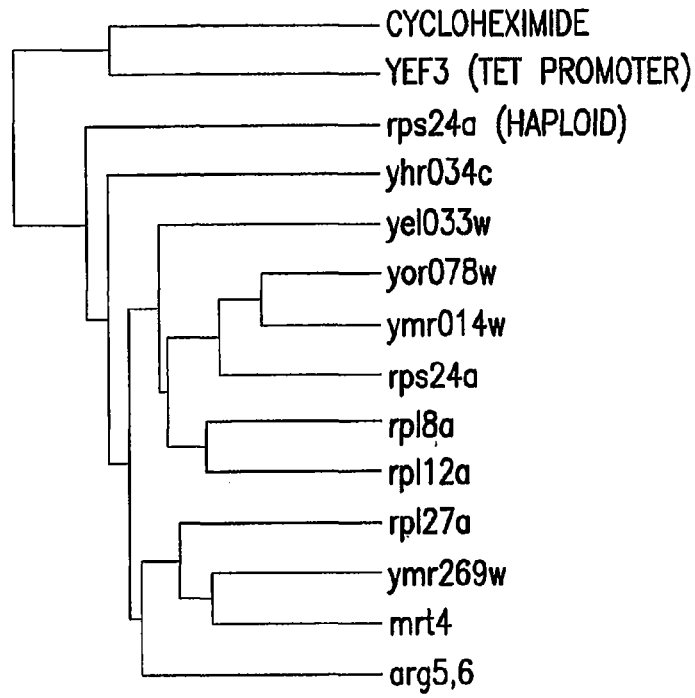
Figure 14B:
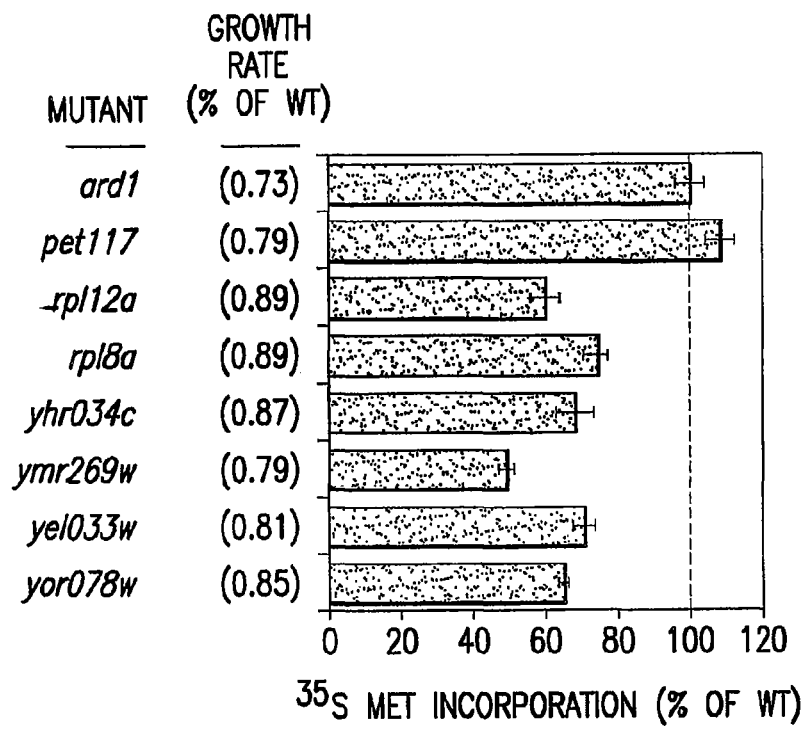

FIGS. 14A-B show subtle transcriptional changes which are consequences of novel mutations affecting protein synthesis;

FIG. 14A shows the cluster tree from a selected experiment cluster resulting from relaxing parameters of the clustering algorithm to accept experiments with 2 or more genes up- or down-regulated by 2-fold or more and significant at $P \leq 0.01$ and genes significant at $P \leq 0.01$ in two or more experiments FIG. 14B shows a bar graph indicating the $^{32}$S-Methionine incorporation rate of several mutant yeast strains (vertical axis) relative to a wild-type strain grown in parallel with the mutant (the strains ard1Δ and pet117Δ are included as negative controls).

5. DETAILED DESCRIPTION

This section presents a detailed description of the invention and its applications. The description is by way of several exemplary illustrations, in increasing detail and specificity, of the general methods of this invention. These examples are non-limiting, and related variants will be apparent to one of skill in the art.

Although, for simplicity, this disclosure often makes references to gene expression profiles, transcriptional rate, transcript levels, etc., it will be understood by those skilled in the art that the methods of the inventions are useful for the analysis of any biological response profile. In particular, one skilled in the art will recognize that the methods of the present invention are equally applicable to biological profiles which comprise measurements of other cellular constituents such as, but not limited to, measurements of protein abundance or protein activity levels.

5.1. Introduction

The state of a cell or other biological sample is represented by cellular constituents (any measurable biological variables) as defined in Section 5.1.1, infra. Those cellular constituents vary in response to perturbations. A group of cellular constituents may co-vary in response to particular perturbations. Accordingly, one aspect of the present invention provides methods for grouping co-varying cellular constituents. Each group of co-varying cellular constituents is termed a cellular constituent set. This invention is partially premised upon a discovery of the inventors that the state of a biological sample can be more advantageously represented using cellular constituent sets rather than individual cellular constituents. It is also a discovery of the inventors that the response of a biological sample can be better analyzed in terms of responses of co-varying cellular constituent sets rather than cellular constituents.

In some preferred specific embodiments of this invention, genes are grouped into basis genesets according to the regulation of their expression. Such "clustering" methods are well known in the art and are described with respect to the cellular constituents and response profiles of the present invention in Sections 5.2.3 and 5.2.4 hereinbelow and, further, in U.S. patent application Ser. Nos. 09/428,427, 09/220,275, 09/179,569 and 09/220,142 filed on Oct. 27, 1999, Dec. 23, 1998, Oct. 27, 1998, and Dec. 23, 1998, respectively. Transcript abundances of individual genes within a geneset are combined to obtain a single gene expression value for the geneset by a projection process. The expression values of genesets, rather than the transcriptional rate of individual genes, are then used as the basis for the comparison and detection of biological responses with greatly enhanced sensitivity.

This section first presents a background about representations of biological state and biological responses in terms of cellular constituents. Next, a schematic and non-limiting overview of the invention is presented, and the representation of biological states and biological responses according to the method of this invention is introduced. The following sections present specific non-limiting embodiments of this invention in greater detail.

5.1.1. Definition of Biological State

As used in herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample), or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample. It is noted that, as used herein, the term "cellular constituent" is not intended to refer to known subcellular organelles such as mitochondria, chloroplasts, lysozomes, etc.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of a drug or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of a drug of interest. As is known to those of skill in the art, the transcriptional state is often representative of the translational state.

Other aspects of the biological state of a biological sample are also of use in this invention. For example, the activity state of a biological sample, as that term is used herein, includes the activities of the constituent protein species (and also, optionally, catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

Preferably, the biological state of a biological sample (e.g., of a cell or cell culture) is represented by a profile of a plurality of cellular constituents. Such a profile of cellular constituents can be represented, for example, by a vector S, $$S=[S_1, \ldots, S_i, \ldots, S_k]$$ (Equation 1)

wherein $S_i$ is the level or value of the i'th cellular constituent. For example, $S_i$ can be the transcription level of gene i or, alternatively, the abundance or activity level of protein i.

In certain embodiments, the elements $S_i$ are continuous variables. For example, transcriptional rates are typically indicated as numbers of molecules synthesized per unit of time. Transcriptional rates can also be indicated as percentages of a control rate. In certain other embodiments, the elements $S_i$ can be categorical variables. For example, transcriptional rates can be indicated as either "on" or "off," where the value "on" indicates a transcriptional rate above a user determined threshold values and "off" indicates a transcriptional rate below that threshold.

5.1.2. Representation of Biological Responses

The response of a biological sample to a perturbation, for example the application of a drug or a particular genetic mutation, can be measured by observing changes in the biological state of the sample. A response profile is a collection of such changes of cellular constituents. For example, the response profile of a biological sample (e.g., a cell or cell culture) to the perturbation in can be represented by the vector $v^{(m)}$, $$v^{(m)}=[v_1^{(m)}, \ldots, v_i^{(m)}, \ldots, v_k^{(m)}]$$ (Equation 2).

In Equation 2, $v_i^{(m)}$ is the amplitude of the response of cellular constituent i under the perturbation m. In some embodiments, $v_i^{(m)}$ can be simply the difference between the measured amounts, e.g., abundances, activity levels or levels of modification, of cellular constituent i before and after the perturbation m is applied to the biological sample or, similarly, the difference in measured amounts of cellular constituent i between a biological sample that is subject to the perturbation m and a sample that is not subject to the perturbation m. In other embodiments, $v_i^{(m)}$ can be the ratio (or, more preferably, the logarithm of the ratio) of the measured amounts of cellular constituent i before and after the perturbation m is applied to the biological sample or, more preferably, the ratio (or, still more preferably, the logarithm of the ratio) of the measured amounts of cellular constituent i in a sample subject to the perturbation in to a sample that is not subject to the perturbation m.

In a particularly preferred embodiment of the present invention, the perturbations m comprise mutations to one or more genes of a cell or organism. Such mutations can include, for example, genetic "knockouts" in which one or more particular genes of the cell or organism are deleted or inactivated, e.g., by standard techniques, such as homologous recombination, that are well known in the art. Such mutations can also include over expression mutants in which one or more particular genes are expressed at elevated levels in the cell or organism. In such embodiments, the response $v_i^{(m)}$ of the i'th cellular constituent to a particular mutation (e.g., the mutation of gene m) can simply be the difference between the measured amounts of cellular constituent i in a cell or cells having the particular mutation and in a cell or cells that do not have the genetic mutation. In other such embodiments, $v_i^{(m)}$ can be the ratio (or, more preferably, the logarithm of the ratio) of the measured amounts of cellular constituent i in a cell or cells having the particular mutation and in a cell or cells that do not have the particular mutation. In still other embodiments, the response $v_i^{(m)}$ of the i'th cellular constituent to a particular mutation (e.g., the mutation of gene in) can be the absolute amount of cellular constituent i in the cell or cells having the particular mutation, e.g., the number of mRNA molecules per cell.

In other embodiments, the perturbations can comprise exposure to one or more drugs, including exposure to one or more levels (i.e. dosages) of a drug or drugs. In such embodiments, the response $v_i^{(m)}$ of the i'th cellular constituent to a particular drug (e.g., exposure to dosage u of the drug m) can simply be the difference between the measured amounts of cellular constituent i in a cell or cells exposed to the drug and in a cell or cells that are not exposed to the drug. In other such embodiments, $v_i^{(m)}$ can be the ratio (or, more preferably, the logarithm of the ratio) of the measured amounts of cellular constituent i in a cell or cells exposed to the drug and in a cell or cells that are not exposed to the drug. In still other embodiments, the response $v_i^{(m)}$ of the i'th cellular constituent in a cell or cells exposed to the drug can be the absolute amount of cellular constituent i in the cell or cells exposed to the drug, e.g., the number of mRNA molecules per cell.

In preferred embodiments, $v_i^{(m)}$ is set equal to zero for all cellular constituents i whose responses are below a threshold amplitude or confidence level which can be determined, e.g., from knowledge of the measurement error behavior. For example, in some embodiments, only cellular constituents that have a response greater than or equal to two standard errors in more than N profiles may be selected for subsequent analysis, where the number of profiles N is selected by a user of the invention.

For those cellular constituents whose responses are above the threshold amplitude, $v_i^{(m)}$ may be equal to the measured value. For example, in embodiments wherein the perturbation m comprises graded levels of exposure to a perturbation such as graded levels of exposure to a drug, n, $v_i^{(m)}$ may be made equal to the expression and/or activity of the i'th cellular constituent at the highest concentration of the drug m. Alternatively, the response at different levels of perturbations (e.g., different drug concentrations) $u_l$ may be interpolated, to a smooth, piece-wise continuous function, e.g., by spline- or model-fitting, and $v_i^{(m)}$ made equal to some parameter of the interpolation. For example, in spline-fitting the response data to various levels of the perturbation m are interpolated by summing products of an appropriate spline interpolation function S multiplied by the measured data values, as illustrated by Equation 3:

$$v_i^{(m)}(u) = \sum_l S(u - u_l) \times v_i^{(m)}(u_l) \qquad \text{(Equation 3)}$$

The variable "u" in Equation 3, above, refers to an arbitrary value of the perturbation (e.g., the drug exposure level or concentration) where the perturbation response of the i'th cellular constituent is to be evaluated. In general, S can be any smooth, or at least piece-wise continuous, function of limited support having a width characteristic of the structure expected in the response functions. An exemplary width can be chosen to be the distance over which the response function being interpolated rises from 10% to 90% of its asymptotic value. Exemplary S function include linear and Gaussian interpolation.

In model-fitting, the response data to various levels $u_l$ of the perturbation n are interpolated by approximating the response by a single parameterized function. An exemplary model-fitting function appropriate for approximating transcriptional state data is the Hill function:

$$H(u) = \frac{a(u/u_0)^n}{1 + (u/u_0)^n} \qquad \text{(Equation 4)}$$

The Hill function shown in Equation 4, above, comprises adjustable parameters of: (1) an amplitude paramter a; (2) an exponent n; and (3) an inflection point parameter $u_0$. The adjustable parameters are selected independently for each cellular constituent. Preferably, the adjustable parameters are selected so that for each cellular constituent of the perturbation response the sum of the squared of the distances of $H(u_l)$ from of $v_i^{(m)}(u_l)$ is minimized. This preferable parameters adjustment method is well known in the art as a least squares fit of H( ) to $v_i^{(m)}($ ). Such a fit can be done using any of the many available numerical methods known in the art (see, e.g., Press et al., 1996, *Numerical Recipes in C*, 2nd Ed., Cambridge University Press, Chpts. 10 and 14; Branch et al., 1996, *Matlab Optimization Toolbox User's Guide*, Mathworks, Natick, Mass.). The response amplitude $v_i^{(m)}$ can then be selected to be equal to, e.g., the amplitude parameter a in Equation 4.

In an alternative embodiment, the response profile data may be categorical. For example, in a binary approximation the response amplitude $v_i^{(m)}$ is set equal to zero if there is no significant response, and is set equal to 1 if there is a significant response. Alternatively, in a trinary approximation the response amplitude: (1) is set equal to +1 if cellular constituent i has a significant increase in expression or activity to perturbation n; (2) is set equal to zero if there is no significant response; and (3) is set equal to −1 if there is a significant decrease in expression or activity. Such embodiments are particularly preferred if it is known or suspected that the responses to which the response provile $v_i^{(m)}$ is to be compared do not have the same relative amplitudes as $v_i^{(m)}$ but do involve the same cellular constituents. In yet other embodiments, it is desirable to use "Mutual Information" as described, e.g., by Brunel (1998, *Neural Computation* 10(7): 1731-1757).

In all of the above-described embodiments, it is often preferred to normalize the response profile by scaling all elements of the vector $v_i^{(m)}$ (i.e., $v_i^{(m)}$ for all i) by the same constant so that the vector length $|v^{(m)}|$ is unity. Generally, the vector length can be defined by Equation 5:

$$|v^{(m)}| = \sum_i (v_i^{(m)})^2 \qquad \text{(Equation 5)}$$

5.2. Overview of the Invention

The present invention provides methods for enhanced detection, classification and pattern recognition of biological responses to different stimuli or "perturbations." In particular, the invention provides methods for characterizing particular cellular constituents of a cell or organism, including methods for characterizing genes and gene products of a cell or organism. The invention provides improved, robust methods for detecting structures in the response of biological systems to various perturbations such as the response to a genetic mutation, a drug, a drug candidate or an experimental condition that probes one or more biological pathways. The various perturbations can also include changes in biological systems that correspond to a particular disease or disease state or to treatment of a particular disease or disease state.

The inventors have discovered that expression profiles can be used as indicators or markers of a cell or organism's phenotype. Thus, the invention permits characterization of novel mutants using a single genome-wide expression measurement. The inventors have also discovered that mutants of a cell or organism can be systematically characterized using a comprehensive database or "compendium" of perturbation profiles.

The methods of the invention are first described, generally, in Section 5.2.1, below. Alternative embodiments of the invention are described in Section 5.2.2. Next, Section 5.2.3 describes databases or "compendiums" of perturbation response profile data with which the methods of the invention are preferably implemented and practiced. Sections 5.2.4 through 5.2.7 next describe the analytical aspects of the invention. In particular, these sections describe and enable methods for determining "co-varying sets" of cellular constituents, grouping measured biological response profiles, and determining projected and consensus profiles, respectively.

Section 5.3 describes particular systems (i.e., computer systems) that can be used to implement the methods described hereinbelow and which are therefore considered part of the present invention. Finally, Section 5.4 describes and enables numerous exemplary methods for perturbing (i.e., modifying) cellular constituents and Section 5.5 describes and enables various exemplary and preferred methods for measuring response profiles from such modifications.

5.2.1. General Methods

The methods of the present invention permit a user to identify a biological function of a cellular constituent of interest by comparing a response profile for a biological sample in which the cellular constituent of interest has been "perturbed" (i.e., modified) to a plurality of other response profiles for the biological sample in which other cellular constituents have been perturbed. For example, a cellular constituent can be characterized according to the methods of the present invention as having a biological function associated with cell growth, cell division, DNA synthesis, cell rescue, cell defense, aging, cellular biogenesis, cellular organization, respiration, energy production, intracellular transport, ionic homeostasis, metabolism, protein destination, protein synthesis, protein degradation, signal transduction, transcription and transport facilitation to name a few. Many other biological functions for cellular constituents such as genes and gene products have been documented (see, e.g., Mewes et al., 1997, Nucl. Acids Res. 25:28-30) and are readily available e.g.

In a particularly preferred embodiment the methods allow a user to characterize a gene of a cell or organism by identifying a biological function associated with that gene or, more precisely, with its gene product. In such a preferred embodiment, the modified biological sample can be, e.g., a "knock out" or mutant cell or organism in which the gene of interest has been deleted from the chromosome or has been mutated such that it no longer encodes a functional gene product. The response profile of this modified biological sample is then compared to response profiles of other modified biological samples, in particular response profiles for cells in which other genes have been "knocked out" or mutated. Response profiles are then identified that have similar or common "response motifs" to the response profile for the gene of interest. In general, these response motifs are associated with a particular biological effect or biological function. Thus, the gene of interest is characterized as having the biological function associated with the common response motifs. Response profiles that do not have similar or common "response motifs" to the response profile for the gene of interest are also useful, since these "negative" results indicate that the gene of interest does not have that particular biological effect or biological function.

Figure 1:
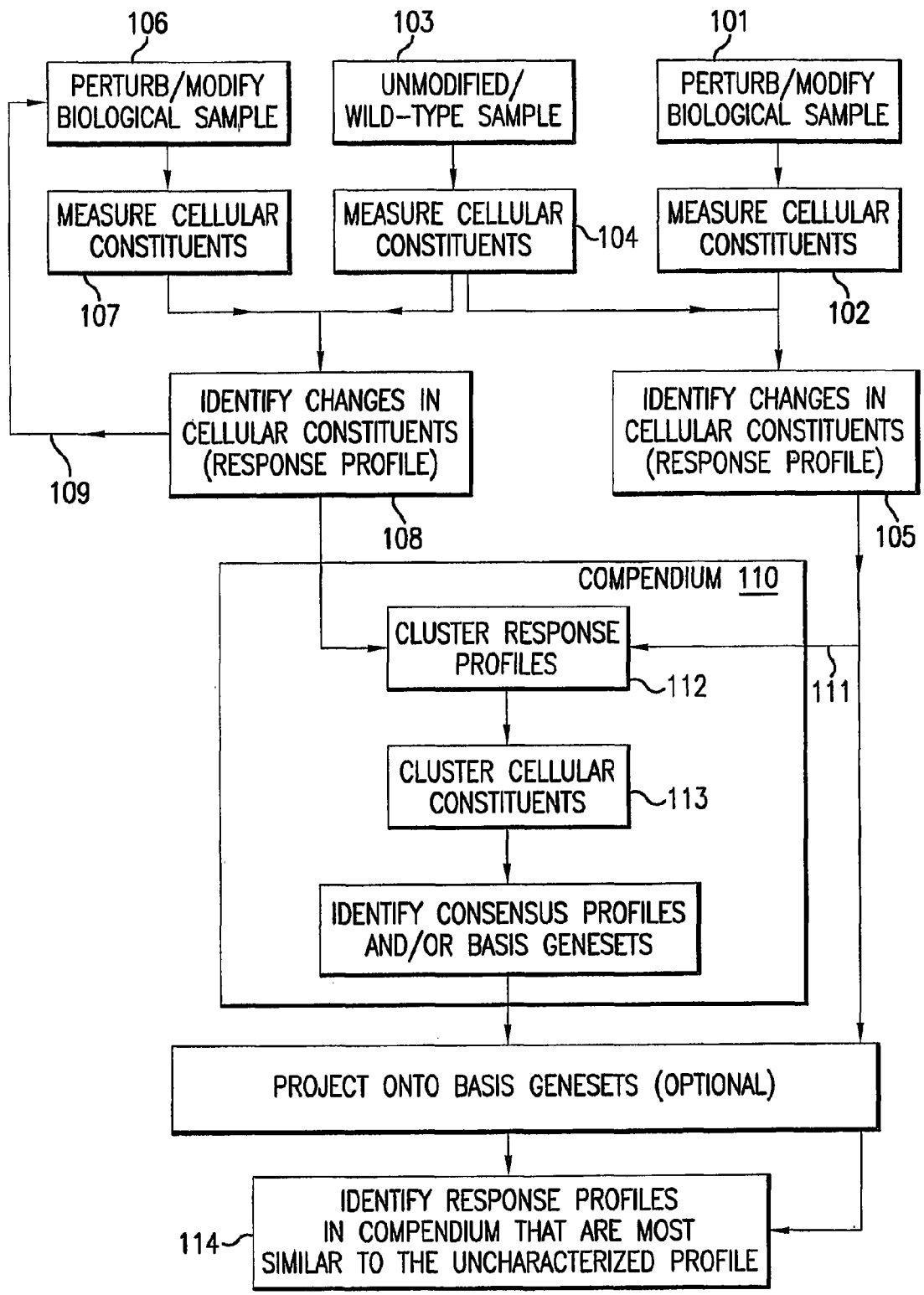
FIG. 1 shows a flow chart diagram illustrating a detailed exemplary embodiment of the methods of the invention.

A flow chart illustrating the steps of a more detailed, exemplary embodiment of the invention is shown in FIG. 1 with particular reference to a specific embodiment in which the biological function of an uncharacterized gene is determined. In step 101, a biological sample is perturbed or modified by modifying the particular cellular constituent (in this case the particular gene) to be characterized. A plurality of the cellular constituents of the modified biological sample is measured (102). Such measurements can include, for example, measurements of abundances for a plurality of mRNA species encoded by a plurality of different genes, e.g., by measuring abundances cDNA species reverse transcribed from mRNA extracted from the biological sample or by measuring abundances of cRNA species produced from said cDNA. A plurality of cellular constituents is also measured for an unmodified biological sample (104). For example, in the specific embodiment depicted in FIG. 1 wherein the modification is a modification or mutation to a specific gene, the unmodified biological sample may be a sample from a "wild-type" cell or organism. The measurements of cellular constituents from the modified and unmodified biological samples are compared (105) and those cellular constituents whose abundances or activities change from the unmodified to the modified cell are identified, thus giving a response profile for the cellular constituent (e.g., gene) to be characterized, denoted $v^{(x)}$ in FIG. 1.

The response profile $v^{(x)}$ for the uncharacterized gene is subsequently compared to a plurality of other response profiles, denoted $v^{(m)}$ in FIG. 1, corresponding to a plurality of other modifications to the biological sample. In particular, the response profile for the uncharacterized gene is most preferably compared to a "compendium" or database of response profiles (110). Such a database can be obtained, as depicted in FIG. 1, by measuring cellular constituents from a plurality of other modified samples (107) in which other cellular constituents (e.g., other genes in FIG. 1) have been modified or perturbed and comparing (108) these measurements to the measurements of cellular constituents of the unmodified or wild-type biological sample. The response profile $v^{(m)}$ is then added to the compendium, and the steps of perturbing the biological sample (106), measuring cellular constituents (107) and comparing to measurements from unmodified cells (108) is repeated so that a plurality of response profiles is obtained. This is the plurality of response profiles from the compendium of response profiles to which the profile $v^{(x)}$ of the uncharacterized cellular constituent (e.g., the uncharacterized gene in FIG. 1) is compared.

In preferred embodiments of the invention, the response profile for the uncharacterized gene $v^{(x)}$ is also added to the compendium (111). The response profiles of the compendium are then preferably grouped or "clustered" (112) according to the methods of the invention so that response profiles corresponding to a particular biological effect are organized in a common group or "cluster" of response profiles. Although not necessary in order to practice the methods of the invention, the individual cellular constituents that are measured in each response profile of the compendium can also be grouped or "clustered" (113) so that measured cellular constituents that tend to co-vary in the different response profiles are grouped in a common "cluster" of measured cellular constituents. It is noted that, although FIG. 1 specifically depicts performing the step of clustering response profiles (112) before the step of clustering measured cellular constituents (113), these steps can, in fact, be performed in any order. The results of Steps 112 and 113 can be used to define co-varying basis genesets and also consensus profiles, as discussed in Section 5.2.4. Optionally, both the compendium reference profiles and the uncharacterized profile may be projected onto basis genesets to allow a more robust comparison.

Finally, response profiles most similar to the response profile for the uncharacterized cellular constituent are identified (114). Generally, at least some of these response profiles will be associated with a particular biological effect. In particular, at least some, and preferably all, of the response profiles in the cluster will be from perturbations or modifications of cellular constituents that have a common, known biological effect or a known biological function. The biological function of the cellular constituent to be characterized in therefore identified as being the common biological function associated with the other response profiles of the cluster.

As one skilled in the art will readily appreciate, the methods of the present invention, although described herein primarily as methods for identifying the biological function of cellular constituents (i.e., of genes and gene products) are also readily adaptable to characterizing drugs. Specifically, the methods and systems of the present invention can also be used to identify the biological function or functions that are affected by a drug or a drug combination and, further, can even identify one or more drug targets.

For example, Section 6.4.2 below describes particular, exemplary experiments wherein a previously unknown target, Erg2p, is identified for the drug dyclonine according to the methods of this invention. In such embodiments, a response profile is obtained for the drug or drug combination to be characterized by exposing a biological sample to one or more dosages of the drug or drug combination and measuring changes in, e.g., activities or abundances, of cellular constituents relative to an untreated biological sample. By clustering this response profile with other response profiles, e.g., from a compendium of the present invention, biological function effected by the drug or drug combination can be identified. Further, the response profile of the drug or drug combination will correlate most closely with the response profile from a modification or perturbation to the target of the drug or drug combination. For example, in Section 6.4.2 it is shown that the response profile for treatment with dyclonine correlates most closely with the response profile obtained from a cell line in which the erg2p gene has been "knocked out." Thus, the gene product of this gene (i.e., Erg2p) is identified as the target of dyclonine.

5.2.2. Alternative Embodiments

This subsection describes alternative embodiments relating to the use of compendia for characterizing the biological functions associated with cellular constituents and genes.

In one alternative embodiment, the biological function with which a cellular constituent of a cell type or organism is associated can be determined. A first step comprises determining measured amounts of a plurality of cellular constituents in a first cell of said cell type or said type of organism in which the cellular constituent to be characterized is perturbed to create a first response profile.

In a second step, the first response profile is compared to a database comprising landmark response profiles to determine the one or more landmark response profiles that are most similar to the first profile, wherein each landmark profile comprises measured amounts of a plurality of cellular constituents in a second cell of said cell type or organism having a perturbation in a cellular constituent associated with a known biological function. The known biological function of the cellular constituent perturbed in the landmark response profile that is determined to be most similar to the first profile is the biological function with which the cellular constituent to be characterized is associated. Conversely, if the first response profile is found not to be similar to one or more landmark response profiles in which a cellular constituent with a known biological function is perturbed, then the cellular constituent to be characterized does is not associated with that known biological function.

In a second alternative embodiment, the characterization of the biological function of a cellular constituent can be carried out simply by comparing a first response profile or a predicted profile created from a cell of a cell type or organism in which the cellular constituent is perturbed to a database comprising landmark response profiles to determine the one or more landmark response profiles that are most similar to the first profile, wherein each landmark response profile is associated with a perturbation of a cellular constituent having a known biological function. Thus, if a first response profile has previously been obtained, then the step of measuring cellular constituents to obtain the first response profile can be skipped.

In a third alternative embodiment, a cellular constituent, and particularly a gene, can be characterized as being associated with a particular biological function. A first step comprises determining measured amounts of a plurality of cellular constituents in a cell of a cell type or type of organism in which the gene being characterized, or its gene transcript, is perturbed or modified to create a first response profile.

A second step comprises clustering a plurality of response profiles, including the first response profile and a plurality of landmark response profiles associated with a perturbation or modification of a gene, or its gene transcript, having a known biological function.

A third step comprises identifying the landmark response profile in the plurality of landmark response profiles that cluster with the first response profile for the gene being characterized. The biological function of the gene or gene transcript perturbed in this landmark response profile is the function associated with the gene being characterized. Conversely, the biological function of a gene or gene transcript perturbed in a landmark response profile that does not cluster with the first response profile is not the biological function with which the gene being characterized is associated.

In a fourth alternative embodiment, the characterization of the biological function of a cellular constituent can be carried out simply by comparing a first response profile or a predicted profile created from a cell of a cell type or organism in which the cellular constituent is perturbed to a database comprising landmark response profiles to determine the one or more landmark response profiles that are most similar to the first response profile, wherein each landmark response profile is associated with a perturbation of a cellular constituent having a known biological function.

The predicted profile may be for different cellular constituents than those for which amounts were measured in the experiment. For example, a translational profile of protein levels may be used to predict the corresponding transcript profile, which may be used for comparison to a database comprising landmark transcript profiles. Alternatively, an expression profile of an immature organism may be acquired and may be used to predict an expression profile of the mature organism.

In one embodiment, the measured amounts of the pluralities of cellular constituents are determined in comparison to a wild-type cell. Alternatively, the measured amounts of the pluralities of cellular constituents are absolute amounts of the pluralities of cellular constituents, e.g., the number of mRNA molecules per cell.

5.2.3. Compendium of Modified Cell Perturbation Patterns

In preferred embodiments, the present invention is practiced using a database or "compendium" of biological response profiles (landmark response profiles). In particular, the compendium used in the systems and methods of the present invention is most preferably a compendium of modified-cell perturbation patterns. In a particularly preferred embodiment, the modified-cell perturbation patterns are perturbation response profiles from genetic modifications to cells or an organism. The genetic modifications can include any of the genetic modifications described, below, in Section 5.4.1, including targeted deletions, disruptions or over-expression of specific genes.

In other embodiments, the compendium can be a compendium of response profiles from other modifications or perturbations to cells or an organism, including any of the modifications and perturbations described in Section 5.4 below. For example, the compendium can be a compendium of perturbation response profiles from modifications or perturbations to RNA abundances, RNA activities, protein abundances or protein activities. The compendium can also be a compendium of perturbation response profiles from treating cells or an organism with particular drugs; most preferably well characterized drugs that have a specific, known mechanism of action (i.e., drugs having a known, specific target). The compendium can also be a compendium comprising mixtures of any two or more of the above-described modifications and perturbations. In particular, the compendium can comprise any mixture of perturbation response profiles from any of the modifications or perturbations described herein and, in particular, in Section 5.4 below.

The compendium preferably comprises a plurality of perturbation response profiles. In particular, the compendium preferably comprises response profiles corresponding to perturbations to a substantial fraction of the cellular constituents of a cell or organism. For example, in embodiments, wherein the compendium is a compendium of profiles from genetically modified cells or organisms, the compendium preferably includes response profiles from genetic modifications to at least 2% of the genes of the cell or organism. More preferably, the compendium includes response profiles from genetic modifications to at least 5%, still more preferably at least 15%, still more preferably at least 30%, still more preferably at least 40%, most preferably 75% of the genes of the cell or organism. In one embodiment, wherein the cell or organism is a cell or organism, such as *Saccharomyces cerevisiae*, for which the sequence of the entire genome has been determined or substantially determined, the compendium most preferably comprises response profiles from genetic modifications to all or substantially all of the genes of the cell or organism.

A "gene" is identified as the portion of DNA that is transcribed by RNA polymerase. Thus, a gene may include a 5.' untranslated region ("UTR"), introns, exons and a 3' UTR. A gene preferably comprises at least 150, 225, or 297 nucleotides from which a messenger RNA is transcribed in the organism or in some cell in a multicellular organism. It is noted that the sequence of the entire genome of a cell or organism of interest need not have been determined to practice the methods of the present invention. Thus, although only a fraction of the genes in a genome have been completely sequenced, the methods of the present invention can be practiced using a compendium of response profiles corresponding to perturbations of only these genes. Further, the number of genes for which partial sequences, such as ESTs are available, is much higher. As the skilled artisan readily appreciates, the modification and perturbation methods described below in Section 5.4 can be readily practiced using target genes, RNAs or proteins for which only the partial sequence, such as an EST sequence, is known.

As noted, in Section 5.1.2 above, the biological response to a perturbation m can be represented as the vector $v^{(m)}$ whose individual elements $v_i^{(m)}$ are the amplitude of the response of each cellular constituent i to the perturbation m (e.g., the logarithm of the ratio of the abundance or activity of cellular constituent i when the cell is subject to perturbation m to when the cell is not subject to perturbation m). Accordingly, the perturbation response profiles in a compendium of the present invention are most preferably obtained or measured under identical or at least substantially identical conditions that differ only by the particular perturbation of the response profile. In other words, the unperturbed or reference state of each perturbation response profile in the compendium is preferably identical for all of the perturbation response profiles. Likewise, the perturbed state of each perturbation response profile should differ from the unperturbed state by the specific perturbation of the perturbation response profile (e.g., the specific genetic mutation, the specific drug exposure, or the specific change in nutrient or other growth conditions).

For example, the perturbation response profiles are most preferably obtained for identical cell types. More specifically, the cells are preferably isogenic cells, or at least substantially isogenic cells, that are obtained from the same species of organism, and more preferably from the same tissue or same tissue type of that species of organism. The perturbation response profiles are also preferably obtained or measured from cells that are at the same stage of growth (i.e., cells that are in the same phase of the cell cycle). In embodiments, wherein the cells are cells from a multicellular organism such as a plant or an animal, the cells are preferably obtained from one or more individual organisms during the same developmental stage (e.g., cells from an embryonic organism or, alternatively, from an adult organism). The response profiles are also preferably obtained from cells grown under identical conditions; such as identical conditions of temperature and nutrient content. It is further noted that, although each perturbation will most preferably consist of a single change to a cell (e.g., mutation of only a single gene, exposure of the cell to only a single drug), perturbations that comprise more than one change to the cell are also contemplated (e.g., mutation of one or more genes and exposure of the cells to a particular drug).

In a preferred embodiment, expression profiles in a compendium of the present invention are obtained under conditions that inhibit growth of the perturbed cells. This is because perturbation response profiles are typically strongest (i.e., the absolute amplitudes of the cellular constituents' responses to the perturbations are largest) when the conditions are conditions under which the perturbed cell grows poorly or has a reduced growth rate. For instance, the Example presented in Section 6.2, below, demonstrates that in a particular embodiment, wherein the perturbations comprise mutations to individual genes of the yeast *S. cerevisiae*, those mutants that have reduced growth rates under the conditions used in these experiments are the mutants having the strongest expression profiles. That is to say, amplitudes of expression levels for measured cellular constituents (specifically, for different genetic transcripts) in these mutants are most different from the unperturbed or wild-type cells. Likewise, the expression profiles of mutants that did not show substantially lower growth rates under conditions used in these experiments have expression profiles that are relatively similar to the expression profiles of unperturbed or wild-type cells.

The Examples presented in Sections 6.4.4 and 6.4.5 below demonstrate, however, that useful information, e.g., characterizing the biological function of uncharacterized genes or gene products, can be obtained even when changes of individual cellular constituents in a perturbation response profile are low-amplitude. Thus, it is merely preferable, but not essential, that perturbation experiments be performed under conditions wherein the perturbation(s) inhibit cell growth.

Further, the methods and systems of the present invention can also employ a plurality of compendia, rather than only a single compendium, of perturbation response profiles. For example, it is possible, using the methods and compositions of the present invention, to generate a plurality of "parallel" compendia encompassing a plurality of different growth conditions. Each of the compendia would then comprise perturbations response profiles for the same perturbations but under different baseline or unperturbed conditions (most preferably different conditions of cell growth). For example, the "parallel" compendia might encompass different nutrient conditions, different conditions of temperature, different stages of cell growth, different cell types (e.g., cells from different tissues of the same species of organism) or corresponding to different stages of development.

The cellular constituents in a compendium of the present invention are preferably organized or ordered according to "co-varying sets" as described below in Section 5.2.4. Further, the response profiles of the compendium are also preferably ordered or "clustered" according to methods such as the methods described below in Section 5.2.5. It is further noted that the invention also contemplates "dynamic" databases or compendia of perturbation response profiles. In particular, the compendia of the invention can be continuously updated as additional modifications and perturbation experiments are performed so that the new perturbation response profiles are added to the database.

Figure 2:
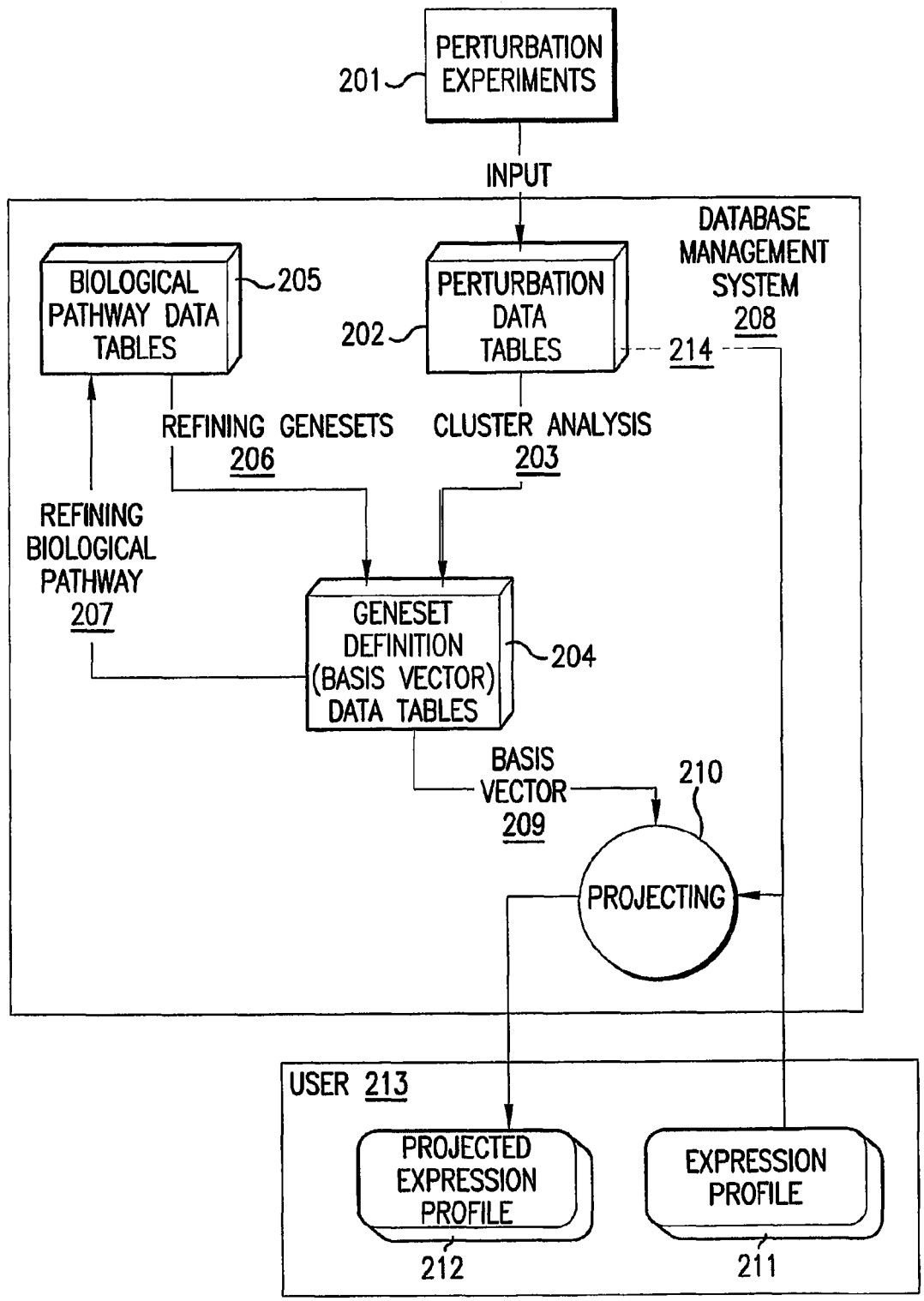
FIG. 2 illustrates and exemplary compendium database management system.

An exemplary illustration of such a dynamic database is shown in FIG. 2. Although for simplicity this database is described as a database of genesets, the description is equally applicable to databases of other sets of cellular constituents. In the exemplary embodiment shown in FIG. 2, data from perturbation experiments (201) are input into data tables (202) in the database management system (208). Geneset definitions, e.g., in the form of basis vectors, are continuously generated (203) based upon the updated data in the perturbation database and using the cluster analysis techniques described in Section 5.2.4 below. The geneset definitions can be further refined (206) using a database of biological pathway definitions (206). The resulting geneset definition datatable (204) thus contains updated definitions for genesets.

The geneset definitions are used, in turn, to refine (207) the biological pathway datatables (206). The geneset definition tables are accessible by user-submitted projection requests. In particular, a user (213) can access the database management system by submitting expression profiles (211). The database management system projects (210) the expression profile into a projected expression profile (see, in particular, Section 5.2.6 for a description of this process). The user-submitted expression profile is optionally added to the perturbation datatable (202).

The dynamic database is constantly productive in the sense that it provides useful geneset definitions with the first, and limited, set of perturbation data. The dynamically updated database continuously refines its geneset definitions to provide more useful geneset definitions as more perturbation data become available.

In some embodiments of the dynamic geneset definition database, the perturbation data and geneset definition data are stored in a series of relational tables in digital computer storage media (e.g., on one or more hard drives, CD-ROMs, floppy disks or DAT tapes to name a few). Preferably, the database is implemented in distributed system environments with client/server implementation, allowing multiuser and remote access. Access control and usage accounting are implemented in some embodiments of the database system. Relational database management systems and client/server environments are well documented in the art (see, for example, Nath, 1995, *The Guide to SQL Server*, 2nd Ed., Addison-Wesley Publishing Co.).

5.2.4. Determining Co-Varying Sets

The methods of the present invention involve arranging or grouping cellular constituents in the response profiles according to their tendency to co-vary in response to a perturbation. In particular, this Section describes specific embodiments for arranging the cellular constituents into co-varying sets.

Clustering Algorithms:

Preferably, the basis or co-varying sets of the present invention are identified by means of a clustering algorithm (i.e., by means of "clustering analysis"). Clustering algorithms of this invention may be generally classified as "model-based" or "model-independent" algorithms. In particular, model-based clustering methods assume that co-varying sets or clusters map to some predefined distribution shape in the cellular constituent "vector space." For example, many model-based clustering algorithms assume ellipsoidal cluster distributions having a particular eccentricity. By contrast, model-independent clustering algorithms make no assumptions about cluster shape. As is recognized by those skilled in the art, such model-independent methods are substantially identical to assuming "hyperspherical" cluster distributions. Hyperspherical cluster distributions are generally preferred in the methods of this invention, e.g., when the perturbation vector elements $v_i^{(m)}$ have similar scales and meanings, such as the abundances of different mRNA species.

The clustering methods and algorithms of the present invention may be further classified as "hierarchical" or "fixed-number-of groups" algorithms (see, e.g., S-Plus Guide to Statistical and Mathematical Analysis v. 3.3, 1995, MathSoft, Inc.: StatSci. Division, Seattle, Wash.). Such algorithms are well known in the art (see, e.g., Fukunaga, 1990, *Statistical Pattern Recognition*, 2nd Ed., San Diego: Academic Press; Everitt, 1974, *Cluster Analysis*, London: Heinemann Educ. Books; Hartigan, 1975, *Clustering Algorithms*, New York: Wiley; Sneath and Sokal, 1973, *Numerical Taxonomy*, Freeman; Anderberg, 1973, *Cluster Analysis for Applications*, New York: Academic Press), and include, e.g., hierarchical agglomerative clustering algorithms, the "k-means" algorithm of Hartigan (supra), and model-based clustering algorithms such as mclust by MathSoft, Inc. Preferably, hierarchical clustering methods and/or algorithms are employed in the methods of this invention. In a particularly preferred embodiment, the clustering analysis of the present invention is done using the hclust routine or algorithm (see, e.g., 'hclust' routine from the software package S-Plus, MathSoft, Inc., Cambridge, Mass.).

The clustering algorithms used in the present invention operate on a table of data containing measurements of a plurality of cellular constituents, preferably gene expression measurements, such as those described in Section 5.2.3 above. Specifically, the data table analyzed by the clustering methods of the present invention comprise an N×K array or matrix wherein N is the total number of conditions or perturbations and K is the number of cellular constituents measured or analyzed.

The clustering algorithms of the present invention analyze such arrays or matrices to determine dissimilarities between cellular constituents. Mathematically, dissimilarities between cellular constituents i and j are expressed as "distances" $I_{ij}$. For example, in one embodiment, the Euclidian distance is determined according to the Equation 6:

$$I_{i,j} = \left(\sum_m |v_i^{(m)} - v_j^{(m)}|^2\right)^{1/2} \quad \text{(Equation 6)}$$

In Equation 6, above, $v_i^{(m)}$ and $v_j^{(m)}$ are the responses of cellular constituent i and j, respectively, to the perturbation m. In other embodiments, the Euclidian distance in Equation 6, above, is squared to place progressively greater weight on cellular constituents that are further apart. In alternative embodiments, the distance measure $I_{ij}$ is the Manhattan distance provided by Equation 7:

$$I_{i,j} = \sum_m |v_i^{(m)} - v_j^{(m)}| \quad \text{(Equation 7)}$$

In embodiments wherein the response profile data is categorical (e.g., wherein each element $v_i^{(m)} = 1$ or 0), the distance measure is preferably a percent disagreement defined by Equation 8:

$$I_{i,j} = \frac{\text{No. of } v_i^{(m)} \neq v_j^{(m)}}{N} \quad \text{(Equation 8)}$$

In a particularly preferred embodiment, the distance is defined as $I_{ij} = 1 - r_{ij}$, where $r_{ij}$ is the "correlation coefficient" or normalized "dot product" between the response vectors $v_i$ and $v_j$. In particular, $r_{ij}$ is defined by Equation 9, below:

$$r_{i,j} = \frac{v_i \cdot v_j}{|v_i||v_j|} \quad \text{(Equation 9)}$$

In Equation 9, the dot product $v_i \cdot v_j$ is defined according to Equation 10:

$$v_i \cdot v_j = \sum_m (v_i^{(m)} \times v_j^{(m)}) \quad \text{(Equation 10)}$$

Further, the quantities $|v_i|$ and $|v_j|$ in Equation 9 are provided by the relations $|v_i| = (v_i \cdot v_j)^{1/2}$, and $|v_j| = (v_j \cdot v_j)^{1/2}$.

In still other embodiments, the distance measure can some other distance measure known in the art, such as the Chebychev distance, the power distance, and percent disagreement, to name a few. Most preferably, the distance measure is appropriate to the biological questions being asked, e.g., for identifying co-varying and/or co-regulated cellular constituents including co-varying or co-regulated genes. For example, in a particularly preferred embodiment, the distance measure $I_{ij} = 1 - r_{ij}$ with the correlation coefficient which comprises a weighted dot product of the response vectors $v_i$ and $v_j$. Specifically, in this preferred embodiment, $r_{ij}$ is preferably defined by Equation 11:

$$r_{i,j} = \frac{\sum_m \frac{v_i^{(m)} v_j^{(m)}}{\sigma_i^{(m)} \sigma_j^{(m)}}}{\left[\sum_m \left(\frac{v_i^{(m)}}{\sigma_i^{(m)}}\right)^2 \sum_m \left(\frac{v_j^{(m)}}{\sigma_j^{(m)}}\right)^2\right]^{1/2}} \quad \text{(Equation 11)}$$

In Equation 11, above, the quantities $\sigma_i^{(m)}$ and $\sigma_j^{(m)}$ are the standard errors associated with the measurement of the i'th and j'th cellular constituents, respectively, in experiment m.

The correlation coefficients provided by Equations 9 and 11 are bounded between values of +1, which indicates that the two response vectors are perfectly correlated and essentially identical, and −1, which indicates that the two response vectors are "anti-correlated" or "anti-sense" (i.e., are opposites). These correlation coefficients are particularly preferably in embodiments of the invention where cellular constituent sets or clusters are sought of constituents which have responses of the same sign. However, in other embodiments, it can be preferable to identify cellular constituent sets or clusters which are co-regulated or involved in the same biological responses or pathways but comprise both similar and anti-correlated responses. In such embodiments, it is preferable to use the absolute value of the correlation coefficient provided by Equation 9 or 11; i.e., $|r_{ij}|$ as the correlation coefficient.

In still other embodiments, the relationships between co-regulated and/or co-varying cellular constituents may be even more complex, such as in instances wherein multiple biological pathways (for example, multiple signaling pathways) converge on the same cellular constituent to produce different outcomes. In such embodiments, it is preferable to use a correlation coefficient $r_{ij} = r_{ij}^{(change)}$ which is capable of identifying co-varying and/or co-regulated cellular constituents irrespective of the sign. The correlation coefficient specified by Equation 12, below, is particular useful in such embodiments.

$$r_{i,j}^{(change)} = \frac{\sum_m \left|\frac{v_i^{(m)}}{\sigma_i^{(m)}}\right| \left|\frac{v_j^{(m)}}{\sigma_j^{(m)}}\right|}{\left[\sum_m \left(\frac{v_i^{(m)}}{\sigma_i^{(m)}}\right)^2 \sum_m \left(\frac{v_j^{(m)}}{\sigma_j^{(m)}}\right)^2\right]^{1/2}} \quad \text{(Equation 12)}$$

Generally, the clustering algorithms used in the methods of the invention also use one or more linkage rules to group cellular constituents into one or more sets or "clusters." For example, single linkage or the nearest neighbor method determines the distance between the two closest objects (i.e., between the two closest cellular constituents) in a data table. By contrast, complete linkage methods determine the greatest distance between any two objects (i.e., cellular constituents) in different clusters or sets. Alternatively, the unweighted pair-group average evaluates the "distance" between two clusters or sets by determining the average distance between all pairs of objects (i.e., cellular constituents) in the two clusters. Alternatively, the weighted pair-group average evaluates the distance between two clusters or sets by determining the weighted average distance between all pairs of objects in the two clusters, wherein the weighing factor is proportional to the size of the respective clusters. Other linkage rules, such as the unweighted and weighted pair-group centroid and Ward's method, are also useful for certain embodiments of the present invention (see, e.g., Ward, 1963, *J. Am. Stat. Assn* 58:236; Hartigan, 1975, *Clustering Algorithms*, New York: Wiley).

In particularly preferred embodiments, an agglomerative hierarchical clustering algorithm is used. Such algorithms are known in the art and described, e.g., in Hartigan, supra. Briefly, the algorithm preferably starts with each object (e.g., each cellular constituent) as a separate group. In each successive step, the algorithm identified the two most similar objects by finding the minimum of all the pair-wise similarity measures, merges them into one object (i.e., into one "cluster") and updates the between-cluster similarity measures accordingly. The procedure continues until all objects are found in a single group. When merging two closest objects, a heuristic criterion of average linkage is preferably employed to redefine the between-cluster similarity measures. Since two objects are combined at each similarity level, such a clustering algorithm clustering yields a rigid hierarchical structure among objects and defines their memberships.

Figure 3:
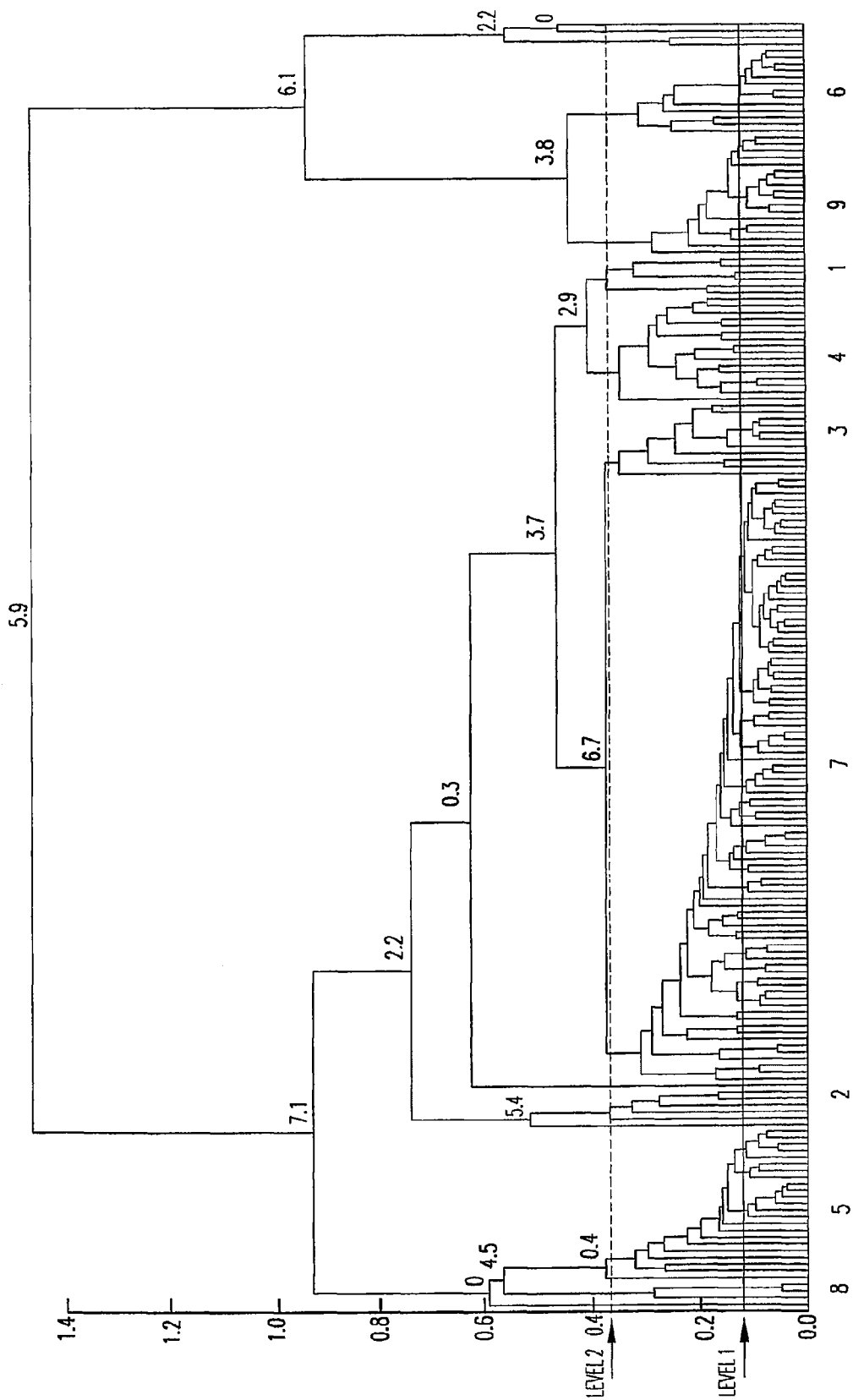
FIG. 3 is an exemplary clustering tree, obtained by the hclust clustering algorithm from 34 experiments (depicted in FIGS. 5 and 6).

Once a clustering algorithm has grouped the cellular constituents from the data table into sets or clusters, e.g., by application of linkage rules such as those described supra, a clustering "tree" may be generated to illustrate the clusters of cellular constituents so determined. FIG. 3 illustrates an exemplary clustering tree generated by the hclust clustering algorithm upon analysis of the 34×185 table of response profile data illustrated in FIG. 3, and using the distance metric $I_{ij}=1-r_{ij}$. The measured response data $\{v_i^{(m)}\}$ comprise the logarithm to the base 10 of the ratio between abundances of each transcript i in the pair of conditions (i.e., perturbation and no perturbation) comprising each differential experiment m.

Genesets may be readily defined based on the branchings of a clustering tree such as the one illustrated in FIG. 3. In particular, genesets may be defined based on the many smaller branchings of a clustering tree, (e.g., at LEVEL 1 indicated in FIG. 3), or, optionally, larger genesets may be defined corresponding to the larger branches of a clustering tree (e.g., at LEVEL 2 in FIG. 3). Preferably, the choice of branching level at which genesets are defined matches the number of distinct response pathways expected. In embodiments wherein little or no information is available to indicate the number of pathways, the genesets should be defined according to the branching level wherein the branches of the clustering tree are "truly distinct."

"Truly distinct," as used herein, may be defined, e.g., by a minimum distance value between the individual branches. For example, in FIG. 3 the distance between truly distinct genesets is the vertical coordinate of the horizontal connector joining two branches. Typically, the distance values between truly distinct genesets are in the range of 0.2 to 0.4, where a distance of zero corresponds to perfect correlation and a distance of unity corresponds to no correlation. However, distances between truly distinct genesets may be larger in certain embodiments, e.g., wherein there is poorer quality data or fewer experiments n in the response profile data. Alternatively, in other embodiments, e.g., having better quality data or more experiments n in the profile dataset, the distance between truly distinct genesets may be less than 0.2.

For example, if the horizontal cut indicated by the dotted line in FIG. 3 is used, and only those branches having two or more cellular constituents below the cut are accepted as genesets, nine genesets are obtained. These nine genesets in fact reflect pathways involving the calcineurin protein, the PDR gene, the Gcn4 transcription factor, RNR (a DNA repair gene), and cellular stress responses. Thus, the genesets identified in FIG. 3, and genesets identified by cluster analysis in general, have an underlying biological significance.

Statistical Significance:

Preferably, truly distinct cellular constituent sets are defined by means of an objective test of statistical significance for each bifurcation in the clustering tree. For example, in one aspect of the invention, truly distinct cellular constituent sets are defined by means of a statistical test which uses Monte Carlo randomization of the experiment index m for the responses of each cellular constituent across the set of experiments. For example, in one preferred embodiment, the experiment index m of each cellular constituent's response $v_i^{(m)}$ is randomly permutated, as indicated by Equation 13:

$$v_i^{(m)} \rightarrow v_i^{\Pi(m)} \quad \text{(Equation 13)}$$

More specifically, a large number of permutations of the experiment index m is generated for each cellular constituent's response. Preferably, the number of permutations is from 50 to about 1000, more preferably from 50 to about 100. For each branching of the original clustering tree, and for each permutation of the experiment index:

(1) hierarchical clustering is performed on the permutated data, preferably using the same clustering algorithm as used for the original unpermuted data (e.g., hclust for the clustering tree in FIG. 3); and (2) the fractional improvement f in the total scatter is computed with respect to the cluster centers in going from one cluster to two clusters.

In particular, the fractional improvement f is computed according to Equation 14, below:

$$f = 1 - \frac{\sum D_i^{(1)}}{\sum D_i^{(2)}} \quad \text{(Equation 14)}$$

In Equation 14, $D_i$ is the square of the distance measure for cellular constituent i with respect to the center (i.e., the mean) of its assigned cluster. The superscripts (1) and (2) indicate whether the square of the distance measure D, is made with respect to (1) the center of its entire branch, or (2) the center of the appropriate cluster out of the two clusters. The distance function $D_i$ in Equation 14 may be defined according to any one of several embodiments. In particular, the various embodiments described supra for the definition of $I_{ij}$ may also be used to define $D_i$ in Equation 14.

The distribution of fractional improvements obtained from the above-described Monte Carlo methods provides an estimate of the distribution under the null hypothesis, i.e., the hypothesis that a particular branching in a cluster tree is not significant or distinct. A significance can thus be assigned to the actual fractional improvement (i.e., the fraction improvement of the unpermuted data) by comparing the actual fractional improvement to the distribution of fractional improvements for the permuted data. Preferably, the significance is expressed in terms of the standard deviation of the null hypothesis distribution, e.g., by fitting a log normal model to the null hypothesis distribution obtained from the permuted data. For example, the numbers displayed at the bifurcations in FIG. 3 are the significance, in multiples of the standard deviation of the null hypothesis distribution, of each bifurcation. Numbers greater than about 2, for example, indicate that the branching is significant at the 95% confidence level.

In more detail, an objective statistical test is preferably employed to determine the statistical reliability of the grouping decisions of any clustering method or algorithm. Preferably, a similar test is used for both hierarchical and non-hierarchical clustering methods. More preferably, the statistical test employed comprises (a) obtaining a measure of the compactness of the clusters determined by one of the clustering methods of this invention, and (b) comparing the obtained measure of compactness to a hypothetical measure of compactness of cellular constituents regrouped in an increased number of clusters. For example, in embodiments wherein hierarchical clustering algorithms, such as hclust, are employed, such a hypothetical measure of compactness preferably comprises the measure of compactness for clusters selected at the next lowest branch in a clustering tree (e.g., at LEVEL 1 rather than at LEVEL 2 in FIG. 3). Alternatively, in embodiments wherein non-hierarchical clustering methods or algorithms are employed, e.g., to generate N clusters, the hypothetical measure of compactness is preferably the compactness obtained for N+1 clusters by the same methods.

Cluster compactness may be quantitatively defined, e.g., as the mean squared distance of elements of the cluster from the "cluster mean," or, more preferably, as the inverse of the mean squared distance of elements from the cluster mean. The cluster mean of a particular cluster is generally defined as the mean of the response vectors of all elements in the cluster. However, in certain embodiments, e.g., wherein the absolute value of Equation 9 or 11 is used to evaluate the distance metric (i.e., $I_{ij}=1-|r_{ij}|$) of the clustering algorithm, such a definition of cluster mean is problematic. More generally, the above definition of mean is problematic in embodiments wherein response vectors can be in opposite directions such that the above defined cluster mean could be zero. Accordingly, in such embodiments, it is preferable to chose a different definition of cluster compactness such as, but not limited to, the mean squared distance between all pairs of elements in the cluster. Alternatively, the cluster compactness may be defined to comprise the average distance (or more preferably the inverse of the average distance) from each element (e.g., cellular constituent) of the cluster to all other elements in that cluster.

Preferably, step (b) above of comparing cluster compactness to a hypothetical compactness comprises generating a non-parametric statistical distribution for the changed compactness in an increased number of clusters. More preferably, such a distribution is generated using a model which mimics the actual data but has no intrinsic clustered structures (i.e., a "null hypothesis" model). For example, such distributions may be generated by (a) randomizing the perturbation experiment index m for each actual perturbation vector $v_i^{(m)}$, and (b) calculating the change in compactness which occurs for each distribution, e.g., by increasing the number of clusters from N to N+1 (non-hierarchical clustering methods), or by increasing the branching level at which clusters are defined (hierarchical methods).

Figure 4:
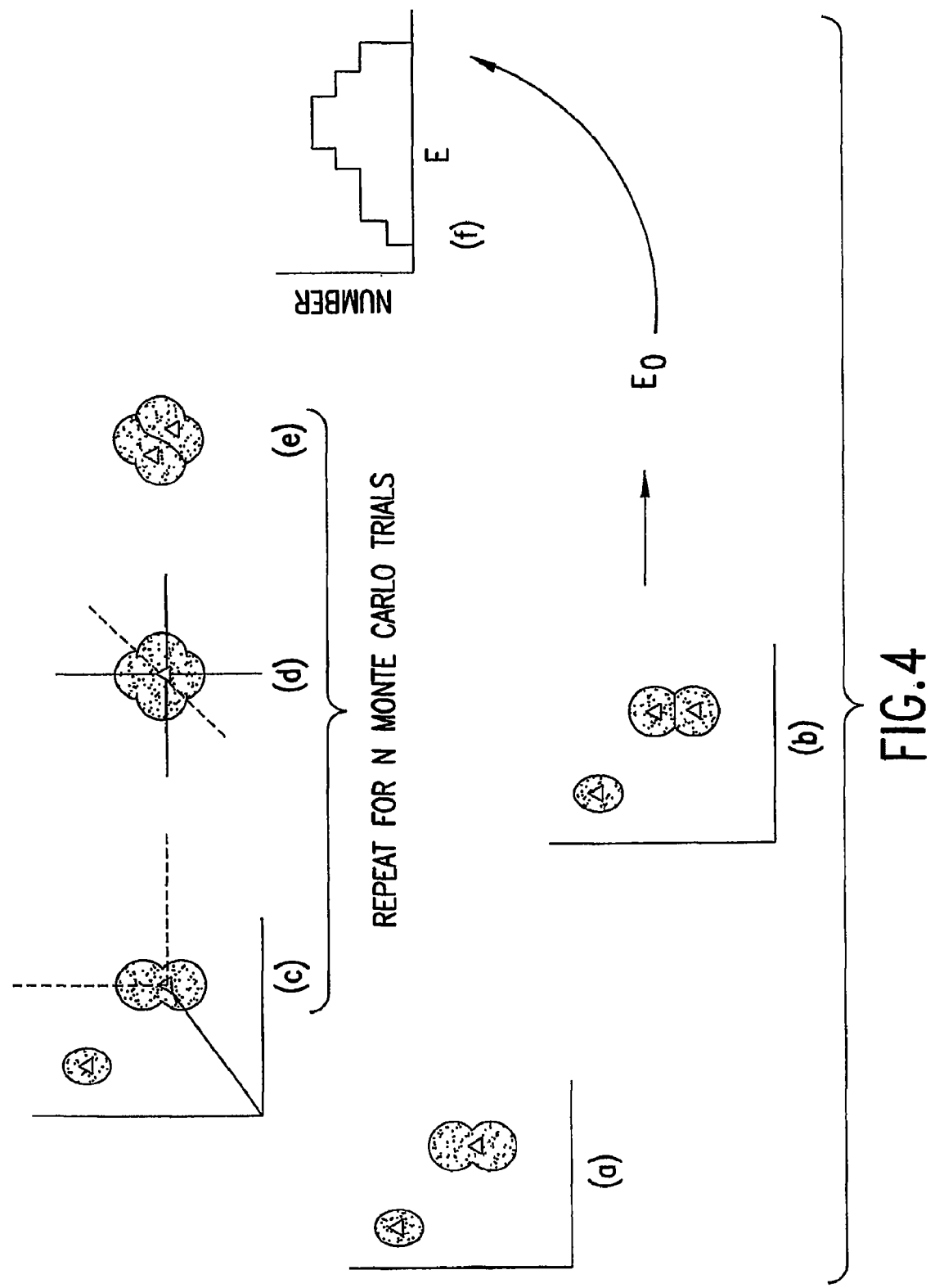
FIG. 4 illustrates an exemplary, two-dimensional embodiment of the Monte Carlo method for assigning significance to cluster subdivisions.

Such a process is illustrated in FIG. 4 for an exemplary, non-hierarchical embodiment of the clustering methods wherein the response vectors are two-dimensional (i.e., there are two perturbation experiment, m=1, 2) and have lengths $|v_i|=2$. Their response vectors are therefore displayed in FIG. 4 as points in two-dimensional space. In the present example, two apparent clusters can be distinguished. These two cluster are shown in FIG. 4A, and comprise a circular cluster and a dumbbell-shaped cluster. The clustercenters are indicated by the triangle symbol (▲). As is apparent to one skilled in the art, the distribution of perturbation vectors in FIG. 4 could also be divided into three clusters, illustrated in FIG. 4B along with their corresponding centers. As will also be apparent to one skilled in the art, the two new clusters in FIG. 4B are each more compact than the one dumbbell shaped cluster in FIG. 4A. However, such an increase in compactness may not be statistically significant and so may not be indicative of the actual or unique cellular constituent sets. In particular, the compactness of a set of N clusters may be defined in this example as the inverse of the mean squared distance of each element from its cluster center, i.e., as $1/I^{(N)}_{mean}$. In general, $I^{(N+1)}_{mean} < I^{(N)}_{mean}$. Regardless of whether there are additional "real" cellular constituent sets. Accordingly, the statistical methods of this invention can be used to evaluate the statistical significance of the increased compactness which occurs, e.g., in the present example, when the number of clusters is increased from N=2 to N+1=3.

In an exemplary embodiment, the increased compactness is given by the parameter E, which is defined by Equation 15, below:

$$E = \frac{I^{(N)}_{mean} - I^{(N+1)}_{mean}}{I^{(N+1)}_{mean}} \qquad \text{(Equation 15)}$$

However, other definitions that are apparent to those skilled in the art can also be used in the statistical methods of this invention. In general, the exact definition of E is not crucial provided it is monotonically related to increase in cluster compactness.

The statistical methods of this invention provide methods to analyze the significance of E. Specifically, these methods provide an empirical distribution approach for the analysis of E by comparing the actual increase in compactness, $E_0$, for actual experimental data to an empirical distribution of E values determined from randomly permuted data (e.g., by Equation 13 above). In the two-dimensional example illustrated in FIG. 4, such a translation comprises, first, randomly swapping the perturbation indices m=1, 2 in each perturbation vector with equal probability. More specifically, the coordinates (i.e., the indices) of the vectors in each cluster being subdivided are "reflected" about the cluster center, e.g., by first translating the coordinate axes to the cluster center as shown in FIG. 4C. The results of such an operation are shown, for the two-dimensional example, in FIG. 4D. Second, the randomly permuted data are re-evaluated by the cluster algorithms of the invention, most preferably by the same cluster algorithm used to determine the original cluster(s), so that new clusters are determined for the permutated data, and a value of E is evaluated for these new clusters (i.e., for splitting one or more of the new clusters). Steps one and two above are repeated for some number of Monte Carlo trials to generate a distribution of E values. Preferably, the number of Monte Carlo trials is from about 50 to about 1000, and more preferably from about 50 to about 100. Finally, the actual increase in compactness, i.e., $E_0$, is compared to this empirical distribution of E values. For example, if M Monte Carlo simulations are performed, of which x have E values greater than $E_0$, then the confidence level in the number of clusters may be evaluated from 1−x/M. In particular, if M=100, and x=4, then the confidence level that there is no real significance in increasing the number of clusters is 1−4/100=96%.

The above methods are equally applicable to embodiments comprising hierarchical clusters and/or a plurality of elements (e.g., more than two cellular constituents). For example, the cluster tree illustrated in FIG. 3. As noted above, this clustering tree was obtained using the hclust algorithm for 34 perturbation response profiles comprising 185 cellular constituents which had significant responses. Using the clusters defined by the branches at LEVEL 2 of this tree, 100 Monte Carlo simulations were performed randomizing the 34 experimental indices and empirical distributions for the improvements in compactness E were generated for each branching in the tree. The actual improvement in compactness $E_0$ at each branch was compared with its corresponding distribution. These comparisons are shown by the numbers at each branch in FIG. 3. Specifically, these numbers indicate the number of standard deviations in the distribution by which $E_0$ exceed the average value of E. The indicated significance correspond well with the independently determined biological significance of the branches. For example, the main branch indicated in FIG. 3 by the number five (bottom label) comprises genes regulated via the calcineurin protein, whereas the branch labeled number 7 primarily comprises genes regulated by the Gcn4 transcription factor.

Classification Based Upon Mechanisms of Regulation:

Cellular constituent sets can also be defined based upon the mechanism of the regulation of cellular constituents. For example, genesets can often be defined based upon the regulation mechanism of individual genes. Genes whose regulatory regions have the same transcription factor binding sites are more likely to be co-regulated, and, as such, are more likely to co-vary. In some preferred embodiments, the regulatory regions of the genes of interest are compared using multiple alignment analysis to decipher possible shared transcription factor binding sites (see, e.g., Stormo and Hartzell, 1989, *Proc. Natl. Acad. Sci.* 86:1183-1187; and Hertz and Stormo, 1995, *Proc. of 3rd Intl. Conf on Bioinformatics and Genome Research*, Lim and Cantor, eds., Singapore: World Scientific Publishing Co., Ltd., pp. 201-216). For example, the common promoter sequence responsive to Gcn4 in 20 genes is likely to be responsible for those 20 genes co-varying over a wide variety of perturbations.

Co-regulated and/or co-varying genes may also be in the up- or down-stream relationship where the products of up-stream genes regulate the activity of down-stream genes. For example, as is well known to those of skill in the art, there are numerous varieties of gene regulation networks. Accordingly, the methods of the present invention are not limited to any particular kind of gene regulation mechanism. If it can be derived or determined from their mechanisms of regulation, whatever that mechanism happens to be, that two or more genes are co-regulated in terms of their activity change in response to perturbation, those two or more genes may be clustered into a geneset.

In many embodiments of the present invention, knowledge of the exact regulation mechanisms of certain cellular constituents may be limited and/or incomplete. In such embodiments, it may be preferred to combine cluster analysis methods, described above, with knowledge of regulatory mechanisms to derive better defined, i.e., refined cellular constituent sets. For example, in some embodiments, clustering may be used to cluster genesets when the regulation of genes of interest is partially known. In particular, in many embodiments, the number of genesets may be predetermined by understanding (which may be incomplete or limited) or the regulation mechanism or mechanisms. In such embodiments, the clustering methods may be constrained to produce the predetermined number of clusters. For example, in a particular embodiment promoter sequence comparison may indicate that the measured genes should fall into three distinct genesets. The clustering methods described above may then be constrained to generate exactly three genesets with the greatest possible distinction between those three sets.

Refinement of Cellular Constituent Sets:

Cellular constituent sets, such as cellular constituent sets identified by any of the above methods or combinations thereof, may be refined using any of several sources of corroborating information. Examples of corroborating information which may be used to refine cellular constituent sets include, but are by no means limited to, searches for common regulatory sequence patterns, literature evidence for co-regulations, sequence homology (e.g., of genes or proteins), and known shared function.

In preferred embodiments, a cellular constituent database or "compendium" is used for the refinement of genesets. In particularly preferred embodiments the compendium is a "dynamic database." For example, in certain embodiments, a compendium containing raw data for cluster analysis of cellular constituent sets (e.g., for genesets) is used to continuously update geneset definitions. Such compendia are discussed, in detail, in Section 5.#, below.

Definition of Basis Vectors:

Once cellular constituent sets have been obtained or provided, e.g., by means of a clustering analysis algorithm such as hclust, a set of basis vectors e can be, optionally, obtained or provided based on those cellular constituent sets. Such basis vectors can be used, e.g., for profile projection methods described in Section 5.#, below.

Preferably, the set of basis vectors has K×N dimensions, where K is the number of cellular constituents and N is the number of cellular constituent sets. In particular, the set of basis vectors e obtained or provided from the cellular constituent sets comprises a matrix of basis vectors which can be represented according to Equation 16:

$$e = [e^{(1)}, \ldots, e^{(q)}, \ldots, e^{(N)}] \quad \text{(Equation 16)}$$

Each basis vector, $e^{(q)}$, in equation 16 can in turn be represented as a column vector according to Equation 17:

$$e^{(q)} = \begin{pmatrix} e_1^{(q)} \\ \vdots \\ e_i^{(q)} \\ \vdots \\ e_K^{(q)} \end{pmatrix} \quad \text{(Equation 17)}$$

Preferably, the elements $e_i^{(q)}$ of the basis vectors are assigned values:

$e_i^{(q)} = \pm 1$, if cellular constituent i is a member of cellular constituent set (i.e., the cluster) q (the sign is preferably chosen so that constituents which are anti-correlated in their responses across a set of perturbations have opposite signs and constituents with positive correlation have the same sign); and $e_i^{(q)} = 0$, if cellular constituent i is not a member of cellular constituent set q.

Alternatively, the non-zero elements of $e^{(q)}$ can be given magnitudes which are proportional to the typical response magnitude of that element in the cellular constituent set q.

In preferred embodiments, the elements $e_i^{(q)}$ are normalized so that each $e^{(q)}$ has a length equal to unity, e.g., by dividing each element by the square root of the number of cellular constituents in cellular constituent set q (i.e., by the number of elements $e_i^{(q)}$ that are non-zero for a particular cellular constituent set index q). In such embodiments, random measurement errors in profiles project onto the basis vectors in such a way that the amplitudes tend to be comparable for each cellular constituent set. Thus, normalization prevents large cellular constituent sets from dominating the results of calculations involving those sets.

Re-Ordering the Cellular Constituent Index:

As noted above, in preferred embodiments of the present invention the cellular constituents are re-ordered according the cellular constituent sets or clusters obtained or provided by the above-described methods and visually displayed. Analytically, such a reordering corresponds to transforming a particular original biological response profile, such as a particular perturbation response profile, e.g., $v^{(n)}=\{v_i^{(m)}\}$ to the re-ordered profile $\{v_{\Pi(i)}^{(m)}\}$, where i is the cellular constituent index.

An exemplary re-ordering of the cellular constituents is indicated in FIGS. 5A-D. In particular, FIG. 5A shows a false color display of a plurality of genetic transcripts (i.e., cellular constituents; horizontal axis) measured in a plurality of experiments wherein cells are exposed to different perturbations (i.e., perturbation response profiles, vertical index). FIG. 5B illustrates a coregulation tree generated by the hclust algorithm from the data in FIG. 5A. FIG. 5C illustrates the visual display of the data in FIG. 5A wherein the transcripts have been re-ordered according to the clusters in the coregulation tree.

5.2.5. Grouping Measured Response Profiles

A second aspect of the analytical methods of the present invention involves methods for grouping or clustering and re-ordering of the perturbation response profiles $v^{(m)}$ into clusters or sets which are associated with similar biological effects of a perturbation. Such methods are exactly analogous to the methods described in Section 5.2.1 above. In particular, the methods and operations described in Section 5.2.1 above which are applied to the cellular constituent index i of the perturbation response profile elements $v_i^{(m)}$ may also be applied to the perturbation index m.

Such an operation is illustrated in FIGS. 5A-D. In particular, FIG. 5D illustrates a visual display of the data shown in FIG. 5C wherein the experimental (i.e., perturbation) index m has been reordered according to the clustering and other analysis methods described in Section 5.2.1 above. The result is a visual display in which experiments with similar profiles are place contiguously. Such a display greatly facilitates the identification of co-regulated genesets. In particular, by visually inspecting such a display, a user can readily identify those genesets which co-vary in groups of experiments. Such a display also facilitates the identification of experiments (e.g., particular perturbations such as particular mutations) which are associated with similar biological responses.

The analytical methods of this invention thus include methods of "two-dimensional" cluster analysis. Such two-dimensional cluster analysis methods simply comprise (1) clustering cellular constituents into sets that are co-varying in biological profiles, and (2) clustering biological profiles into sets that effect similar cellular constituents (preferably in similar ways). The two clustering steps may be performed in any order and according to the methods described above.

Such two-dimensional clustering techniques are useful, as noted above, for identifying sets of genes and experiments of particular interest. For example, the two-dimensional clustering techniques of this invention can be used to identify sets of cellular constituents and/or experiments that are associated with a particular biological effect of interest, such as a drug effect. The two-dimensional clustering techniques of this invention can also be used, e.g., to identify sets of cellular constituents and/or experiments that are associated with a particular biological pathway of interest. In one preferred embodiment of the invention, such sets of cellular constituents and/or experiments are used to determine consensus profiles for a particular biological response of interest. In other embodiments, identification of such sets of cellular constituents and/or experiments provide more precise indications of groupings cellular constituents, such as identification of genes involved in a particular biological pathway or response of interest. Accordingly, another preferred embodiment of the present invention provides methods for identifying cellular constituents, particularly new genes, that are involved in a particular biological effect, of interest e.g., a particular biological pathway. Such cellular constituents are identified according to the cluster-analysis methods described above. Such cellular constituents (e.g., genes) may be previously unknown cellular constituents, or known cellular constituents that were not previously known to be associated with the biological effect of interest.

The present invention further provides methods for the iterative refinement of cellular constituent sets and/or clusters of response profiles (such as consensus profiles). In particular, dominant features in each set of cellular constituents and/or profiles identified by the cluster analysis methods of this invention can be "blanked out", e.g., by setting their elements to zero or to the mean data value of the set. The blanking out of dominant features may done by a user, e.g., by manually selecting features to blank out, or automatically, e.g., by automatically blanking out those elements whose response amplitudes are above a selected threshold. The cluster analysis methods of the invention are then reapplied to the cellular constituent and/or profile data. Such iterative refinement methods can be used, e.g., to identify other potentially interesting but more subtle cellular constituent and/or experiment associations that were not identified because of the dominant features.

5.2.6. Projecting onto Basis Cellular Constituent Sets

In another, optional, aspect of the analytical methods of this invention, biological response profiles, including, e.g., perturbation response profiles, can be represented in terms of basis cellular constituent sets. Such methods are commonly known to those skilled in the art as "projection."

In particular, as noted in Section 5.2.1, above, the basis vectors obtained from a set of cellular constituents, such as from a geneset, can be represented according to a matrix such as the matrix depicted in Equation 16:

$$e=[e^{(1)},\ldots,e^{(q)},\ldots,e^{(N)}] \quad \text{(Equation 16)}$$

where basis vector, $e^{(q)}$, in equation 16 can in turn be represented as a column vector according to Equation 17:

$$e^{(q)} = \begin{matrix} e_1^{(q)} \\ \vdots \\ e_i^{(q)} \\ \vdots \\ e_K^{(q)} \end{matrix} \quad \text{(Equation 17)}$$

Likewise, a biological response profile, denoted here as p, can also be represented as a vector of response values for individual cellular constituents, as depicted in Equation 20:

$$p=[p_1,\ldots,p_i,\ldots,p_K] \quad \text{(Equation 20)}$$

For example, the biological response profile can be a particular perturbation response profile, $v^{(m)}$ from a compendium of perturbation response profiles. Alternatively, the biological response profile can also be a new response profile, e.g., for a novel experiment. According to the methods of the invention, the response profile p can be optionally represented in terms of the basis vectors as a "projected profile" P by means of the operation given in Equation 21, below:

$$P = p \cdot e \quad \text{(Equation 21)}$$

Equation 20, above, is well known to those skilled in the art as the "matrix dot product" of p and e. As is also recognized by those skilled in the art, the matrix dot product of p and e generates a new vector, represented by Equation 22:

$$P = [P_1, \ldots, P_q, \ldots, P_N] \quad \text{(Equation 22)}$$

In particular, each of the elements, $P_q$, of the vector P in Equations 21 and 22 is provided according to Equation 23:

$$P = p \cdot e^{(q)} = \sum_i p_i \times e_i^{(q)} \quad \text{(Equation 23)}$$

In other embodiments, the projection of a response profile p onto a basis set of cellular constituents simply comprises the average of the expression value (in p) of the genes within each geneset. In some aspects of such embodiments, the average may be weighted, e.g., so that highly expressed genes do not dominate the average value.

Similarities and differences between two or more projected profiles, for example, between $P^{(a)}$ and $P^{(b)}$ are typically more apparent than are similarities between the original profiles, e.g., $p^{(a)}$ and $p^{(b)}$, before projection. Thus it is often preferable, in practicing the methods of the present invention, to compare projected response profiles. In particular, measurement errors in extraneous genes are typically excluded or averaged out by projection. Thus, any element of a projected profile, e.g., $P^{(a)}$ or $P^{(b)}$, is less sensitive to measurement error than is the response of a single cellular constituent (i.e., of a single element of the corresponding unprojected response profile $p^{(a)}$ or $p^{(b)}$. Accordingly, the elements of a projected profile will generally show significant up- or down-regulation at lower levels of perturbation than will the individual elements (i.e., the individual cellular constituents) of the corresponding unprojected response.

Further, as is well known to those skilled in the art, averaging makes a tremendous difference, e.g., in the probabilities of detecting actual events rather than false alarms (see, e.g., Van Trees, H. L., 1968, *Detection, Estimation, and Modulation Theory* Vol. I, Wiley & Sons). Accordingly, the elements of a projected profile generally also give more accurate (i.e., small fractional error) measures of the amplitude of response at any level of perturbation. Specifically, in most embodiments of the invention there are independent measurement error in the data for each cellular constituent, or such independent errors may be reasonably assumed. In such embodiments, the fractional standard error of the q'th projected profile elements (i.e., of $P_q$) is approximately $M_q^{-1/2}$ times the average fractional error of the individual cellular constituents, where $M_q$ is the number of cellular constituents in the q'th cellular constituent sets. Accordingly, if the average measured up or down regulation of an individual cellular constituent is significant at x standard deviations, the projected profile element will be significant at $M_q^{1/2}x$ standard deviations.

Finally, because they are derived from observations of co-variance and/or co-regulation, the basis cellular constituents can frequently be directly associated with the biology, e.g., with the biological pathways, of the individual response profile. Thus, the basis cellular constituents function as matched detectors for their individual response components.

5.2.7. Consensus Profiles

In a specific embodiment of the invention, one or more consensus profiles is determined for a set of perturbation response profiles, such as in a database or "compendium" of perturbation response profiles. The present invention provides analytical methods that can be used to compare particular biological response profiles (e.g., particular perturbation response profiles such as perturbation response profiles from particular mutations) of interest to such consensus profiles. Determining Consensus Profiles:

In preferred embodiments, the consensus profiles $P^{(C)}$ of the invention are defined as the intersection of the sets of cellular constituents activated (or de-activated) by members of a group of experimental conditions, such as a group of perturbations (e.g., a group of particular mutations). Such intersections can be identified by either qualitative or quantitative methods.

In one embodiment, the intersections of cellular constituent sets are identified by visual inspection of response profile data for a plurality of perturbations. Preferably, such data is re-ordered, according, e.g., to the methods described in Section 5.2.1 and 5.2.3, above, so that co-varying cellular constituents and similar response profiles can be more readily identified. For example, FIG. 6 shows a false color display of a plurality of genetic transcripts (horizontal axis) measured in a plurality of experiments (i.e., response profiles) wherein cells of *S. cerevisiae* are exposed to a variety of different perturbations as indicated on the vertical axis. Both the cellular constituents and the response profiles have been grouped and re-ordered according to the methods of Sections 5.2.1 and 5.2.3, and those described in U.S. patent application Ser. No. 09/220,142 to Stoughton et al., filed Dec. 23, 1998 (incorporated by reference herein in its entirety), so that the co-varying cellular constituents (i.e., genesets) and similar response profiles can be readily visualized. In particular, gene transcripts that co-vary have been grouped together along the horizontal axis, and experiments that produce similar variations in gene transcripts have been grouped together along the vertical axis.

An exemplary set of eight experiments (i.e., perturbations) shown in FIG. 6 which are involved in immunosuppression conditions is first considered:

Row 15: addition of 50 μg/ml of the immunosuppressant drug FK506 to wild-type cells;

Row 18: addition of 50 μg/ml of FK506 to a strain missing the CPH1 gene;

Row 28: addition of 1 μg/ml of FK506 to wild-type cells;

Row 29: addition of 50 μg/ml of Cyclosporin A to wild-type cells;

Row 30: addition of 1 μg/ml of FK506 to a strain missing the CPH1 gene;

Row 31: deletion of the Calcineurin genes CNA1 and CNA2;

Row 32: addition of 50 μg/ml of Cyclosporin A to a strain missing the FPR gene; and Row 34: addition of 50 μg/ml of FK506 to a strain missing the GCN4 gene.

In each of the above experimental conditions, it is expected that the primary immunosuppressant effect via the calcineurin protein will be exhibited (see, e.g., Cardenas et al., 1994, *Perspectives in Drug Discovery and Design* 2:103-126; and Marton et al., 1998, *Nature Medicine* 4:1293-1301). Indeed, as can bee seen by visual inspection of FIG. 6, the common geneset in all of the above-listed perturbations is geneset no. 5 of FIG. 3, which is associated with the calcineurin protein, the primary target of the above-listed immunosuppressant drugs.

Visual inspection of FIG. 6 also reveals that Rows 28-31 not only share the primary effect of the calcineurin protein (i.e., of geneset no. 5), they also have little additional effect from other genesets. Thus, the consensus profile $P^{(C)}$ for the response shown in Rows 28-31 consist of the geneset associated with the calcineurin protein (i.e., geneset no. 5). This consensus profile may be used, e.g., to evaluate drugs or drug candidates which are intended to specifically effect calcineurin protein levels and/or activity.

By contrast, Rows 15, 18, and 34 show appreciable secondary effects from other genesets. In particular, there is a set of experiments, including Rows 12-18 of FIG. 6, which exhibits a large set of up regulated genes associated with the Gcn4 transcription factor (see, Marton et al., supra). Thus, the consensus profile for these rows consist of both the geneset associated with both the calcineurin protein and the geneset co-regulated by the Gcn4 transcription factor.

In other, more formal quantitative embodiments of the invention, the intersections of cellular constituent sets are preferably identified, e.g., by thresholding the individual response amplitudes of the projected response profiles. An exemplary illustration of such thresholding is shown in FIG. 7 for rows 15, 18, 28-32, and 34 of FIG. 6. Thresholds are indicated by the dashed lines in FIG. 7. In particular, thresholds are set at a detection limit equal to two standard errors of the geneset response, assuming uncorrelated errors in the individual genes, or standard error of ~0.15 in the $\log_{10}$, as observed for the dataset illustrated in FIG. 6. With the preferred normalization of the basis vectors (i.e., with $|e^{(q)}|=1$ for all genesets q), the appropriate threshold for the geneset amplitude is the same as that for individual genes at a particular desired confidence level. Although several genesets other than geneset no. 5 occasionally have amplitudes over the indicated threshold, the intersection of the eight sets of amplitudes that exceed the indicated threshold consists of only geneset no. 5; i.e., geneset no. 5 is the only geneset for which the response amplitude exceeds the threshold in every experiment whose thresholds are plotted in FIG. 7. Thus, the consensus profile $P^{(C)}$ for the immunosuppressants in these experiments is geneset no. 5 (i.e., the calcineurin pathway).

In alternative embodiments, intersections of cellular constituent sets may be identified arithmetically, by replacing significant amplitudes of cellular constituent sets in the projected responses (i.e., those amplitudes which are above the threshold) with values of unity, and replacing amplitudes of cellular constituent sets in the projected responses that are below the threshold with values of zero. The intersection may then be determined by the element-wise product of all project profiles. In particular, in such embodiments the consensus profile consists of those cellular constituent sets whose index is unity after the product operation.

Comparing Response to Consensus Profiles:

Once basis cellular constituent sets have been identified, e.g., according to the methods described in Section 5.2.1 above, projected profiles P may be obtained for any biological response profile p comprising the same cellular constituent as those used to define the basis cellular constituent sets, e.g., according to the methods provided in Section 5.2.4 above. As noted supra, similarities and differences between two or more projected profiles, for example between the projected profile $P^{(a)}$ and $P^{(b)}$, can be readily evaluated. In preferred embodiments, projected profiles are compared by an objective, quantitative similarity metric S. In one particularly preferred embodiment, the similarity metric S is the generalized cosine angle between the two projected profiles being compared, e.g., between $P^{(a)}$ and $P^{(b)}$. The generalized cosine angle is a metric well known to those skilled in the art, and is provided, below, in Equation 24:

$$S_{a,b} = S(P^{(a)}, P^{(b)}) = \frac{P^{(a)} \cdot P^{(b)}}{|P^{(a)}||P^{(b)}|} \quad \text{(Equation 24)}$$

In Equation 24, the dot product $P^{(a)} \cdot P^{(b)}$ is defined according to Equation 25:

$$P^{(a)} \cdot P^{(b)} = \sum_q (P_q^{(a)} \times P_q^{(b)}) \quad \text{(Equation 25)}$$

Likewise, the quantities $|P^{(a)}|$ and $|P^{(b)}|$ are provided according to the equations $|P^{(a)}|=(P^{(a)} \cdot P^{(a)})^{1/2}$, and $|P^{(b)}|=(P^{(b)} \cdot P^{(b)})^{1/2}$.

In such embodiments, projected profile $P^{(a)}$ is most similar to the projected profile $P^{(b)}$ if $S_{a,b}$ is a maximum. In more detail, $S_{a,b}$ may have a value from $-1$ to $+1$. A value of $S_{a,b}=+1$ indicates that the two profiles are essentially identical; the same cellular constituent effected in $P^{(a)}$ are proportionally effected in $P^{(b)}$, although the magnitude (i.e., strength) of the two responses may be different. A value of $S_{a,b}=-1$ indicates that the two profiles are essentially opposites. Thus, although the same cellular constituent sets in $P^{(a)}$ are proportionally effected in $P^{(b)}$, those sets which increase (e.g., are up-regulated) in $P^{(a)}$ decrease (e.g., are down regulated) in $P^{(b)}$ and vice-versa. Such profiles are said to be "anti-correlated." Finally, a value of $S_{a,b}=0$ indicates maximum dissimilarity between the two responses; those cellular constituent sets effected in $P^{(a)}$ are not effected in $P^{(b)}$ and vice-versa.

Projected profiles may also be compared to the consensus profiles $P^{(C)}$ of the present invention. Such comparisons are useful, e.g., to determine whether a particular response profile, e.g., of the biological response to a drug or drug candidate, is consistent with or false short of the consensus profile, e.g., for a class or type of drugs, or for an "ideal" biological response such as one associated with a desired therapeutic effect. Projected profiles may be compared to the consensus profiles of this invention by means of the same methods described supra for comparing projected profiles generally. Thus a give projected profile $P^{(a)}$ may be compared to a consensus profile $P^{(C)}$, e.g., by evaluating a quantitative similarity metric $S_a^{(C)}=S(P^{(a)}, P^{(C)})$, wherein $S(P^{(a)}, P^{(C)})$ is defined, e.g., according to Equation 24 above.

The statistical significance of any observed similarity $S_{a,b}$ may be assessed, e.g., using an empirical probability of distribution generated under the null hypothesis of no correlation. Such a distribution may be generated by performing projection and similarity calculations, e.g., according to the above described methods and equations, for many random permutations of the cellular constituent index i in the original unprojected response profile p. Mathematically, such a permutation may be represented by replacing the ordered set $\{p_i\}$ by $\{p_{\Pi(i)}\}$, where $\Pi(i)$ denotes a permutation of the index i. Preferably, the number of permutations is anywhere from about 100 to about 1000 different random permutations. The probability that the similarity $S_{a,b}$ arises by chance may then be determined from the fraction of the total permutations for which the similarity $S_{a,b}^{(permuted)}$ exceeds the similarity $S_{a,b}$ determined for the original, unpermuted data.

Clustering Projected Profiles:

The present invention also provides methods for clustering and/or sorting projected profiles, e.g., by means of the clustering methods described in Section 5.2.1 and 5.2.3 above, according to their similarity as evaluated, e.g., by a quantitative similarity metric S such as the generalized cosine angle. In a preferred embodiment, the clustering of a projected profile is done using the distance metric given, below, in Equation 26:

$$I_{a,b} = 1 - S_{a,b} \quad \text{(Equation 26)}$$

In a particularly preferred embodiment of this invention, the projected profiles are clustered or ordered according to their similarity to a consensus profile $P^{(C)}$, e.g., using the distance metric $I = 1 - S^{(C)} = 1 - S(P, P^{(C)})$, wherein P is the projected response profile to be sorted according to the methods of the present invention.

Such clustering and sorting methods are analogous to the clustering of the original unprojected response profiles described in Section 5.2.3 above. However, the clustering of projected response profiles has the advantages of reduced measurement error effects and enhanced capture of the relevant biology inherent to the projected response profiles.

Removal of Profile Artifacts:

In a preferred embodiment, the projection methods described above can also be used to remove unwanted response components (i.e., "artifacts") from biological profile (e.g., perturbation response profile) data. Frequently, when such profile data are obtained there are one or more poorly controlled variables which lead to measured patterns of cellular constituents (e.g., measured gene expression patterns) which are, in fact, artifacts of the measurement process and are not part of the actual biological state or response (such as a perturbation response) being measured. Exemplary variables which may produce artifacts in biological profile data include, but are by no means limited to, cell culture density and temperature and hybridization temperature, as well as concentrations of total RNA and/or hybridization reagents.

For example, Di Risi et al. (1997, *Science* 278:680-686) describe measurements using microarrays of *S. cerevisiae* cDNA, levels during the change from anaerobic to aerobic growth (i.e., the "diauxic shift"). However, if one of two nominally identical cell cultures has unintentionally progressed further into the diauxic shift than the other, their expression ratios will reflect that transcriptional changes associated with this shift. Such artifacts potentially confuse the measurements of the true transcriptional responses being sought. These artifacts may be "projected out" by removing or suppressing their patterns in the data.

In preferred embodiments, the artifact patterns in the data are known. In general, artifact patterns may be determined from any source of knowledge of the genes and relative amplitudes of response associated with such artifacts. For example, the artifact patterns may be derived from experiments with intentional perturbations of the suspected causative variables. In another embodiment, the artifact patterns may be determined from clustering analysis of control experiments where the artifacts arise spontaneously.

In such preferred embodiments, the contribution of known artifacts may be solved for and subtracted from the measured biological profile $p=\{p_i\}$, e.g., by determining the best scaling coefficients $\alpha_n$ for the contribution of artifact n to the profile. Preferably, the coefficients $\alpha_n$ are found by determining the values of $\alpha_n$ which minimize an objective function of the difference between the measured profile and the scaled contribution of the artifacts. For example, the coefficients $\alpha_n$ may be determined by the least square minimization $$\min_{\alpha_n} \left\{ \sum_i \left( p_i - \sum_n \alpha_n A_{n,i} \right)^2 w_i \right\} \quad \text{(Equation 27)}$$

wherein $A_{n,i}$ is the amplitude of artifact n on the measurement of cellular constituent i. $w_i$ is an optional weighting factor selected by a user according to the relative certainty or significance of the measured value of cellular constituent i (i.e., of $p_i$).

The "cleaned" profile $p^{(clean)}$ in which the artifacts are effectively removed, is then given by the equation $$p_i^{(clean)} = p_i - \sum_n \alpha_n A_{n,i} \quad \text{(Equation 28)}$$

wherein the coefficients $\alpha_n$ are determined, e.g., from equation 16 above.

In other embodiments, the profile p may be compared to a library of artifact signatures $A_s = \{A_{s,i}\}$ of different severity. In such embodiments, the "cleaned" profile is determined by pattern matching against this library to determine the particular template which has greatest similarity to the profile p. In such embodiments, the cleaned profile is given by $p_k^{(clean)} = p_k - A_{s,i}$, wherein the signature $A_s$ is determined, e.g., by solving the equation $$\min_s \left\{ \sum_i (p_i - A_{s,i})^2 w_i \right\} \quad \text{(Equation 29)}$$

5.3. Implementation Systems and Methods

The analytical methods of the present invention can preferably be implemented using a computer system, such as the computer system described in this section, according to the following programs and methods. Such a computer system can also preferably store and manipulate a compendium of the present invention which comprises a plurality of perturbation response profiles and which can be used by a computer system in implementing the analytical methods of this invention. Accordingly, such computer systems are also considered part of the present invention.

An exemplary computer system suitable from implementing the analytic methods of this invention is illustrated in FIG. 8. Computer system 801 is illustrated here as comprising internal components and as being linked to external components. The internal components of this computer system include a processor element 802 interconnected with a main memory 803. For example, computer system 801 can be an Intel Pentium®-based processor of 200 MHz or greater clock rate and with 32 MB or more main memory. In a preferred embodiment, computer system 801 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 804. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 805, which is most typically a monitor and a keyboard together with a graphical input device 806 such as a "mouse." The computer system is also typically linked to a network link 807 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 8. The software components comprise both software components that are standard in the art and components that are special to the present invention. These software components are typically stored on mass storage such as the hard drive 804, but can be stored on other computer readable media as well including, for example, one or more floppy disks, one or more CD-ROMs, one or more DVDs or one or more DATs. Software component 810 represents an operating system which is responsible for managing the computer system and its network interconnections. The operating system can be, for example, of the Microsoft Windows™ family such as Windows 95, Window98, WindowsNT or Windows2000. Alternatively, the operating software can be a Macintosh operating system, a UNIX operating system or the LINUX operating system. Software components 811 comprises common languages and functions that are preferably present in the system to assist programs implementing methods specific to the present invention. Languages that can be used to program the analytic methods of the invention include, for example, UNIX or LINUX shell command languages such as C and C++, PERL, FORTRAN, HTML and JAVA. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 812 comprises analytic methods of the present invention, preferably programmed in a procedural language or symbolic package. For example, software component 812 preferably includes programs that cause the processor to implement steps of accepting a plurality response profiles and storing the profiles in the memory. For example, the computer system can accept response profiles that are manually entered by a user (e.g., by means of the user interface). More preferably, however, the programs cause the computer system to retrieve response profiles from a database or compendium of response profiles; i.e., from a compendium of the present invention. Such a compendium can be stored on a mass storage (e.g., a hard drive) or other computer readable medium and loaded into the memory of the computer, or the compendium can be accessed by the computer system by means of the network 807.

Each response profile (813) contained in a compendium and/or loaded into the memory of the computer system is represented by a data structure comprising a plurality of data fields. In particular, the data structure for a particular response profile will comprise a separate data field for each cellular constituent whose measured amount, e.g., abundance or activity, is an element of the response profile. The data field for each cellular constituent will contain a value representing the measured amount, e.g., the abundance or activity, of the cellular constituent is the biological sample subject to the particular perturbation or, more preferably, a value representing the change in the cellular constituent's measured amount, e.g., abundance or activity, from an unperturbed or "wild-type" cell or sample. The response profile will also comprise additional data fields that contain values describing the particular perturbation. For example, in embodiments wherein the perturbation is a genetic mutation, these fields can contain values that identify the particular gene that is mutated and/or and identifier that indicates the particular cell line or strain of the cell or organism containing the genetic mutation. In embodiments wherein the perturbation comprises exposing the biological sample to one or more drugs, the fields will comprise values that identify the drug or drugs and, preferably, the dosages administered. The each response profile data structure in the compendium preferably further comprises one or more data fields that contain values indicating, if known, the biological activity that is associated with the perturbation and/or its profile. The data structure representing a response profile can, optionally, contain other data fields as well. For example, the data structure can further comprise one or more fields whose values indicate the growth rate of a cell or organism subject to the particular modification or perturbation.

Among the response profiles that can be accepted by a computer system of the present invention are response profiles for modifications or perturbations to uncharacterized cellular constituents (e.g., uncharacterized genes or gene products). The analytic software component 812 preferably also comprises programs and/or subroutines which can cause the processor to perform steps of clustering response profiles accepted by the computer system (e.g., the response profiles of the compendium) and, optionally, steps of clustering the cellular constituents whose activities or abundances are elements of the response profiles. Finally, the programs and subroutines of software component 812 can also cause the processor to implement steps of comparing one or more response profiles for perturbations to uncharacterized cellular constituents to the other response profiles accepted by the computer. In particular, these programs and subroutines preferably cause the processor to identify response profiles that cluster with a response profile for an uncharacterized cellular constituent whose biological function is to be evaluated. In preferred embodiments, the programs further identify the biological function, if known, of other cellular constituents whose response profiles cluster with the response profile for the uncharacterized cellular constituent (e.g., by appropriate data fields in the data records representing these response profiles), and reporting the biological function or functions of these cellular constituents to a user.

In one embodiment, the present invention relates to a computer system for identifying the biological function with which a cellular constituent is associated, comprising one or more processor units and one or more memory units connected to the one or more processor units, said one or more memory units containing one or more programs that carry out the steps of: (a) receiving a data structure for a first response profile from a cell type or type of organism in which the cellular constituent to be characterized is perturbed; and (b) comparing said first response profile or a predicted response profile derived therefrom, to a database comprising a plurality of landmark response profiles to determine the landmark profile that is most similar to the first response profile, wherein each landmark profile is generated by a cell of said cell type or type of organism in which a cellular constituent having a known biological function is perturbed. The known biological function of the cellular constituent perturbed in the one or more landmark response profiles determined in step (b) is the biological function with which the cellular constituent is associated.

The present invention further relates to a computer program product for use in conjunction with a computer, which causes the one or more processor units of the computer to execute steps (a) and (b), above.

In a second embodiment, the present invention relates to a computer system for identifying the biological function with which a cellular constituent is associated, comprising one or more processor units and one or more memory units connected to the one or more processor units, said one or more memory units containing one or more programs that carry out only the comparing step (b), above.

In addition, the invention relates to a computer program product for use in conjunction with a computer, which causes the one or more processor units of the computer to execute only the comparing step (b), above.

In addition to the exemplary program structures and computer systems described herein, other, alternative program structures and computer systems will be readily apparent to the skilled artisan. Such alternative systems, which doe not depart from the above described computer system and programs structures either in spirit or in scope, are therefore intended to be comprehended within the accompanying claims.

5.4. Cellular Modification Methods

Methods for targeted cellular modification and perturbation at various levels of a cell are increasingly widely known and applied in the art. Any such methods that are capable of specifically targeting and altering (e.g., either by increase or activation or by decrease or inhibition) specific cellular constituents (e.g., gene expression, RNA concentrations, protein abundances, protein activities and so forth) can be employed in constructing the modified-cell perturbation patterns of the present invention. Preferable methods are capable of individually targeting each of a plurality of cellular constituents and most preferably a substantial fraction of such cellular constituents. The methods described in this section are exemplary of those that can be used to modify cellular constituents and thereby produce perturbations which generate the perturbation response profiles used in the methods of the present invention as described below.

The modifications and/or perturbations are preferably arranged to be "saturating." In the case of decreasing abundances or inhibiting activities, a modification is preferably arranged to decrease the particular cellular constituent or its activity to such an extent that all targets for action of that cellular constituent are essentially unsaturated or unbound. For example, it is preferable that all the mRNA encoding a protein species, or all of the encoded protein species itself, be eliminated from the cell (e.g., by deletion of the gene encoding that protein species). In the case of increasing abundances or activities, a modification is preferably arranged to increase the cellular constituent present in a cell to such an extent that all targets for action of the cellular constituent are essentially saturated or bound.

Certain preferred and alternative methods of cellular modification and perturbation are described in each of the following subsections.

5.4.1. Genetic Modification

Genetically modified cells and organisms, i.e., mutant cells and organisms, can be made using cells of any organism from which genomic sequence information (even only partial genomic sequence information) is available. Methods that allow deletion (including disruption) of specific genes or over-expression of specific genes are well known in the art. Preferably, a compendium is constructed that includes perturbation response profiles that represent the transcriptional states of each of a plurality of different mutated cells. In particular, the compendium will preferably comprise perturbation response profiles for mutations to at least 2% of the genes of the subject cell or organism, and more preferably at least 5%, still more preferably at least 15%, still more preferably at least 30%, still more preferably at least 40%, most preferably at least 75% of the genes of the subject cell or organism. Genome sequencing is underway for several eukaryotic organisms, including humans, mice, nematodes, *Aradidopsis* and flies. It is further noted, however, that perturbations response profiles for mutant cell and organisms can be obtained and used in the methods of the present invention, as indicated, without the need to construct a compendium.

In a preferred embodiment, the invention is practiced out using perturbation response profiles from an organism such as a yeast (e.g., *Saccharomyces cerevisiae*) such which the sequence of the entire genome has been determined and/or for which well-established methods for deleting, disrupting or modifying specific genes are readily available. It is currently believed that most (in particular about 80%) of the genes in *S. cerevisiae* can be deleted, one at a time, with little or no effect on the ability of the organism to reproduce. Further, biological functions are often conserved between yeast and humans. For example, almost half of the proteins identified as defective in human heritable diseases show amino acid similarity to yeast proteins (Goffeau et al., 1996, *Science* 274:546-567). A preferred strain of yeast is a *S. cerevisiae* strain for which yeast genomic sequence is known, such as strain S288C or a substantially isogenic derivative thereof (see, e.g., Bussey et al., 1995, *Proc. Natl. Acad. Sci. U.S.A.* 92:3809-3813; Dujon et al., 1994, *Nature* 369:371-378; Galibert et al., 1996, *E.M.B.O. J* 15:2031-2049; Feldmann et al., 1994, *E.M.B.O. J.* 13:5795-5809; Johnston et al., 1994, *Science* 265:2077-2082). However, other strains of yeast can be used as well. Such yeast strains are readily available from the American Type Culture Collection, 10801 University Boulevard, Manassas, Va. 20110-2209. Standard techniques for manipulating yeast are also known in the art and are described, e.g., in Kaiser et al., 1994, *Methods in Yeast Genetics: A Cold Spring Harbor Laboratory Course Manual*, Cold Spring Harbor Laboratory Press, New York; and in Sherman et al., 1986,

*Methods in Yeast Genetics: A Laboratory Manual*, Cold Spring Harbor Laboratory, Cold Spring Harbor, N.Y.

Construction of Deletion and Over-Expression Mutants:

In a preferred embodiment of the present invention, yeast cells are used. In one embodiment, yeast genes are disrupted or deleted using, e.g., the methods described in Baudin et al., 1993, *Nucl. Acids. Res.* 21:3329-3330. See also Wach et al., 1994, *Yeast* 10:1793-1808. The method uses a selectable marker, e.g., the KanMx gene which serves in a gene replacement cassette. The cassette is transformed into a haploid yeast strain and homologous recombination results in the replacement of the targeted gene with the selectable marker. In one embodiment, a precise null mutation (i.e., a deletion of the targeted gene from start codon to stop codon) is generated. An advantage of using complete null mutants is that it avoids problems with residual or altered functions associated with truncated products. However, in some embodiments a deletion or mutation that affects less than the entire protein coding sequence (e.g., a deletion of only one domain of a protein) can be used.

In some embodiments, the polynucleotide (e.g., containing a selectable marker) used for transformation of the yeast cell includes an oligonucleotide marker that serves as a unique identifier of the resulting deletion strain; as described, for example, in Shoemaker et al., 1996, *Nature Genetics* 14:450. Once made, disruptions can be verified by PCR using the internal KanMx sequences. Alternatively, disruptions can be verified by using an external primer in the yeast genome that immediately flanks the disrupted gene and assaying for a PCR product of the expected size. When yeast is used as the subject cell or organism, it can be advantageous to disrupt genes in three yeast strains. In particular, for deletions of essential genes, genes can be disrupted in haploid yeast strains of the a and α mating types and in a diploid strain.

Over-expression mutants are preferably made by modifying the promoter for the gene of interest, usually by replacing the promoter with a promoter other than that naturally associated with the gene. For example, the promoter of a gene of interest can be replaced with an inducible promoter, including a titratable promoter, according to the methods described hereinbelow. Alternatively, an enhancer sequence can be added, e.g., to an endogenous gene to by modified. Other methods for carrying out genetic modification to increase expression from a predetermined gene are well known in the art and within the scope of the present invention. Such methods include, for example, expression of a gene from vectors (e.g., plasmids) carrying the gene of interest.

Titratable Expression Systems:

Any of the several known titratable, or equivalently controllable, expression systems available for use in the budding yeast *Saccharomyces cerevisiae* are adaptable to this invention (Mumberg et al., 1994, *Nucl. Acids Res.* 22:5767-5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, *Mol Cell. Biol.* 8:1440-1448). The GAL1 promoter is strongly repressed by the presence of glucose in the growth medium, and is gradually switched on in a graded manner to high levels of expression by the decreasing abundance of glucose and the presence of galactose. The GAL1 promoter usually allows a 5-100 fold range of expression control on a gene of interest.

Other frequently used promoter systems include the MET25 promoter (Kerjan et al., 1986, *Nucl. Acids. Res.* 14:7861-7871), which is induced by the absence of methionine in the growth medium, and the CUP1 promoter, which is induced by copper (Mascorro-Gallardo et al., 1996, *Gene* 172:169-170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, *Yeast* 13:837-848). The Tet promoter, adopted from mammalian expression systems (Gossen et al., 1995, *Proc. Nat. Acad. Sci. USA* 89:5547-5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels gene expression can be achieved in the steady state by addition of intermediate levels of drug. Furthermore, levels of doxycycline that give maximal repression of promoter activity (10 micrograms/nil) have no significant effect on the growth rate on wild type yeast cells (Gari et al.; 1997, *Yeast* 13:837-848).

In mammalian cells, several means of titrating expression of genes are available (Spencer, 1996, *Trends Genet.* 12:181-187). As mentioned above, the Tet system is widely used, both in its original form, the "forward" system, in which addition of doxycycline represses transcription, and in the newer "reverse" system, in which doxycycline addition stimulates transcription (Gossen et al., 1995, *Proc. Natl. Acad. Sci. USA* 89:5547-5551; Hoffmann et al., 1997, *Nucl. Acids. Res.* 25:1078-1079; Hofmann et al., 1996, *Proc. Natl. Acad. Sci. USA* 83:5185-5190; Paulus et al., 1996, *Journal of Virology* 70:62-67). Another commonly used controllable promoter system in mammalian cells is the ecdysone-inducible system developed by Evans and colleagues (No et al., 1996, *Proc. Nat. Acad. Sci. USA* 93:3346-3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, *Proc. Nat. Acad. Sci. USA* 93:4604-4607; Spencer, 1996, *Trends Genet.* 12:181-187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Initrogen, Inc.), which contains components of the Epstein-Barr virus necessary for plasmid replication.

In a preferred embodiment, titratable expression systems, such as the ones described above, are introduced into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, *Development* 122:4149-4157; Spradling et al., 1995, *Proc. Natl. Acad. Sci. USA,* 92:10824-10830; Ramirez-Solis et al., 1993, *Methods Enzymol.* 225: 855-878; and Thomas et al., 1987, *Cell* 51:503-512.

Construction of Mutants in Other Organisms:

The methods of the present invention can be carried out using cells from any organism for which the genomic sequence of at least one gene is available. Such organisms include, but are not limited to, eukaryotic organisms such as fruit flies (e.g., *D. melanogaster*), nematodes (e.g., *C. elegans*) and mammalian cells such as cells derived from mice and humans. For example, the complete genomic sequence of *D. melanogaster* has been determined (Jasny, 2000, Science 287:2181). A substantial portion of the genomes of other eukaryotes, including the mouse and human genomes, have also been sequenced.

Methods for disrupting specific genes in such organisms are well known to those of skill in the art and described, e.g., in Anderson, 1995, *Methods Cell Biol.* 48:31-58; Pettitt et al., 1996, *Development* 122:4149-4157; Spradling et al., 1995, *Proc. Natl. Acad. Sci. U.S.A.* 92:10824-10830; Ramirez-Solis et al., 1993, *Methods Enzymol.* 225:855-878; and Thomas et al., 1987, *Cell* 51:503-512.

Transfection or viral transduction of target genes can also introduce controllable perturbations or modifications in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids that are known in the art, for example the pcDNA3.1+/−system (Invitrogen, Inc.) or retroviral vectors, and introduced into the non-expressing host cells. Transfected or transduced cells expressing the target gene can be isolated, e.g., by selection for a drug resistance marker encoded by the expression vector. The level of gene transcription is monotonically related to the transfection dosage. Accordingly, response profiles for the effects of varying levels of the target gene may be obtained.

A particular, non-limiting example of the use of this method is the search for drugs that target the src-family protein tyrosine kinase, lck, a key component of the T cell receptor activation pathway (Anderson et al., 1994, *Adv. Immunol.* 56:171-178). Inhibitors of this enzyme are of interest as potential immunosuppressive drugs (Hanke J H, 1996, *J. Biol Chem* 271(2):695-701). A specific mutant of the Jurkat T cell line (JcaM1) is available that does not express lck kinase (Straus et al., 1992, *Cell* 70:585-593). Therefore, introduction of the lck gene into JCaM1 by transfection or transduction permits specific perturbation of pathways of T cell activation regulated by the 1ck kinase. The efficiency of transfection or transduction, and thus the level of perturbation, is dose related. The method is generally useful for providing perturbations of gene expression or protein abundances in cells not normally expressing the genes to be perturbed.

5.4.2. Methods of Modifying RNA Abundances and Activities

Methods of modifying RNA abundances and activities currently fall within three classes, ribozymes, antisense species, and RNA aptamers (Good et al., 1997, *Gene Therapy* 4: 45-54). Controllable application or exposure of a cell to these entities permits controllable perturbation of RNA abundances.

Ribozymes are RNAs which are capable of catalyzing RNA cleavage reactions. (Cech, 1987, *Science* 236:1532-1539; PCT International Publication WO 90/11364, published Oct. 4, 1990; Sarver et al., 1990, *Science* 247: 1222-1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, *Nature* 334:585-591; Koizumi et al., 1988, *FEBS Lett.* 228:228-230; Koizumi et al., 1988, *FEBS Lett.* 239:285-288). Ribozyme methods involve exposing a cell to, inducing expression in a cell, etc. of such small RNA ribozyme molecules. (Grassi and Marini, 1996, *Annals of Medicine* 28: 499-510; Gibson, 1996, *Cancer and Metastasis Reviews* 15: 287-299).

Ribozymes can be routinely expressed in vivo in sufficient number to be catalytically effective in cleaving mRNA, and thereby modifying mRNA abundances in a cell. (Cotten et al., 1989, *EMBO J.* 8:3861-3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, *Proc. Natl. Acad. Sci. U.S.A.* 86: 6553-6556; Lemaitre et al., 1987, *Proc. Natl. Acad. Sci. U.S.A.* 84: 648-652; PCT Publication No. WO 88/09810, published Dec. 15, 1988), hybridization-triggered cleavage agents (see, e.g., Krol et al., 1988, *BioTechniques* 6: 958-976) or intercalating agents (see, e.g., Zon, 1988, *Pharm. Res.* 5: 539-549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15: 6625-6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16: 3209), methylphosphonate oligonucleotides can be prepared by use of controlled pore glass polymer supports (Sarin et al., 1988, *Proc. Natl. Acad. Sci. U.S.A.* 85: 7448-7451), etc. In another embodiment, the oligonucleotide is a 2'-0-methylribonucleotide (Inoue et al., 1987, *Nucl. Acids Res.* 15: 6131-6148), or a chimeric RNA-DNA analog (Inoue et al., 1987, *FEBS Lett.* 215: 327-330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bemoist and Chambon, 1981, *Nature* 290: 304-310), the promoter contained in the 3' long terminal repeat of Rous sarcoma virus (Yamamoto et al., 1980, *Cell* 22: 787-797), the herpes thymidine kinase promoter (Wagner et al., 1981, *Proc. Natl. Acad. Sci. U.S.A.* 78: 1441-1445), the regulatory sequences of the metallothionein gene (Brinster et al., 1982, *Nature* 296: 39-42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, *Gene Therapy* 4: 45-54) that can specifically inhibit their translation.

5.4.3. Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et al., 1994, *Science* 263:1273-1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell*, Chpt. 8, New York: W.H. Freeman and Co.) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrons which are responsive to other inducing factors, such as drugs and temperature changes.

Target protein abundances and also, directly or indirectly, their activities can also be decreased by (neutralizing) antibodies. By providing for controlled exposure to such antibodies, protein abundances/activities can be controllably modified. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, *Immunology Today* 9:84-86) or transforming hybridoma mRNA encoding a desired antibody into a cell (Burke et al., 1984, *Cell* 36:847-858). In a further technique, recombinant antibodies can be engineering and ectopically expressed in a wide variety of non-lymphoid cell types to bind to target proteins as well as to block target protein activities (Biocca et al., 1995, *Trends in Cell Biology* 5:248-252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, *Current Opinion in Immunology* 9:210-212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, *Antibody Engineering*, vol. 2, Borrebaeck ed., IRL Press, pp 295-361). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacillus Calmette-Guerin (BCG) and corynebacterium parvum.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256: 495-497), the trioma technique, the human B-cell hybridoma technique (Kozbor et al., 1983, *Immunology Today* 4: 72), and the EBV hybridoma technique to produce human monoclonal antibodies (Cole et al., 1985, *in Monoclonal Antibodies and Cancer Therapy*, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.* 80: 2026-2030), or by transforming human B cells with EBV virus in vitro (Cole et al., 1985, in *Monoclonal Antibodies and Cancer Therapy*, Alan R. Liss, Inc., pp. 77-96). In fact, according to the invention, techniques developed for the production of "chimeric antibodies" (Morrison et al., 1984, *Proc. Natl. Acad. Sci. U.S.A.* 81: 6851-6855; Neuberger et al., 1984, *Nature* 312: 604-608; Takeda et al., 1985, *Nature* 314: 452-454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, *J. Biol. Chem.* 267:16007-16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, *EMBO J.* 13:3245-3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946,778) can be adapted to produce single chain antibodies specific to the target protein. An additional embodiment of the invention utilizes the techniques described for the construction of Fab expression libraries (Huse et al., 1989, *Science* 246: 1275-1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the $F(ab')_2$ fragment which can be produced by pepsin digestion of the antibody molecule; the Fab' fragments that can be generated by reducing the disulfide bridges of the $F(ab')_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

5.4.4. Methods of Modifying Protein Activities

Methods of directly modifying protein activities include, inter alia, dominant negative mutations, specific drugs (used in the sense of this application) or chemical moieties generally, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, *Nature* 329:219-222). In the case of active monomeric forms, over expression of an inactive form can cause competition for natural substrates or ligands sufficient to significantly reduce net activity of the target protein. Such over expression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, *Current Opinion in Immunology* 8:285-290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, *EMBO J.* 9:1805-1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

5.4.5. Drugs of Specific Known Action

Finally, activities of certain target proteins can be controllably altered by exposure to exogenous drugs or ligands. In a preferable case, a drug is known that interacts with only one target protein in the cell and alters the activity of only that one target protein. Graded exposure of a cell to varying amounts of that drug thereby causes graded perturbations of pathways originating at that protein. The alteration can be either a decrease or an increase of activity. Less preferably, a drug is known and used that alters the activity of only a few (e.g., 2-5) target proteins with separate, distinguishable, and non-overlapping effects. Graded exposure to such a drug causes graded perturbations to the several pathways originating at the target proteins.

5.5. Measurement Methods

Biological response profiles are obtained for use in the instant invention by measuring cellular constituents that are changed by a particular modification or perturbation to a cell or organism, such as any of the modifications and perturbations described, above, in Section 5.4. These cellular characteristics can be of any aspect of the biological state of a cell or organism. The can be, for example, measurements of the transcription state, in which RNA abundances are measured, measurements of the translation state, in which protein abundances are measured, or measurements of the activity state, in which protein activities are measured. The measured cellular characteristics can also be of mixed aspects, for example, in which the activities of one or more proteins are measured along with RNA abundances (i.e., gene expression). This section describes several exemplary methods for measuring the cellular constituents in a biological response. However, the methods described herein are non-limiting in that the skilled artisan will readily appreciate other methods for measuring cellular constituents that are adaptable to the present invention.

Embodiments of the present invention based on measuring the transcriptional state of a cell are particularly preferred.

The transcriptional state can be readily measured by techniques of hybridization to arrays of nucleic acid or nucleic acid mimic probes, as described in the next subsection, or by other gene expression technologies that are described hereinbelow in subsequent subsections. However, measured, the result is response data comprising values which represent RNA abundance ratios and which usually reflect DNA expression ratios (in the absence of significant differences in RNA degradation rates). Such measurement methods are described in particular detail in Section 5.5.2 below.

In various alternative embodiments, aspects of the biological state other the transcriptional state, such as the translational state, the activity state or mixed aspects of the biological state, can be measured. Details of these alternative embodiments are described, below, in Section 5.5.3.

5.5.1. Measurement of Drug Response Data

To measure drug response data, cell are exposed to graded levels of the drug or drug candidate of interest. When the cells are grown in vitro, the compound is usually added to their nutrient medium. In the case of yeast, such as *S. cerevisiae*, it is preferably to harvest the cells in early log phase, since expression patterns are relatively insensitive to time of harvest at that time. The drug is added in a graded amount that depends on the particular characteristics of the drug, but usually will be between about 1 ng/ml and 100 mg/ml. In some cases a drug will be solubilized in a solvent such as DMSO.

The biological state of cells exposed to the drug and cells not exposed to the drug is measured according to any of the below described methods. Preferably, transcript or microarrays are used to find the mRNAs with altered expression due to exposure to the drug. However, other aspects of the biological state may also be measured to determine, e.g., proteins with altered translation or activities due to exposure to the drug.

It is preferable for measurements of drug responses, in the case of two-colored differential hybridization described below, to measure also with reversed labeling. Also, it is preferable that the levels of drug exposure used provide sufficient resolution of rapidly changing regions of the drug response, e.g., by using approximately ten levels of drug exposure.

5.5.2. Transcriptional State Measurement

In general, measurement of the transcriptional state can be performed using any probe or probes which comprise a polynucleotide sequence and which are immobilized to a solid support or surface. For example, as described supra, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial sequences of genomic DNA, cDNA, or mRNA sequences extracted from cells. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, *Molecular Cloning: A Laboratory Manual*, 2nd ed., Vol. 1-3, Cold Spring Harbor Laboratory, Cold Spring Harbor, New York). Alternatively, the solid support or surface may be a glass or plastic surface.

Microarrays Generally:

In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel. Microarrays can be employed, e.g., for analyzing the transcriptional state of a cell, such as the transcriptional states of cells exposed to graded levels of a drug of interest, or to graded perturbations to a biological pathway of interest.

In preferred embodiments, a microarray comprises a support or surface with an ordered array of binding (e.g., hybridization) sites or "probes" for products of many of the genes in the genome of a cell or organism, preferably most or almost all of the genes. Preferably the microarrays are addressable arrays, preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics: The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 5 $cm^2$ and 25 $cm^2$, preferably between 12 $cm^2$ and 13 $cm^2$. However, larger arrays are also contemplated and may be preferable, e.g., for use in screening and/or signature chips comprising a very large number of distinct oligonucleotide probe sequences. Preferably, a given binding site or unique set of binding sites in the microarray will specifically bind (e.g., hybridize) to the product of a single gene in a cell (e.g., to a specific mRNA, or to a specific cDNA derived therefrom). However, as discussed supra, in general other, related or similar sequences will cross hybridize to a given binding site. Although there may be more than one physical binding site per specific RNA or DNA, for the sake of clarity the discussion below will assume that there is a single, completely complementary binding site.

The microarrays of the present invention include one or more test probes, each of which has a polynucleotide sequence that is complementary to a subsequence of RNA or DNA to be detected. Each probe preferably has a different nucleic acid sequence, and the position of each probe on the solid surface is preferably known. Indeed, the microarrays are preferably addressable arrays, and more preferably are positionally addressable arrays. Specifically, each probe of the array is preferably located at a known, predetermined position on the solid support such that the identity (i.e., the sequence) of each probe can be determined from its position on the array (i.e., on the support or surface).

Preferably, the density of probes on a microarray is about 100 different (i.e., non-identical) probes per 1 $cm^2$ or higher. More preferably, a microarray of the invention will have at least 550 different probes per 1 $cm^2$, at least 1,000 different probes per 1 $cm^2$, at least 1,500 different probes per 1 $cm^2$ or at least 2,000 different probes per 1 cm². In a particularly preferred embodiment, the microarray is a high density array, preferably having a density of at least about 2,500 different probes per 1 cm². The microarrays of the invention therefore preferably contain at least 2,500, at least 5,000, at least 10,000, at least 15,000, at least 20,000, at least 25,000, at least 50,000, at least 55,000, at least 100,000 or at least 150,000 different (i.e., non-identical) probes.

In specific embodiments, the density of probes on a microarray is between about 100 and 1,000 different (i.e., non-identical) probes per 1 cm², between 1,000 and 5,000 different probes per 1 cm², between 5,000 and 10,000 different probes per 1 cm², between 10,000 and 15,000 different probes per 1 cm², between 15,000 and 20,000 different probes per 1 cm², between 50,000 to 100,000 different probes per 1 cm², between 100,000 to 500,000 different probes per 1 cm², or more than 500,000 different (i.e., non-identical) probes per 1 cm².

In one embodiment, the microarray is an array (i.e., a matrix) in which each position represents a discrete binding site for a product encoded by a gene (i.e., an mRNA or a cDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often to at about 75%, more often to at least about 85%, even more often to about 90%, and still more often to at least about 99%. Alternatively, however, "picoarrays" may also be used. Such arrays are microarrays which contain binding sites for products of only a limited number of genes in the target organism's genome. Generally, a picoarray contains binding sites corresponding to fewer than about 50% of the genes in the genome of an organism.

Preferably, the microarray has binding sites for genes relevant to the action of a drug of interest or in a biological pathway of interest. The number of genes in a genome can be estimated from the number of mRNAs expressed by the organism, or by extrapolation from a well characterized portion of the genome. When the genome of the organism of interest has been sequenced, the number of open reading frames can be determined and mRNA coding regions identified by analysis of the DNA sequence. For example, the genome of Saccharomyces cerevisiae has been completely sequenced, and is reported to have approximately 6275 ORFs longer than 297 nucleotides. Analysis of these ORFs indicates that there are 5885 ORFs that are likely to encode protein products (Goffeau et al., 1996, Science 274:546-567). In contrast, the human genome is estimated to contain approximately $10^5$ genes.

Preparing Probes for Microarrays:

As noted above, the "probe" to which a particular polynucleotide molecules specifically hybridizes according to the invention is a complementary polynucleotide sequence. In one embodiment, the probes of the microarray comprise nucleotide sequences greater than about 250 bases in length corresponding to one or more genes or gene fragments. For example, the probes may comprise DNA or DNA "mimics" (e.g., derivatives and analogues) corresponding to at least a portion of each gene in an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of gene segments from genomic DNA, cDNA (e.g., by RT-PCR), or cloned sequences. PCR primers are preferably chosen based on known sequence of the genes or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 50,000 bases, and usually between 300 bases and 1000 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 500 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

Attaching Probes to the Solid Surface:

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics*

11:687-690). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioeletronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

Target Polynucleotide Molecules:

As described, supra, the polynucleotide molecules which may be analyzed by the present invention may be from any source, including naturally occurring nucleic acid molecules, as well as synthetic nucleic acid molecules. In a preferred embodiment, the polynucleotide molecules analyzed by the invention comprise RNA, including, but by no means limited to, total cellular RNA, poly(A)$^+$ messenger RNA (mRNA), fraction thereof, or RNA transcribed from cDNA (i.e., cRNA; see, e.g., Linsley & Schelter, U.S. patent application Ser. No. 09/411,074, filed Oct. 4, 1999). Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294-5299). In an alternative embodiment, which is preferred for *S. cerevisiae*, RNA is extracted from cells using phenol and chloroform, as described in Ausubel et al. (Ausubel et al., eds., 1989, *Current Protocols in Molecular Biology*, Vol III, Green Publishing Associates, Inc., John Wiley & Sons, Inc., New York, at pp. 13.12.1-13.12.5). Poly (A)$^+$ RNA can be selected, e.g., by selection with oligo-dT cellulose or, alternatively, by oligo-dT primed reverse transcription of total cellular RNA. Cells of interest include, but are by no means limited to, wild-type cells, drug-exposed wild-type cells, modified cells, diseased cells and, in particular, cancer cells.

In one embodiment, RNA can be fragmented by methods known in the art, e.g., by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, *Nature Biotechnology* 14:1675).

In other embodiments, the polynucleotide molecules to be analyzed may be DNA molecules such as fragmented genomic DNA, first strand cDNA which is reverse transcribed from mRNA, or PCR products of amplified mRNA or cDNA.

Hybridization to Microarrays:

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium sarcosine and 30% formamide.

Signal Detection and Data Analysis:

It will be appreciated that when cDNA complementary to the RNA of a cell is made and hybridized to a microarray under suitable hybridization conditions, the level of hybridization to the site in the array corresponding to any particular gene will reflect the is prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses, one cell is exposed to a drug and another cell of the same type is not exposed to the drug. The cDNA derived from each of the two cell types are differently labeled so that they can be distinguished. In one embodiment, for example, cDNA from a cell treated with a drug is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA is thereby detected.

In the example described above, the cDNA from the drug-treated cell will fluoresce green when the fluorophore is stimulated, and the cDNA from the untreated cell will fluoresce red. As a result, when the drug treatment has no effect, either directly or indirectly, on the relative abundance of a particular mRNA in a cell, the mRNA will be equally prevalent in both cells, and, upon reverse transcription, red-labeled and green-labeled cDNA will be equally prevalent. When hybridized to the microarray, the binding site(s) for that species of RNA will emit wavelength characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, Science 270:467-470. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Res. 6:639-645). In a preferred embodiment, the arrays are scanned with a laser fluorescent scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, Genome Res. 6:639-645. Alternatively, the fiber-optic bundle described by Ferguson et al., 1996, Nature Biotech. 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

Other Methods of Transcriptional State Measurement:

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. U.S.A. 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) which are generated at known positions relative to a defined mRNA end (see, e.g., Velculescu, 1995, Science 270:484-487).

Such methods and systems of measuring transcriptional state, although less preferable than microarrays, may, nevertheless, be used in the present invention.

5.5.3. Measurements of Other Aspects of Biological State

Although monitoring cellular constituents other than mRNA abundances currently presents certain technical difficulties not encountered in monitoring mRNAs (i.e., the transcriptional state), it will be apparent to those skilled in the art that the use of methods of this invention are applicable to any cellular constituent that can be monitored.

In various embodiments of the present invention, aspects of the biological state other than the transcriptional state, such as the translational state, the activity state, or mixed aspects thereof can be measured in order to obtain drug responses for the present invention. Details of these embodiments are described in this section.

Translational State Measurements:

Measurements of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y.). In a preferred embodiment, monoclonal antibodies are raised against synthetic peptide fragments designed based on genomic sequence of the cell. With such an antibody array, proteins from the cell are contacted to the array, and their binding is assayed with assays known in the art.

Alternatively, proteins can be separated by two-dimensional gel electrophoresis systems. Two-dimensional gel electrophoresis is well known in the art, and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Set U.S.A.* 93:1440-1445; Sagliocco et al., 1996, *Yeast* 12:1519-1533; and Lander, 1996, *Science* 274:536-539. The resulting electropherograms can be analyzed by numerous techniques, including mass spectrometric techniques, western blotting, and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

Activity State Measurements:

Where activities of proteins relevant to the characterization of drug action can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known or measured, the changes in protein activities form the response data analyzed by the foregoing methods of this invention.

Mixed Aspects of Biological State:

In alternative and non-limiting embodiments, response data may be formed of mixed aspects of the biological state of a cell. Response data can be constructed from combinations of, e.g., changes in certain mRNA abundances, changes in certain protein abundances, and changes in certain protein activities.

5.5.4. Statistical Models for Measurement Error

In preferred embodiments, the methods of the present invention also provide a confidence value for the measured change of each cellular constituent in a biological profile. Exemplary models for measurement error, although known in the art, are therefore described herein. In particular, while not limited to any particular embodiment of the measurement methods of this invention, this section describes such error models specifically in terms of a preferred embodiment wherein mRNA transcript abundances are measured using microarrays. As is appreciated by the skilled artisan, however, such error models can be readily adopted for use in other embodiments of the invention and are not, therefore, merely limited to microarrays.

The confidence value indicates, in particular, the reliability (e.g., the statistical certainty) of the measured change of cellular constituent i's, e.g., abundance or activity, in response to the perturbation m. The repeatability of each cellular constituent's measured change (e.g., each gene's measured expression change) across a plurality of identical or at least substantially identical experiments is the most preferable input for determining such a confidence value. However, most preferably the values obtained in such identical or substantially identical experiments are averaged with appropriate relative weights determined, e.g., according to a particular model for the uncertainties in individual experiments.

Suitable models are already known in the art that can be used in the methods of this invention. For example, a ratio analysis method has been previously described by the National Human Genome Research Institute's Microarray Project (see, in particular, http://www.nhgri.nih.gov/DIR/LCG/15K/HTML/imag_analysis.html) to determine whether gene expression differs significantly between perturbed and unperturbed states. More preferably, however, a "single-array" error model is used that assumes a combination of additive and multiplicative errors. Specifically, a preferred statistic that can be used to define significance is provided by Equation 30 below:

$$X = \frac{a_2 - a_1}{[\sigma_1^2 + \sigma_2^2 + f^2(a_1^2 + a_2^2)]^{1/2}} \qquad \text{(Equation 30)}$$

In more detail, the quantities $a_1$ and $a_2$ denote the amplitudes of a particular cellular constituent in the unperturbed and perturbed states, respectively. $\sigma_1$ and $\sigma_2$ are the uncertainties in the measurements of $a_1$ and $a_2$, respectively, due, e.g., to background subtraction on a microarray (see, in particular, Section 5.5.2 for exemplary signal detection methods using microarrays that can be used in the present invention). f is a fractional multiplicative error that relates to measurement errors due to the particular measurement methods used. For example, f can relate to sources of measurement error from hybridization assays such as those described in Section 5.5.2, below. In particular, f can be due, e.g., to hybridization non-uniformities on a microarray, fluctuations in the incorporation efficiency of a detectable label (such as fluorescent dye) in a sample, scanner gain fluctuations, etc. In particular, the skilled artisan will recognize that the quantities $\sigma_1$ and $\sigma_2$ will typically by specific to a particular experiment (for example, to a particular microarray). These quantities are therefore most preferably determined for a particular experiment from background intensity fluctuations measured from an unperturbed and perturbed state (e.g., measured on a particular microarray). By contrast, f will tend to be constant from experiment to experiment and therefore is most preferably determined from control experiments where the "perturbed" and "unperturbed" states are, in fact, the same or substantially the same states. In other words, f is preferably determined from control experiments wherein measured amounts, e.g., abundances or activities, of a plurality of cellular constituents are compared in a first, unperturbed sample to measured amounts, e.g., abundances or activities, of cellular constituents in a second unperturbed sample that is identical (or at least substantially identical) to the first sample. The probability P that this significance statistic will have a particular value X by chance alone (i.e. due to experimental noise or error) is readily determined according to Equation 31, below:

$$P=2(1-Erf(|X|))  \quad\quad\quad \text{(Equation 31)}.$$

As noted, above, the response $v_i^{(m)}$ of a particular cellular constituent i to a particular perturbation m is most preferably expressed as the logarithm (preferably the base 10 logarithm) of the ratio of the measured amounts, e.g., abundance or activity, of cellular constituent i in the perturbed state to the unperturbed state; i.e., according to Equation 32:

$$v_i^{(m)} = \log_{10}\left(\frac{a_2}{a_1}\right). \quad\quad\quad \text{(Equation 32)}$$

The uncertainty $\sigma_v$ is then readily provided by Equation 33, below.

$$\sigma_v = \frac{1}{X}\log\left(\frac{a_2}{a_1}\right) \quad\quad\quad \text{(Equation 33)}$$

Such an error model is particularly preferable because it allows weighted combining of multiple measurements of $v_i^{(m)}$. Measurements that come, e.g., from faint fluorescent spots on a microarray, will have small values of X, i.e., large errors, and will be given low weight (i.e., accorded low significance) when combining repeated measurements. Alternatively, a linear averaging of measurement intensities (e.g., hybridization intensities) on a microarray is also possible, but generally less preferable, since such averaging leads to reduced accuracy if absolute intensity calibration is uncertain from experiment to experiment (e.g. from microarray to microarray).

In a particularly preferred embodiment, a minimum-variance weighted average, given in Equation 34 below, is used to compute the mean value of $v_i^{(m)}$ for each reported cellular constituent i.

$$\bar{x} = \frac{\sum_k w_k x_k}{\sum_k w_k} \quad\quad\quad \text{(Equation 34)}$$

In Equation 34 above, $x_k$ stands for the k'th measurement of $v_i^{(m)}$ and $w_k = 1/\sigma_k^2$ wherein $\sigma_k$ is the error of the k'th measurement of $v_i^{(m)}$.

The error of $\bar{x}$ is preferably determined according to either one of two ways. In particular, the error may be computed by propagating the errors $\sigma_k$ (Equation 35 below) or, alternatively, from the scatter of the individual measurement $x_k$ (Equation 36 below).

$$\sigma^2 = \sigma_P^2 = 1\Big/\left(\sum_k w_k\right) \quad\quad\quad \text{(Equation 35)}$$

$$\sigma^2 = \sigma_s^2 = \left[(n-1)\sum_k w_k\right]^{-1}\sum_k w_k(x_k - \bar{x})^2 \quad\quad\quad \text{(Equation 36)}$$

The propagation error $\sigma_p$, given by Equation 35 above, relies totally on the error estimation of each individual experiment (e.g., for each microarray), and is therefore subject to bias or systematic uncertainties. By contrast, the scatter error $\sigma_s$, given by Equation 36 above, is an unbiased measure but has large fluctuations when the number of experimental repeats is small. Ideally, therefore, it is preferable to use the propagation error $\sigma_p$ when there is only one measurement and gradually shift to the scatter error $\sigma_s$ when the number of measurements is large. This can be readily accomplished, e.g., by using a "weighted mean of error" given by Equation 37, in which n specifies the total number of measurements.

$$\sigma_{\bar{x}} = \frac{\sigma_p + (n-1)\sigma_s}{n} \quad\quad\quad \text{(Equation 37)}$$

Although the weighted mean error given by Equation 37 does capture the increase of error observed for measurements of low intensity (i.e., cellular constituents of low abundance or activity), it can nevertheless underestimate the actual variance of individual genes due to inadequate sample size of the estimate of the scatter error $\sigma_s$. Equation 37 also ignores biological variation beyond the measurement uncertainty (e.g., when growth conditions are not perfectly well controlled so that nominally identical experiments are not perfectly identical). A more robust, gene-specific error statistic is therefore defined when large sets of control experiments are available comparing measured amounts of cellular constituent, e.g., abundances or activities, between nominally identical, unperturbed states. In such embodiments, a scale factor $\Lambda$ is computed or obtained according to Equation 38 below for each cellular constituent over all control experiments.

$$\Lambda = std(\bar{x}/\sigma_{\bar{x}}) \quad\quad\quad \text{(Equation 38)}$$

Those cellular constituents having a value of $\Lambda$ that is greater than unity have an inherent variance larger than that given by Equation 37 above. Accordingly, the errors for these cellular constituents are scaled by the factor $\Lambda$.

The significance statistic X for the weighted average can then be computed according to the equation:

$$X = \bar{x}/\sigma_{\bar{x}} \quad\quad\quad \text{(Equation 39)}$$

6. EXAMPLES

The following examples are presented by way of illustration of the previously described invention, and are not limiting of that description in any way. In particular, the examples presented hereinbelow describe the preparation of a database or compendium of three hundred full-genome expression profiles in the yeast S. cerevisiae corresponding to mutations in both characterized genes and uncharacterized open reading frames (ORFs), as well as treatments with compounds having known molecular targets. The identification of co-regulated genesets in the expression profiles is described. Moreover, profile similarities are used to assign uncharacterized genes to particular biological functions. The compendium is also used to identify a previously unknown target of a commonly used drug, dyclonine.

The results demonstrate that the expression profile of a mutant can be used as a phenotype and, further, that such usage reliably predicts phenotypes in conventional assays. The results further demonstrate that the methods of the present invention can also be used to characterize activities of small molecules and is therefore useful for characterizing drug activities.

6.1. Materials and Methods

Yeast Strains and Plasmids:

The Ssaccharomyces Genome Deletions Consortium strain background (see Winzeeler et al., 1999, *Science* 285: 901-906) was used in all experiments. In order to minimize the potential impact of unlinked recessive mutations associated with strain construction, homozygous diploid deletion mutants were profiled when possible. A complete strain table is provided in Table 1 below. All deletion mutants listed in Table 1 are start-to-stop codon deletions. Yeast strains harboring extrac chromosomes are indicated in Table 1 by two asterisks followed by the number of the duplicated or missing chromosome.

For experiments involving tet-regulatable genes, the natural promoter on the chromosome was replaced with a heptamerized tet operator fused to a kanamycin-resistance cassette enabling direct integration. The "tet activator" (i.e., tTA*, which dissociates in the presence of doxycyline) was supplied either on a CEN plasmid (Gari et al., 1997, *Yeast* 13:837-848) or integrated into the genome. Plamids expressing human ERG28 (hERG28) were constructed by PCR. Specifically, the hERG28 ORF was amplified from a mixture of human cDNA libraries and cloned by in vivo recombination in front of the yeast HOR7 promoter on pDW394 (Acacia Biosciences), a URA3-2μ high copy vector. Inserts were confirmed by sequencing. Plasmids in FIG. 11D are pRP382 and pRP383.

TABLE 1

YEAST STRAINS USED TO GENERATE EXPRESSION PROFILE COMPENDIUM

| Strain No. | Gene of Interest | Disrupted ORF | Deletions Consortium No. |
|---|---|---|---|
| R15 | afg3 (haploid) | YER017C | 148 |
| R174 | WT | WT | |
| R176 | WT | WT | |
| R276 | control strain | control strain | |
| R277 | "bub1 (haploid **2, 10)" | YGR188C | |
| R282 | bub3 (haploid **2) | YOR026W | |
| R320 | rpd3 (haploid) | YNL330C | |
| R338 | tup1 (haploid) | YCR084C | |
| R379 | sbh2 | YER019C-A | |
| R382 | rpl34a (**9) | YER056C-A | |
| R384 | yer024w | YER024W | 30156 |
| R386 | gpa2 | YER020W | 30152 |
| R394 | sap1 | YER047C | |
| R401 | his1 | YER055C | 30190 |
| R404 | yer050c | YER050C | 30185 |
| R406 | bim1 (**15) | YER016W | |
| R410 | ste4 (haploid) | YOR212W | |
| R412 | ste5 (haploid) | YDR103W | |
| R414 | ste7 (haploid) | YDL159W | |
| R416 | ste11 (haploid) | YLR362W | |
| R418 | ste12 (haploid) | YHR084W | |
| R419 | ste18 (haploid) | YJR086W | |
| R425 | tec1 (haploid) | YBR083W | |
| R426 | control strain | control strain | |
| R496 | far1 (haploid) | YJL157C | |
| R500 | fus3 (haploid) | YBL016W | |
| R538 | fpr1 | YNL135C | |
| R563 | WT | WT | |
| R592 | gal83 | YER027C | |
| R595 | yer030w | YER030W | 30162 |
| R599 | yer033c | YER033C | 30165 |
| R601 | yer034w | YER034W | 30166 |
| R604 | gln3 | YER040W | 30173 |
| R606 | yer041w | YER041W | 30174 |
| R614 | pet117 | YER058W | 30194 |
| R616 | pcl6 | YER059W | 30195 |
| R619 | cem1 | YER061C | 30198 |
| R624 | yer066c-a | YER066C-A | 30204 |
| R627 | yer067c-a | YER067C-A | 30206 |
| R630 | yer071c | YER071C | |
| R631 | nrf1 | YER072W | 30212 |
| R633 | ald5 | YER073W | 30213 |
| R651 | yer083c | YER083C | 30223 |
| R653 | yer084w | YER084W | 30224 |
| R655 | yer085c | YER085C | 30225 |
| R711 | yer044c (haploid) | YER044C | 177 |
| R777 | rnr1 (haploid **7) | YER070W | 210 |
| R842 | clb2 | YPR119W | |
| R850 | "arg5, 6" | YER069W | 30209 |
| R981 | rvs161 (haploid) | YCR009C | |
| R985 | rps24a (**9) | YER074W | 30214 |
| R987 | rps24a (haploid) | YER074W | 214 |
| R994 | bni1 (haploid) | YNL271C | |
| R1000 | cnb1 | YKL190W | |
| R1023 | swi4 | YER111C | |
| R1027 | rad6 (haploid) | YGL058W | |
| R1040 | "bub3 (**2, 8, 13)" | YOR026W | |
| R1057 | cmk2 | YOL016C | |
| R1062 | imp2' (**12) | YIL154C | |
| R1067 | mad2 | YJL030W | |
| R1082 | rad57 | YDR004W | |
| R1094 | hdf1 | YMR284W | |
| R1112 | ssn6 (haploid) | YBR112C | |
| R1122 | swi6 (haploid) | YLR182W | |
| R1135 | eca39 | YHR208W | |
| R1154 | WT | WT | |
| R1158 | control strain | control strain | |
| R1169 | bub2 | YMR055C | |
| R1184 | rtg1 | YOL067C | |
| R1186 | rgt1 | YKL038W | |
| R1187 | mbp1 | YDL056W | |
| R1190 | yap1 | YML007W | |
| R1198 | clb6 | YGR109C | |
| R1232 | hda1 | YNL021W | |
| R1237 | "cna1, cna2 (haploid)" | "YLR433C, YML057W" | |
| R1268 | ste2 (haploid) | YFL026W | |
| R1286 | whi2 | YOR043W | |
| R1307 | ras1 | YOR101W | |
| R1314 | dfr1 | YOR236W | |
| R1331 | sst2 (haploid) | YLR452C | |
| R1446 | ERG11 (tet promoter) | YGR175C | |
| R1648 | yea4 | YEL004W | |
| R1778 | pfd2 (**14) | YEL003W | 30243 |
| R1791 | yel008w | YEL008W | 30248 |
| R1792 | gcn4 | YEL009C | 30249 |
| R1794 | yel010w | YEL010W | 30250 |
| R1796 | vac8 | YEL013W | 30253 |
| R1808 | yel020c | YEL020C | 30261 |
| R1812 | rip1 | YEL024W | |
| R1815 | cup5 | YEL027W | 30268 |
| R1817 | yel028w | YEL028W | 30269 |
| R1820 | ecm10 | YEL030W | 30271 |
| R1822 | spf1 | YEL031W | 30272 |
| R1824 | yel033w | YEL033W | 30274 |
| R1826 | anp1 | YEL036C | 30277 |
| R1830 | utr4 | YEL038W | 30279 |
| R1840 | yel044w | YEL044W | 30285 |
| R1846 | yel047c | YEL047C | 30288 |
| R1850 | pau2 | YEL049W | 30290 |
| R1852 | rml2 (**13) | YEL050C | 30291 |
| R1853 | vma8 | YEL051W | 30292 |
| R1857 | mak10 | YEL053C | 30294 |
| R1859 | rpl12a | YEL054C | 30295 |
| R1860 | hat2 | YEL056W | 30297 |
| R1864 | yel059w | YEL059W | 30301 |
| R1866 | prb1 | YEL060C | 30302 |
| R1870 | npr2 | YEL062W | 30304 |
| R1878 | hpa3 | YEL066W | |
| R1885 | mnn1 | YER001W | 30322 |

TABLE 1-continued

YEAST STRAINS USED TO GENERATE EXPRESSION PROFILE COMPENDIUM

| Strain No. | Gene of Interest | Disrupted ORF | Deletions Consortium No. |
|---|---|---|---|
| R1887 | yer002w | YER002W | 30323 |
| R1891 | ynd1 | YER005W | 30326 |
| R1895 | pac2 | YER007W | 30329 |
| R1901 | yel067c | YEL067C | 30309 |
| R1905 | yel001c | YEL001C | 30241 |
| R1918 | HMG2 (tet promoter) | YLR450W | |
| R1936 | CMD1 (tet promoter) | YBR109C | |
| R1952 | ade2 (haploid) | YOR128C | |
| R1980 | yhl045w | YHL045W | 30918 |
| R1982 | ecm34 | YHL043W | 30920 |
| R1983 | yhl042w | YHL042W | 30921 |
| R1986 | cbp2 | YHL038C | 30925 |
| R1990 | sbp1 | YHL034C | 30929 |
| R1991 | rpl8a | YHL033C | 30930 |
| R1994 | ecm29 | YHL030W | 30933 |
| R1995 | yhl029c | YHL029C | 30934 |
| R2007 | yhl013c | YHL013C | 30950 |
| R2010 | yap3 | YLR120C | 30954 |
| R2012 | ste20 (**11) | YHL007C | 30956 |
| R2017 | rpl27a (**4) | YHR010W | 30973 |
| R2018 | yhr011w (**14) | YHR011W | 30974 |
| R2020 | ard1 | YHR013C | 30976 |
| R2024 | rps27b (**11) | YHR021C | 30984 |
| R2025 | yhr022c | YHR022C | 30985 |
| R2029 | yhr031c | YHR031C | 30994 |
| R2031 | yhr034c | YHR034C | 30997 |
| R2034 | kim4 | YHR038W | 31001 |
| R2035 | yhr039c | YHR039C | 31002 |
| R2038 | rrp6 | YOR001W | 31777 |
| R2042 | yor006c | YOR006C | 31782 |
| R2043 | sgt2 | YOR007C | 31783 |
| R2045 | yor009w | YOR009W | 31785 |
| R2050 | rts1 | YOR014W | 31790 |
| R2051 | yor015w | YOR015W | 31791 |
| R2052 | erp4 | YOR016C | 31792 |
| R2053 | pet127 | YOR017W | 31793 |
| R2056 | yor021c | YOR021C | 31797 |
| R2060 | hst3 | YOR025W | 31801 |
| R2063 | cin5 | YOR028C | 31804 |
| R2069 | she4 | YMR276W | 31810 |
| R2070 | pep12 | YOR036W | 31812 |
| R2071 | cyc2 | YOR037W | 31813 |
| R2072 | hir2 | YOR038C | 31814 |
| R2073 | ckb2 | YOR039W | 31815 |
| R2079 | tom6 | YOR045W | 31821 |
| R2083 | yor051c (**14) | YOR051C | 31827 |
| R2087 | ase1 (**12) | YOR058C | 31834 |
| R2089 | cka2 | YOR061W | 31837 |
| R2092 | cyt1 | YOR065W | 31841 |
| R2097 | gyp1 | YOR070C | 31846 |
| R2099 | yor072w | YOR072W | 31848 |
| R2101 | yor078w | YOR078W | 31854 |
| R2103 | yor080w (**3) | YOR080W | 31856 |
| R2108 | ost3 | YOR085W | 31861 |
| R2112 | vps21 | YOR089W | 31865 |
| R2311 | ecm1 (**3) | YAL059W | 30348 |
| R2315 | yaf1 | YAL051W | 30355 |
| R2344 | erp2 | YAL007C | 30401 |
| R2345 | yal004w | YAL004W | 30402 |
| R2347 | vps8 | YAL002W | 30405 |
| R2350 | yar014c | YAR014C | 30413 |
| R2351 | ade1 | YAR015W | 30414 |
| R2352 | kin3 | YAR018C | 30415 |
| R2359 | yar030c | YAR030C | 30423 |
| R2367 | fus2 | YMR232W | 30818 |
| R2369 | rnh1 | YMR234W | 30820 |
| R2370 | ymr237w | YMR237W | 30823 |
| R2373 | rpl20a | YMR242C | 30828 |
| R2386 | gfd1 | YMR255W | 30841 |
| R2387 | ymr244c-a | YMR256C | 30842 |
| R2388 | pet111 | YMR257C | 30843 |
| R2389 | ymr258c | YMR258C | 30844 |
| R2393 | sap30 | YMR263W | 30849 |
| R2394 | cue1 | YMR264W | 30850 |
| R2398 | ymr269w | YMR269W | 30855 |
| R2399 | scs7 | YMR272C | 30858 |
| R2400 | zds1 | YMR273C | 30859 |
| R2402 | bul1 | YMR275C | 30861 |
| R2405 | cat8 | YMR280C | 30866 |
| R2406 | aep2 | YMR282C | 30868 |
| R2409 | ymr285c | YMR285C | 30871 |
| R2410 | mrpl33 | YMR286W | 30872 |
| R2411 | msu1 | YMR287C | 30873 |
| R2415 | ymr293c | YMR293C | 30880 |
| R2416 | jnm1 | YMR294W | 30881 |
| R2428 | gas1 | YMR307W | 30897 |
| R3334 | yml034w | YML034W | 30537 |
| R3336 | yml033w | YML033W | 30539 |
| R3345 | yml018c | YML018C | 30555 |
| R3352 | yml011c | YML011C | 30563 |
| R3355 | erg6 | YML008C | 30568 |
| R3358 | yml005w | YML005W | 30571 |
| R3360 | yml003w | YML003W | 30573 |
| R3368 | ymr009w | YMR009W | 30584 |
| R3369 | ymr010w | YMR010W | 30585 |
| R3372 | ymr014w | YMR014W | 30589 |
| R3373 | erg5 | YMR015C | 30590 |
| R3377 | stb4 | YMR019W | 30594 |
| R3379 | mac1 | YMR021C | 30596 |
| R3383 | ymr025w | YMR025W | 30600 |
| R3384 | pex12 | YMR026C | 30601 |
| R3386 | ymr029c | YMR029C | 30604 |
| R3387 | ymr030w | YMR030W | 30605 |
| R3388 | ymr031w-a | YMR031W-A | 30606 |
| R3389 | ymr031c | YMR031C | 30607 |
| R3391 | ymr034c | YMR034C | 30610 |
| R3392 | imp2 | YMR035W | 30611 |
| R3396 | ymr040w | YMR040W | 30616 |
| R3397 | ymr041c | YMR041C | 30617 |
| R3398 | arg80 | YMR042W | 30618 |
| R3399 | ymr044w | YMR044W | 30620 |
| R3432 | sin3 | YOL004W | 31695 |
| R3463 | yap7 | YOL028C | 31719 |
| R3534 | rad27 | YKL113C | 31759 |
| R4039 | yil037c (haploid) | YIL037C | |
| R4044 | kss1 (haploid) | YGR040W | |
| R4048 | yil117c (haploid) | YIL117C | |
| R4060 | yjl107c (haploid) | YJL1107 | |
| R4061 | "fus3, kss1 (haploid)" | "YBL016W, YGR040W" | |
| R4063 | "dig1, dig2 (haploid)" | "YPL049C, YDR480W" | |
| R4719 | ecm18 (**7) | YDR125C | 34059 |
| R4744 | PMA1 (tet promoter) | YGL008C | |
| R4755 | swi5 | YDR146C | 34080 |
| R5034 | fre6 | YLL051C | 31539 |
| R5035 | aqy2-a | YLL052C | 31540 |
| R5036 | aqy2-b | YLL053C | 31541 |
| R5053 | ppr1 | YLR014C | 31569 |
| R5065 | ade16 | YLR028C | 31583 |
| R5295 | ymr140w | YMR140W | 30721 |
| R5296 | ymr141c | YMR141C | 30722 |
| R5299 | ymr145c | YMR145C | 30726 |
| R5300 | ymr147w | YMR147W | 30728 |
| R5311 | sap18 | YMR159C | 30742 |
| R5333 | ymr187c | YMR187C | 30772 |
| R5336 | sgs1 | YMR190C | 30775 |
| R5346 | erg2 | YMR202W | 30788 |
| R5358 | ubp8 | YMR223W | 30809 |
| R5612 | ecm31 | YBR176W | 33316 |
| R5666 | isw1 | YBR245C | 33385 |
| R5946 | eft2 | YDR385W | 34221 |
| R5955 | hpt1 | YDR399W | 34235 |
| R5965 | erd1 | YDR414C | 34250 |
| R6374 | cla1 (haploid) | YDR293C | 1146 |
| R6566 | kre1 | YNL322C | 31122 |

TABLE 1-continued

YEAST STRAINS USED TO GENERATE EXPRESSION PROFILE COMPENDIUM

| Strain No. | Gene of Interest | Disrupted ORF | Deletions Consortium No. |
|---|---|---|---|
| R6867 | ypl216w | YPL216W | 31076 |
| R6881 | rpl6b | YLR448W | 31094 |
| R7316 | sir1 | YKR101W | |
| R7318 | sir2 | YDL042C | |
| R7320 | sir3 | YLR442C | |
| R7322 | sir4 | YDR227W | |
| R7324 | pch1 | YDR440W | |
| R7326 | hog1 (haploid) | YLR113W | 2724 |
| R7345 | control strain | control strain | |
| R7347 | YEF3 (tet promoter) | YLR249W | |
| R7351 | CDC42 (tet promoter) | YLR229C | |
| R7352 | RHO1 (tet promoter) | YPR165W | |
| R7353 | FKS1 (tet promoter) | YLR342W | |
| R7356 | IDI1 (tet promoter) | YPL117C | |
| R7357 | KAR2 (tet promoter) | YJL034W | |
| R7360 | phd1 (haploid) | YKL043W | |
| R7362 | "are1, are2 (haploid)" | "YCR048W, YNR019W" | |
| R7363 | erg4 (haploid **7) | YGL012W | |
| R7364 | erg3 (haploid) | YLR056W | |
| R7365 | hes1 (haploid) | YOR237W | |
| R7377 | GCN4 | GCN4 | |
| R7474 | AUR1 (tet promoter) | YKL004W | |
| R7628 | med2 (haploid) | YDL005C | |
| R7631 | nta1 | YJR062C | |
| R7632 | ate1 | YGL017W | |
| R7633 | ubr2 | YLR024C | |
| R7634 | ubr1 | YGR184C | |
| R9359 | dig1 | YPL049C | |
| R9360 | dig2 | YDR480W | |
| R9361 | "dig1, dig2" | "YPL049C, YDR480W" | |
| R9370 | control strain | control strain | |
| R9371 | ste24 (haploid) | YJR117W | |
| R9373 | hmg1 (haploid) | YML075C | |
| R9374 | ras2 (haploid) | YNL098C | |
| R9376 | fks1 (haploid) | YLR342W | |
| R9377 | ras1 (haploid) | YOR101W | |
| R9378 | sod1 (haploid) | YJR104C | |
| R9379 | top3 (haploid) | YLR234W | |
| R9380 | top1 (haploid) | YOL006C | |
| R9381 | qcr2 (haploid) | YPR191W | |
| R9800 | dot4 | YNL186W | |
| R9864 | isw2 | YOR304W | |
| R9866 | "isw1, isw2" | "YBR245C, YOR304W" | |
| R15142 | mrt4 | YKL009W | |
| (strains listed in Table 4) | | | |
| R5502 | MRPS5 | YBR251W | 13391 |
| R5427 | MRPS5 | YBR251W | 3391 |
| R8207 | MRPL6 | YHR147C | 2841 |
| R8243 | MRPL6 | YHR147C | 12841 |
| R12260 | MRPL13 | YKR006C | 5077 |
| R12321 | MRPL13 | YKR006C | 15077 |
| R10536 | MRPL16 | YBL038W | 3064 |
| R10612 | MRPL16 | YBL038W | 13064 |
| R5110 | MRPL24 | YMR193W | 778 |
| R5181 | MRPL24 | YMR193W | 10778 |
| R11965 | MRPL31 | YKL138C | 4988 |
| R12037 | MRPL31 | YKL138C | 14988 |
| R5438 | MRPL37 | YBR268W | 3408 |
| R5513 | MRPL37 | YBR268W | 13408 |
| R11989 | MRPL38 | YKL170W | 5020 |
| R4514 | YDR115W | YDR115W | 4049 |
| R4515 | YDR115W | YDR115W | 14049 |
| R4517 | YDR116C | YDR116C | 4050 |
| R4516 | YDR116C | YDR116C | 14050 |
| R5105 | YMR188C | YMR188C | 773 |
| R5177 | YMR188C | YMR188C | 10773 |
| R13156 | YNL177C | YNL177C | 2035 |
| R13224 | YNL177C | YNL177C | 12035 |
| R7936 | YGR165W | YGR165W | 4795 |
| R8007 | YGR165W | YGR165W | 14795 |
| R6024 | YHR116W | YHR116W | 1944 |
| R6085 | YHR116W | YHR116W | 11944 |
| R10847 | YDR175C | YDR175C | 3533 |
| R10914 | YDR175C | YDR175C | 13533 |
| R3126 | YML030W | YML030W | 543 |
| R3193 | YML030W | YML030W | 10543 |
| R5080 | YMR157C | YMR157C | 739 |
| R5150 | YMR157C | YMR157C | 10739 |
| (strains listed in FIG. 11A-F) | | | |
| R174 | WT | WT | |
| R711 | yer044c (haploid) | YER044C | 177 |
| R5118 | erg2 | YMR202W | 788 |
| (strains listed in FIG. 12A-B) | | | |
| R174 | WT | | |
| R4050 | YIL117C | YIL117C | |
| R1058 | CMK2 | YOL016C | |
| R809 | YER083C | YER083C | 223 |
| R2808 | GAS1 | YMR307W | 897 |
| R1644 | ANP1 | YEL036C | 10277 |
| R1636 | SPF1 | YEL031W | 272 |
| R735 | PET117 | YER058W | |
| R3167 | MAC1 | YMR021C | 596 |
| R2131 | RPL4A | YHL033C | 930 |
| R175 | WT | | |
| (strains listed in FIG. 13A-B) | | | |
| R176 | WT | | |
| R1853 | VMA8 | YEL051W | 30292 |
| R1815 | CUP5 | YEL027W | 30268 |
| R404 | YER050C | YER050C | 30185 |
| R2018 | YHR011W | YHR011W | 30974 |
| R2415 | YMR293C | YMR293C | 30880 |
| R2411 | MSU1 | YMR287C | 30873 |
| R2406 | AEP2 | YMR282C | 30868 |
| R3392 | IMP2 | YMR035W | 30611 |
| R176 | WT | | |
| (strains listed in FIG. 14A-B) | | | |
| R176 | WT | | |
| R2020 | ARD1 | YHR013C | 30976 |
| R614 | PET117 | YER058W | 30194 |
| R1859 | RPL15B | YEL054C | 30295 |
| R1991 | RPL4A | YHL033C | 30930 |
| R2031 | YHR034C | YHR034C | 30997 |
| R2398 | YMR269W | YMR269W | 30855 |
| R1824 | YEL033W | YEL033W | 30274 |
| R2101 | YOR078W | YOR078W | 31854 |

Yeast Culture and cDNA Microarray Expression Analysis:

Experimental (mutant or chemically treated) cultures were grown, harvested and processed in parallel with corresponding wild-type or control cultures. A complete list of experimental conditions is provided, below, in Table 2.

Several colonies of similar size were picked from freshly-streaked YAPD agar plates into liquid Synthetic Complete medium (SC) with 2% glucose, grown overnight at 30° C. to mid-log phase, diluted to 0.4-1.0×10$^6$ cells/mL, and grown an addition 5-7 hours until reaching 0.4-1.0×cells/mL, at which point they were pelleted by centrifugation from 2 minutes at room temperature and frozen in liquid nitrogen. The final optical densities of experimental and control cultures were matched as closely as possible. For experiments involving treatments with chemical compounds (including doxycycline), compounds were added at the beginning of the 5-7 hour final groth phase, with equal amounts of solvent or doxycyline added to control cultures as appropriate. Total RNA was prepared by phenol:chloroform extraction followed by ethanol precipitation as described previously (see, e.g., Marton et al., 1998, *Nat. Med.* 4:1293-1301) except that the step vortexing with glass beads was replaced with a 10 minute incubation at 65° C. followed by 1 minute of vortexing. Poly-A+ RNA purification, cDNA labeling, microarray production, and microarray hybridization and washing were also done as previously described (e.g., in Marton et al., supra) with measurements taken in fluor-reversed pairs. Arrays were scanned, images were quantitated and physical artifacts such as dust and salt residue were edited as described previously (see, e.g., Marton et aL, supra). Resulting data files were evaluated by a series of quality-control criteria relating, first, to the image itself and, second, to known biological artifacts. For purposes of illustrating the impact of biases, experiments flagged as containing biological artifacts were noted by were not excluded from subsequent data analysis steps.

TABLE 2

| experiment strain | control strain | experiment sample | control sample |
|---|---|---|---|
| R2351 | R176 | ade1/ade1 | +/+ |
| R5065 | R176 | ade16/ade16 | +/+ |
| R1952 | R174 | ade2 | + |
| R2406 | R176 | aep2/aep2 | +/+ |
| R15 | R174 | afg3 | + |
| R633 | R176 | ald5/ald5 | +/+ |
| R1826 | R176 | anp1/anp1 | +/+ |
| R5035 | R176 | yll052c/yll052c | +/+ |
| R5036 | R176 | yll053c/yll053c | +/+ |
| R2020 | R176 | ard1/ard1 | +/+ |
| R7362 | R174 | are1 are2 | + |
| R850 | R176 | "arg5, 6/arg5, 6" | +/+ |
| R3398 | R176 | arg80/arg80 | +/+ |
| R2087 | R176 | ase1/ase1 | +/+ |
| R7632 | R176 | ate1/ate1 | +/+ |
| R406 | R176 | bim1/bim1 | +/+ |
| R994 | R426 | bni1 | + |
| R277 | R174 | bub1 | + |
| R1169 | R176 | bub2/bub2 | +/+ |
| R1040 | R176 | bub3/bub3 | +/+ |
| R282 | R174 | bub3 | + |
| R2402 | R176 | bul1/bul1 | +/+ |
| R2405 | R176 | cat8/cat8 | +/+ |
| R1986 | R176 | cbp2/cbp2 | +/+ |
| R619 | R176 | cem1/cem1 | +/+ |
| R2063 | R176 | cin5/cin5 | +/+ |
| R2089 | R176 | cka2/cka2 | +/+ |
| R2073 | R176 | ckb2/ckb2 | +/+ |
| R6374 | R174 | cla4 | + |
| R842 | R176 | clb2/clb2 | +/+ |
| R1198 | R176 | clb6/clb6 | +/+ |
| R1057 | R176 | cmk2/cmk2 | +/+ |
| R1237 | R174 | cna1 cna2 | + |
| R1000 | R176 | cnb1/cnb1 | +/+ |
| R2394 | R176 | cue1/cue1 | +/+ |
| R1815 | R176 | cup5/cup5 | +/+ |
| R2071 | R176 | cyc2/cyc2 | +/+ |
| R2092 | R176 | cyt1/cyt1 | +/+ |
| R1314 | R176 | dfr1/dfr1 | +/+ |
| R9359 | R176 | dig1/dig1 | +/+ |
| R9361 | R176 | dig1 dig2/dig1 dig2 | +/+ |
| R4063 | R426 | dig1 dig2 | + |
| R9360 | R176 | dig2/dig2 | +/+ |
| R9800 | R176 | dot4/dot4 | +/+ |
| R1135 | R176 | eca39/eca39 | +/+ |
| R2311 | R176 | ecm1/ecm1 | +/+ |
| R1820 | R176 | ecm10/ecm10 | +/+ |
| R4719 | R176 | ecm18/ecm18 | +/+ |
| R1994 | R176 | ecm29/ecm29 | +/+ |
| R5612 | R176 | ecm31/ecm31 | +/+ |
| R1982 | R176 | ecm34/ecm34 | +/+ |
| R5946 | R176 | eft2/eft2 | +/+ |
| R5965 | R176 | erd1/erd1 | +/+ |
| R5346 | R176 | erg2/erg2 | +/+ |
| R7364 | R174 | erg3 | + |
| R7363 | R174 | erg4 | + |
| R3373 | R176 | erg5/erg5 | +/+ |
| R3355 | R176 | erg6/erg6 | +/+ |
| R2344 | R176 | erp2/erp2 | +/+ |
| R2052 | R176 | yor016c/yor016c | +/+ |
| R496 | R426 | far1 | + |
| R9376 | R174 | fks1 | + |
| R538 | R176 | fpr1/fpr1 | +/+ |
| R5034 | R176 | fre6/fre6 | +/+ |
| R2367 | R176 | fus2/fus2 | +/+ |
| R500 | R426 | fus3 | + |
| R4061 | R426 | fus3 kss1 | + |
| R592 | R176 | gal83/gal83 | +/+ |
| R2428 | R176 | gas1/gas1 | +/+ |
| R1792 | R176 | gcn4/gcn4 | +/+ |
| R2386 | R176 | ymr255w/ymr255w | +/+ |
| R604 | R176 | gln3/gln3 | +/+ |
| R386 | R176 | gpa2/gpa2 | +/+ |
| R2097 | R176 | gyp1/gyp1 | +/+ |
| R1860 | R176 | hat2/hat2 | +/+ |
| R1232 | R176 | hda1/hda1 | +/+ |
| R1094 | R176 | hdf1/hdf1 | +/+ |
| R7365 | R174 | hes1 | + |
| R2072 | R176 | hir2/hir2 | +/+ |
| R401 | R176 | his1/his1 | +/+ |
| R9373 | R174 | hmg1 | + |
| R7326 | R174 | hog1 | + |
| R1878 | R176 | hpa3/hpa3 | +/+ |
| R5955 | R176 | hpt1/hpt1 | +/+ |
| R2060 | R176 | hst3/hst3 | +/+ |
| R3392 | R176 | imp2/imp2 | +/+ |
| R1062 | R176 | yil154c/yil154c | +/+ |
| R5666 | R176 | isw1/isw1 | +/+ |
| R9866 | R176 | "isw1/isw1, isw2/isw2" | +/+ |
| R9864 | R176 | isw2/isw2 | +/+ |
| R2416 | R176 | jnm1/jnm1 | +/+ |
| R2034 | R176 | kim4/kim4 | +/+ |
| R2352 | R176 | kin3/kin3 | +/+ |
| R6566 | R176 | kre1/kre1 | +/+ |
| R4044 | R426 | kss1 | + |
| R3379 | R176 | mac1/mac1 | +/+ |
| R1067 | R176 | mad2/mad2 | +/+ |
| R1857 | R176 | mak10/mak10 | +/+ |
| R1187 | R176 | mbp1/mbp1 | +/+ |
| R7628 | R7377 | med2 | wt |
| R1885 | R176 | mnn1/mnn1 | +/+ |
| R2410 | R176 | mrpl33/mrpl33 | +/+ |
| R15142 | R176 | mrt4/mrt4 | +/+ |
| R2411 | R176 | msu1/msu1 | +/+ |
| R1870 | R176 | npr2/npr2 | +/+ |
| R631 | R176 | nrf1/nrf1 | +/+ |
| R7631 | R176 | nta1/nta1 | +/+ |
| R2108 | R176 | ost3/ost3 | +/+ |
| R1895 | R176 | pac2/pac2 | +/+ |
| R1850 | R176 | pau2/pau2 | +/+ |
| R7324 | R176 | pch1/pch1 | +/+ |
| R616 | R176 | pcl6/pcl6 | +/+ |
| R2070 | R176 | pep12/pep12 | +/+ |
| R2388 | R176 | pet111/pet111 | +/+ |
| R614 | R176 | pet117/pet117 | +/+ |
| R2053 | R176 | pet127/pet127 | +/+ |
| R3384 | R176 | pex12/pex12 | +/+ |
| R1778 | R176 | pfd2/pfd2 | +/+ |
| R7360 | R174 | phd1 | + |
| R5053 | R176 | ppr1/ppr1 | +/+ |
| R1866 | R176 | prb1/prb1 | +/+ |
| R9381 | R174 | qcr2 | + |
| R3534 | R176 | rad27/rad27 | +/+ |
| R1082 | R176 | rad57/rad57 | +/+ |
| R1027 | R174 | rad6 | + |
| R1307 | R176 | ras1/ras1 | +/+ |
| R9377 | R174 | ras1 | + |
| R9374 | R174 | ras2 | + |
| R1186 | R176 | rgt1/rgt1 | +/+ |
| R1812 | R176 | rip1/rip1 | +/+ |

TABLE 2-continued

| experiment strain | control strain | experiment sample | control sample |
|---|---|---|---|
| R1852 | R176 | rml2/rml2 | +/+ |
| R2369 | R176 | rnh1/rnh1 | +/+ |
| R777 | R174 | rnr1 | + |
| R320 | R174 | rpd3 | + |
| R1859 | R176 | rpl15b/rpl15b | +/+ |
| R2373 | R176 | rpl20a/rpl20a | +/+ |
| R2017 | R176 | rpl27a/rpl27a | +/+ |
| R382 | R176 | rpl34a/rpl34a | +/+ |
| R6881 | R176 | rpl6b/rpl6b | +/+ |
| R1991 | R176 | rpl8a/rpl8a | +/+ |
| R985 | R176 | rps24ea/rps24ea | +/+ |
| R987 | R174 | yer074w | + |
| R2024 | R176 | rps27b/rps27b | +/+ |
| R2038 | R176 | rrp6/rrp6 | +/+ |
| R1184 | R176 | rtg1/rtg1 | +/+ |
| R2050 | R176 | rts1/rts1 | +/+ |
| R981 | R426 | rvs161 | + |
| R394 | R176 | sap1/sap1 | +/+ |
| R5311 | R176 | sap18/sap18 | +/+ |
| R2393 | R176 | ymr263w/ymr263w | +/+ |
| R379 | R176 | sbh2/sbh2 | +/+ |
| R1990 | R176 | sbp1/sbp1 | +/+ |
| R2399 | R176 | scs7/scs7 | +/+ |
| R5336 | R176 | sgs1/sgs1 | +/+ |
| R2043 | R176 | sgt2/sgt2 | +/+ |
| R2069 | R176 | yor035c/yor035c | +/+ |
| R3432 | R176 | sin3/sin3 | +/+ |
| R7316 | R176 | sir1/sir1 | +/+ |
| R7318 | R176 | sir2/sir2 | +/+ |
| R7320 | R176 | sir3/sir3 | +/+ |
| R7322 | R176 | sir4/sir4 | +/+ |
| R9378 | R174 | sod1 | + |
| R1822 | R176 | spf1/spf1 | +/+ |
| R1112 | R174 | ssn6 | + |
| R1331 | R276 | sst2 | + (bar1) |
| R3377 | R176 | stb4/stb4 | +/+ |
| R416 | R426 | ste11 | + |
| R418 | R426 | ste12 | + |
| R419 | R426 | ste18 | + |
| R1268 | R426 | ste2 | + |
| R2012 | R176 | ste20/ste20 | +/+ |
| R9371 | R9370 | afc1 | + |
| R410 | R426 | ste4 | + |
| R412 | R426 | ste5 | + |
| R414 | R426 | ste7 | + |
| R1023 | R176 | swi4/swi4 | +/+ |
| R4755 | R176 | swi5/swi5 | +/+ |
| R1122 | R174 | swi6 | + |
| R425 | R276 | tec1 | + |
| R2079 | R176 | tom6/tom6 | +/+ |
| R9380 | R174 | top1 | + |
| R9379 | R174 | top3 | + |
| R338 | R174 | tup1 | + |
| R5358 | R176 | ymr223w/ymr223w | +/+ |
| R7634 | R176 | ubr1/ubr1 | +/+ |
| R7633 | R176 | ubr2/ubr2 | +/+ |
| R1830 | R176 | utr4/utr4 | +/+ |
| R1796 | R176 | vac8/vac8 | +/+ |
| R1853 | R176 | vma8/vma8 | +/+ |
| R2112 | R176 | vps21/vps21 | +/+ |
| R2347 | R176 | vps8/vps8 | +/+ |
| R1286 | R176 | whi2/whi2 | +/+ |
| R2315 | R176 | yaf1/yaf1 | +/+ |
| R2345 | R176 | yal004w/yal004w | +/+ |
| R1190 | R176 | yap1/yap1 | +/+ |
| R2010 | R176 | yap3/yap3 | +/+ |
| R3463 | R176 | yap7/yap7 | +/+ |
| R2350 | R176 | yar014c/yar014c | +/+ |
| R2359 | R176 | yar030c/yar030c | +/+ |
| R1648 | R176 | yea4/yea4 | +/+ |
| R1905 | R176 | yel001c/yel001c | +/+ |
| R1791 | R176 | yel008w/yel008w | +/+ |
| R1794 | R176 | yel010w/yel010w | +/+ |
| R1808 | R176 | yel020c/yel020c | +/+ |
| R1817 | R176 | yel028w/yel028w | +/+ |
| R1824 | R176 | yel033w/yel033w | +/+ |
| R1840 | R176 | yel044w/yel044w | +/+ |
| R1846 | R176 | yel047c/yel047c | +/+ |
| R1864 | R176 | yel059w/yel059w | +/+ |
| R1901 | R176 | yel067c/yel067c | +/+ |
| R1887 | R176 | yer002w/yer002w | +/+ |
| R384 | R176 | yer024w/yer024w | +/+ |
| R595 | R176 | yer030w/yer030w | +/+ |
| R599 | R176 | yer033c/yer033c | +/+ |
| R601 | R176 | yer034w/yer034w | +/+ |
| R606 | R176 | yer041w/yer041w | +/+ |
| R711 | R174 | yer044c | + |
| R404 | R176 | yer050c/yer050c | +/+ |
| R624 | R176 | yer066c-a/yer066c-a | +/+ |
| R627 | R176 | yer067c-a/yer067c-a | +/+ |
| R630 | R176 | yer071c/yer071c | +/+ |
| R651 | R176 | yer083c/yer083c | +/+ |
| R653 | R176 | yer084w/yer084w | +/+ |
| R655 | R176 | yer085c/yer085c | +/+ |
| R1936 | R1936 | "tet-CMD1, 100 dox" | tet-CMD1, 0 dox |
| R2007 | R176 | yhl013c/yhl013c | +/+ |
| R1995 | R176 | yhl029c/yhl029c | +/+ |
| R1983 | R176 | yhl042w/yhl042w | +/+ |
| R1980 | R176 | yhl045w/yhl045w | +/+ |
| R2018 | R176 | yhr011w/yhr011w | +/+ |
| R2025 | R176 | yhr022c/yhr022c | +/+ |
| R2029 | R176 | yhr031c/yhr031c | +/+ |
| R2031 | R176 | yhr034c/yhr034c | +/+ |
| R2035 | R176 | yhr039c/yhr039c | +/+ |
| R4039 | R426 | yil037c | + |
| R4048 | R426 | yil117c | + |
| R4060 | R426 | yjl107c | + |
| R3360 | R176 | yml003w/yml003w | +/+ |
| R3358 | R176 | yml005w/yml005w | +/+ |
| R3352 | R176 | yml011c/yml011c | +/+ |
| R3345 | R176 | yml018c/yml018c | +/+ |
| R3336 | R176 | yml033w/yml033w | +/+ |
| R3334 | R176 | yml034w/ymlo34w | +/+ |
| R3368 | R176 | ymr009w/ymr009w | +/+ |
| R3369 | R176 | ymr010w/ymr010w | +/+ |
| R3372 | R176 | ymr014w/ymr014w | +/+ |
| R3383 | R176 | ymr025w/ymr025w | +/+ |
| R3386 | R176 | ymr029c/ymr029c | +/+ |
| R3387 | R176 | ymr030w/ymr030w | +/+ |
| R3389 | R176 | ymr031c/ymr031c | +/+ |
| R3388 | R176 | ymr031w-a/ymr031w-a | +/+ |
| R3391 | R176 | ymr034c/ymr034c | +/+ |
| R3396 | R176 | ymr040w/ymr040w | +/+ |
| R3397 | R176 | ymr041c/ymr041c | +/+ |
| R3399 | R176 | ymr044w/ymr044w | +/+ |
| R5295 | R176 | ymr140w/ymr140w | +/+ |
| R5296 | R176 | ymr141c/ymr141c | +/+ |
| R5299 | R176 | ymr145c/ymr145c | +/+ |
| R5300 | R176 | ymr147w/ymr147w | +/+ |
| R5333 | R176 | ymr187c/ymr187c | +/+ |
| R2370 | R176 | ymr237w/ymr237w | +/+ |
| R2387 | R176 | ymr244c-a/ymr244c-a | +/+ |
| R2389 | R176 | ymr258c/ymr258c | +/+ |
| R2398 | R176 | ymr269w/ymr269w | +/+ |
| R2409 | R176 | ymr285c/ymr285c | +/+ |
| R2415 | R176 | ymr293c/ymr293c | +/+ |
| R1891 | R176 | yer005w/yer005w | +/+ |
| R2042 | R176 | yor006c/yor006c | +/+ |
| R2045 | R176 | yor009w/yor009w | +/+ |
| R2051 | R176 | yor015w/yor015w | +/+ |
| R2056 | R176 | yor021c/yor021c | +/+ |
| R2083 | R176 | yor051c/yor051c | +/+ |
| R2099 | R176 | yor072w/yor072w | +/+ |
| R2101 | R176 | yor078w/yor078w | +/+ |
| R2103 | R176 | yor080w/yor080w | +/+ |
| R6867 | R176 | ypl216w/ypl216w | +/+ |
| R2400 | R176 | zds1/zds1 | +/+ |
| R7474 | R7474 | tet-AUR1 + 1.0 ug/ml Doxycycline | tet-AUR1 + 0 ug/ml Doxycycline |
| R7351 | R7345 | tet-CDC42 + 100 ug/ml Doxycycline | wt + 100 ug/ml Doxycycline |

TABLE 2-continued

| experiment strain | control strain | experiment sample | control sample |
|---|---|---|---|
| R1446 | R1158 | tet-ERG11 + 1.0 ug/ml doxycycline | control strain + 1 ug/ml doxycycline |
| R7353 | R7345 | tet-FKS1 + 400 ug/ml Doxycycline | control strain + 400 ug/ml Doxycycline |
| R1918 | R1918 | tet-HMG2 + 200 ug/ml Doxy | tet-HMG2 |
| R7356 | R7345 | IDI1 + 400 ug/ml Doxycycline | control strain + 400 ug/ml Doxycycline |
| R7357 | R7345 | tet-KAR2 + 400 ug/ml Doxycycline | control strain + 400 ug/ml Doxycycline |
| R4744 | R4744 | tet-PMA1 + 1.0 ug/ml Doxycycline | tet-PMA1 + 0 ug/ml Doxycycline |
| R7352 | R7345 | tet-RHO1 + 400 ug/ml Doxycycline | control strain + 400 ug/ml Doxycycline |
| R7347 | R7345 | tet-YEF3 + 100 ug/ml Doxycycline | wt + 100 ug/ml Doxycycline |
| R176 | R176 | 2.0 mM 2-Deoxy-D-Glucose | solvent control |
| R174 | R174 | 1000 ug/ml calcofluor white | solvent control |
| R174 | R174 | wt + .1 ug/ml cycloheximide | solvent control |
| R1158 | R1158 | tTA + 100 ug/ml Doxy | tTA + solvent |
| R174 | R174 | "wt + 350 uM FR901,228" | solvent control |
| R176 | R176 | wt + 1% glucosamine | solvent control |
| R563 | R563 | wt + 50 mM HU | solvent control |
| R174 | R174 | 50 ug/ml itraconazole | solvent control |
| R1918 | R1918 | tet-HMG2 + 43 ug/ml Lovastatin | tet-HMG2 + solvent control |
| R1154 | R1154 | 0.030% MMS | solvent control |
| R174 | R174 | 66 ug/ml nikkomycin Z | solvent control |
| R174 | R174 | 5 ug/ml terbinafine | solvent control |
| R176 | R176 | 0.002% Tunicamycin | solvent control |

Clustering and Error Model:

Clustering analysis of the perturbation response profiles was done as described, below, in Section 5.2.4. Specifically, the analysis comprised two steps. First, profiles and transcripts were selected from a data matrix and, second, experiments and responsive genes were grouped by agglomerative hierarchical clustering (see Hartigan, 1975, *Clustering Algorithms*, John Wiley & Sons, New York) where the similarity measure is the error-weighted correlation coefficient provided in Equation 11 below. Genes and experiments (i.e., columns and rows, respectively, of the data matrix) were then re-ordered according to the resulting clustering similarity trees. A statistical significance (i.e., a P-value) was also calculated for each bifurcation in the resulting cluster tree using the methods for determining statistical significance of cluster groups which are also described, below, in Section 5.2.4.

Parallel Growth Assay:

Among the 276 deletion mutants profiled, 198 corresponded to barcoded homozygous disruption strains (Shoemaker et al., 1996, *Nat. Genet.* 14:450-456). These strains were grown as part of a pool of barcoded homozygous deletion strains obtained from the Saccharomyces Genome Deletions Consortium (Winzeler et al., 1999, *Science* 285:901-906). Seven time points were taken over 20 population doublings of the pool in SC medium containing 2% glucose. The relative abundances of the different tags over 20 population doublings were determined by a two-color hybridization assay using custom-made 24,000-element oligonucleotide arrays. Growth rates for each of the strains in the pool were determined by plotting the changes in relative abundance (log ratios) versus population doublings using a linear fit model.

Sterol Profiles:

Sterols were identified using pure standards and on the basis of relative retention times. Nonsaponifiables were isolated from yeast as previously described (Molzahn and Woods, 1972, *J Gen. Microbiol.* 72:339-348). Gas chromatography (GC) analyses of the nonsaponifiable fraction were analyzed on a HP5890 series II GC equipped with the HP chemstation software. The capillary column (DB5) was 15 m×0.25 mm i.d., 0.2 μm film thickness and was programmed from 195 fC to 300 fC (195 fC for 3 min., 5.5 fC/min. to 300 fC then held for 10 min.). The linear velocity was 30 cm/s using nitrogen and the carrier gas and all injections were run in the splitless mode.

Spheroplast Lysis Rate Assay:

Spheroplast Lysis Rate was determined following methods described previously (Ovalle et al., 1998, *Yeast* 14:1159-1166). Cells were grown to nearly identical densities in mid-log phase, washed 3 times with TE and resuspended in TE at $OD_{600}$=0.6. Zymolyase 100T (dissolved in 50% glycerol) was added to 5 μg/mL and $OD_{600}$ was measured every 3-7 minutes for one hour. Rate Index is determined as Lag Time/Maximum Lysis Rate, where the Lag Time is the time in which the $OD_{600}$ decreased by 0.05 and the Maximum Lysis Rate is the absolute value of the slope of the least-squares fit line for the portion of the lysis curve (six or more points) with the steepest log-linear decline as defined previously (Ovalle et al., supra).

$^{35}$S-Methionine Incorporation Rate Assay:

Yeast strains were grown in synthetic complete medium lacking methionine and cysteine. Cells were grown in 40 mL liquid culture at 30° C. to an $A_{600}$ of 0.5 to 0.7. At zero time, methionine and cysteine were added at 50 μM concentrations along with 1 μCi/mL of [$^{35}$S] labeled pro-mix (Amersham Pharmacia Biotech). Duplicate aliquots of 1 mL were removed from each culture at 20 min. intervals for up to 2 hours. Cell densities were monitored at one hour intervals. All samples were precipitated with 200 μL of 50% ice cold TCA (trichloroacetic acid) for 10 minutes on ice, heated at 90° C. for 15 minutes, chilled on ice for 10 minutes, filtered through GF/C filters, washed with 15 mL of 2.5% ice cold TCA followed by 10 mL of cold 95% ethanol, dried and counted in a scintillation counter with 3.5 mL of the scintillant (Bio-Safe II from RPI). Labelled methionine/cysteine incorporation into proteins were calculated based on the total amount of TCA precipitable counts.

6.2. Generation of a Compendium of Response Profiles for Yeast Deletion Mutants Using a two-color cDNA microarray hybridization assay (see, Schena et al., 1995, *Science* 270:467-470), three hundred expression profiles were generated in *S. cerevisiae* in which transcript levels of a mutant or compound-treated culture were compared to that of a wild-type or mock-treated culture. 276 deletion mutants, 11 tetracycline-regulatable alleles of essential genes (Gari et al., 1997, *Yeast* 13:837-848) and 13 well-characterized compounds were profile. Deletion mutants were selected such that a variety of functional classifications were represented, as shown in FIG. 9A. Sixty-nine of the 276 deletions were of uncharacterized open reading frames (ORFs). To allow direct comparison of the behavior of all genes in response to all mutations and treatments, experiments were performed under a single condition: cells were grown at 30° C. in liquid synthetic complete SC) medium plus 2% glucose to mid-log phase, with the final optical densities of the experimental and control cultures closely matched (see Section 6.1 above). Because any one growth condition is unlikely to elicit a phenotype from every mutant, one possible outcome of this approach was that many mutants would not display transcriptional alterations. However, in actuality nearly all of the experiments resulted in a two-fold or greater alteration in the abundance of at least one transcript, not including the deleted gene (see the first column of Table 3, below).

To ensure that observed transcriptional alterations were caused by the mutations or treatments and not by random fluctuations or systematic biases, experiments were also conducted to investigate whether the abundance of some transcripts might inherently fluctuate more than others under the culture conditions used (Wittes and Friedman, 1999, *J. Natl. Cancer Inst.* 91:400-401). In parallel with the 300 experiment data set, a series of 63 negative control experiments were conducted in which simultaneously grown untreated isogenic wild-type cultures were compared to each other. The vast majority of profiles from these negative control experiments also included at least one gene with greater than 2-fold induction or repression (see the first column of Table 3, below). Two-dimensional (2D) clustering analysis (see, e.g., Hartigan, 1975, *Clustering Algorithms*, John Wiley & Sons, New York; Eisen et al., 1993, *Mol. Gen. Genet.* 241:447-456; and Section 5.2.4, supra) of these control experiments revealed several sets of genes, many of which are known to be regulated by nutrition or stress, that displayed small-magnitude but coordinate differences in transcript abundance between two seemingly identical cultures (see FIG. 10A). The genes with highest variance in these sixty-three control experiments are also among those that fluctuate the most in the 300 compendium experiments (see FIG. 10B).

These fluctuations were taken to represent a composite of experimental and biological "noise." Indeed, application of an error model that accounts for measurement quality (such as the error model described, below, in Section 5.2.4) improves correlations between 151 repeated experiments in the 300-experiment data set, as can be seen in FIGS. 10C and 10D. Further improvement was attained using the gene specific error model described in Section 5.2.4 above. This error model reduces the significance of genes in proportion to their fluctuation in the negative control experiments (see, FIG. 10E). Thus, although both noise and systematic biases can impact a measured biological expression profile, including a perturbation response profile, their effects on reproducibility can be minimized by accounting for measurement error and reducing the statistical weight of genes that have large inherent fluctuations in abundance.

After applying the gene-specific error model, nearly 90% of deletion mutants with a growth rate that is less than 90% that of wild-type still displayed profiles with more than five genes significant at $P \leq 0.01$, a stringent definition of profile significance as it is fulfilled by none of the 63 negative control experiments (see the fifth column of Table 3, above). However, among mutants with growth rates more similar to wild-type, the error model has a striking effect on the proportion of profiles at this levels of significance (compare, in particular, column 1 to columns 2-7 of Table 3, above). Only 28% of deletion mutants with growth >95% that of wild-type displayed profiles with more than five genes significant at $P \leq 0.01$, using the gene-specific error model. Among these, deletion of a previously characterized (i.e., "named") gene had a much higher likelihood of resulting in such a significant profile (43%) than deletion of an uncharacterized ORF (8%). This surprising difference was not accounted for by biases in ORF length, basal transcription, growth rate or sequence redundancy. Remaining explanations include functional redundancy, or that the uncharacterized ORFs are required only for very specific processes or to survive particular conditions.

Overall, more than half (172/300) of the experiments resulted in a profile with more than five genes significant at $P \leq 0.01$ (see, in particular, the fifth column of Table 3 above). Further, approximately 75% of all transcripts (4553) were significantly up- or down-regulated at $P \leq 0.01$ in at least one profile. Thus, a single growth protocol was sufficient to generate functional data for roughly half of the mutants and to evoke responses from a large majority of genes.

6.3. Hierarchical Clustering of Response Profile and Genesets

Analysis of the 300-experiment compendium data set was performed to determine whether groups of known or expected co-regulated genes were easily detectable, and whether mutations or treatments known to impact similar cellular processes displayed similar expression profiles. Two-dimensional hierarchical clustering of the most prominent gene behaviors among the experiments with the larges profiles illustrates the gross trnaxcriptional features of the 300 expression profiles (see FIG. 9B), identifying groups of co-regulated transcripts (horizontal axis) as well as groups of experiments with similar profiles (vertical axis). Several large classes of co-regulated genes are apparent. Prominent groups whose activation

TABLE 3

| No. Experiments: | >1 gene w/>2-fold induction | Error Model Accouting for Quality of Measurements | | | Error Model Accounting for Gene-Specific Fluctuations | | |
|---|---|---|---|---|---|---|---|
| | | >5 genes (P < 0.01) | >20 genes (P < 0.01) | >100 genes (P < 0.01) | >5 genes (P < 0.01) | >20 genes (P < 0.01) | >100 genes (P < 0.01) |
| Compendium Experiments (300 Total) | 288 (96%) | 219 (73%) | 170 (57%) | 94 (31%) | 172 (57%) | 122 (41%) | 60 (20%) |
| Barcoded Deletion Mutants (198 Total) | 189 (95%) | 136 (69%) | 100 (51%) | 51 (26%) | 97 (49%) | 68 (34%) | 28 (14%) |
| w/growth <90% WT (50 mutants) | 50 (100%) | 50 (100%) | 45 (90%) | 32 (64%) | 45 (90%) | 35 (70%) | 22 (44%) |
| w/growth 90-95% WT (26 mutants) | 26 (100%) | 24 (92%) | 20 (77%) | 6 (23%) | 17 (65%) | 11 (42%) | 2 (8%) |
| w/growth >95% WT (122 mutants) | 113 (93%) | 62 (51%) | 35 (29%) | 13 (11%) | 35 (29%) | 22 (18%) | 4 (3%) |
| named (72) | 69 (96%) | 48 (67%) | 29 (40%) | 12 (17%) | 31 (43%) | 20 (28%) | 4 (6%) |
| unamed (50) | 44 (88%) | 14 (28%) | 6 (12%) | 1 (2%) | 4 (8%) | 2 (4%) | 0 (0%) |
| Control Experiments (63 Total) | 55 (87%) | 11 (17%) | 2 (3%) | 0 (0%) | 0 (0%) | 0 (0%) | 0 (0%) | or repression is restricted to specific classes of mutants correspond to proteins involved in mating (see Roberts et al., 2000, *Science* 287:873-880), ergosterol biosynthesis and mitochondrial respiration (see Section 6.4, below). Others, such as the PKC/calcineurin activated gene cluster (Marton et al., 1998, *Nat. Med.* 4:1293-1301; Roberts et al., supra) are induced in several types of experiments. The known DNA-damage/S-phase arrest inducible RNR2, RNR3 and RNR4 transcripts are also closely co-regulated, and are induced almost exclusively by HU, MMS, mr1Δ, tup1Δ and ssn6Δ, as expected from previous studies (Zhou and Elledge, 1992, *Genetics* 131:851-866). A large group of transcripts, including HIS5, ARG4, LEU4 and many others associated with amino-acid biosynthesis appear in the largest number of profiles, but because these transcripts also tend to fluctuate in negative control experiments, the error model described above reduces their significance relative to other genes.

In general, different mutants that affect the same cellular process display related transcript profile, whether the mutation affects a protein involved directly in transcription or some other cellular process. In most cases, the global profile similarity is sufficient to cause association in the clustering analysis, resulting in discernable experiment clusters that correspond to mutants known to share phenotypes. For example, as expected, deletion of either component of the Tup1-Ssn6 co-repressor (Williams et al., 1991, *Mol. Cell. Biol.* 11:3307-3316; Keleher et al., 1992, *Cell* 68:709-719; DeRisi et al., 1997, *Science* 278:680-686) results in a very large and very similar profile (illustrated in FIG. 9B by the horizontal red stripe denoted "tup1, ssn6"). Deletion mutants in CUP5 or VMA8, both of which encode components of the vacuolar $H^+$-ATPase complex (Eide et al., 1993, *Mol. Gen. Genet.* 241:447-456; Nelson et al., 1995, *Proc. Natl. Acad. Sci. U.S.A.* 92:497-501), also share a virtually identical transcript profile (see FIGS. 9B and 9C; for comparison, an example of an uncorrelated response is shown in FIG. 9D). Other clusters of profiles that are dominated by deletion mutants known to have similar functional consequences include the groups of mitochondrial respiration-, mating-, and sterol pathway-related experiments, which are easily visualized in FIG. 9B because the induce large-magnitude changes in specific groups of transcripts. A number of less visible groups of profiles likewise correspond to established functional classes. For example, discrete clusters are formed by mutations in genes encoding silencing factors Sir2p and Sir3p, chromatin-remodeling proteins Isw1p and Isw2p, histone deacetylase components Rpd3p and Sin3p, ribosomal proteins, and proteins involved in cell wall function (FIG. 9B). Similarly, treatment of cells with an inhibitory compound mimics loss of function of its target in many cases. For example, treatment with lovastatin, which inhibits HMG-CoA reductase (Alberts et al., 1980, *Proc. Natl. Acad. Sci. U.S.A.* 77:3957-3961) results in a transcript profile that correlates highly with the profile produced by reducing expression of HMG2 (see FIG. 9E). Additional examples, also shown in FIG. 9B in which profiles caused by inhibitory compounds resemble those of mutants in the affected pathway include itroconzaole/erg/11 (Daum et al., 1998, *Yeast* 14:1471-1510), cycloheximide/yef3, hydroxyurea/rnr1, tunicamycin/glucosamine/2-deoxy-D-glucose/gas1, and FR901, 228/rpd3 (Nakajima et al., 1998, *Exp. Cell. Res.* 241:126-133).

To determine whether the experiment clusters described above correspond to those with the highest statistical significance, the bootstrap method described in Section 5.2.4, above, was used to obtain P-values for each of the branch points in the experiment cluster tree shown in FIG. 9B. The significance assigned to a branch point is dependent on the number of elements in the branches. Thus, the P-values of large clusters tend to be more significant than those of smaller clusters, and P-values of branches of different sizes may not be directly comparable. Nonetheless, among the fifteen clusters of greater than four experiments and $P \leq 0.01$, 11 of 15 correspond to the groups of mutants discussed above. The remaining four clusters are composed largely of profiles from functionally unrelated mutants in which the predominant transcriptional changes are the same as those that drive clustering in the control experiments (labeled "AA" and "S/C" in FIGS. 9B and 10B for "Amino Acid Biosynthesis" and "Stress/Carbohydrate Metabolism," respectively). The presence of these four clusters is consistent with the fact that the gene-specific error model described above does not eliminate these frequently-occurring biases but, rather, reduces their statistical significance. Such potentially misleading experiment clusters can be readily identified by the groups of genes induced or repressed or, alternatively, by the fact that their composition makes little or no biological sense. The data presented herein demonstrate, however, that on the whole, most large and statistically significant clusters correspond to biologically related groups of genes and experiments.

6.4. Identification of Cellular Functions of Uncharacterized Open Reading Frames The juxtaposition of functionally related mutants on the profile index of the clustering analysis in FIG. 9B supports the idea that a compendium of profiles could serve as a systematic tool for identification of gene functions since mutants that display similar expression profiles are likely to share cellular functions. The fact that treatment with pharmacological compounds elicits a response mimicking that of mutation of the target demonstrates that pathways affected by uncharacterized compounds can also be determined by such methods.

The experiments described in this section demonstrate that cellular functions of uncharacterized ORFs of *S. cerevisiae* can indeed be predicted by comparing the expression profile of the corresponding deletion mutant to profiles of known mutants in the compendium. The experiments also demonstrate that an unknown drug target can be identified according to the same techniques. In particular, the experiments described herein demonstrate the characterization of previously uncharacterized yeast ORFs that are involved in cell wall maintenance, mitochondrial respiration and protein synthesis, all of which are well-defined pathways and established targets of antifungal and/or antimicrobila compounds.

6.4.1. YER044c (ERG28) Encodes a Protein Involved in Ergosterol Biosynthesis The yeast ergosterol biosynthesis pathway is of particular interest as it is the target of numerous antifungal compounds and shares many features with human cholesterol biosynthesis (Daum et al., 1998, *Yeast* 14:1471-1510). Because inhibition of the pathway results in transcriptional induction of many of the genes encoding pathway enzymes (Damn et al., supra), study of sterol biosynthesis in yeast should represent an ideal opportunity to identify novel factors by expression profiling. Indeed, mutants and treatments affecting sterol biosynthesis display a characteristic transcript profile, causing these profile to cluster together. This profile includes several hundred expression changes that can be dissected into at least five major transcript clusters (FIG. 11A) and appears to reflect the fact that disrupting sterol homeostatsis compromises membrane function, resulting in impaired tryptophan uptake, sensitivity to cations and decreased mating frequency (Parks et al., 1995, *Lipids* 30:227-230). One of these transcript clusters (labeled 'ergosterol' in FIG. 11A) is induced specifically by ergosterol-related experiments, and corresponds primarily to the ergosterol biosynthetic genes. In particular, 7 of the 19 genes in this cluster encode known components of the ergosterol biosynthetic pathway.

Clustered among the profiles from sterol pathway mutants erg2Δ, erg3Δ and tet-ERG11 is the profile caused by deletion of the uncharacterized ORF YER044c (FIG. 11A). Because this ORF clusters with members of the ergosterol biosynthetic pathway, the ORF YER044c is also referred to herein as ERG28.

Consistent with the hypothesis that ERG28 is involved in sterol biosynthesis, the ERG28 transcript is itself co-regulated with the ergosterol-specific transcript cluster (FIG. 10A). To assess the biological significance of these observations, and erg28Δ strain was analyzed in detail. Although ERG28 is not essential, the erg28Δ cells grew slowly (approximately 70% of the wild-type growth rate) as shown in FIG. 11D (see also Smith et al., 1996, *Science* 274:2069-2074; Winzeler et al., 1999, *Science* 285:901-906). Gas chromatography (GC) analysis revealed that erg28Δ cells contain an unusual sterol profile in that additional sterols accumulate that are not seen in the wild type strain, implicating the involvement of the ERG28 gene product in ergosterol biosynthesis (FIG. 11C). The erg28Δ cells accumulate significantly less ergosterol (approx. 50%) than wild type cells, but still in sufficient quantity to support growth (FIG. 11C). This result explains why erg28Δ cells are not resistant to nystatin, a compound that binds ergosterol and has been used extensively to screen for mutants late in the ergosterol biosynthesis pathway (Molzahn and Woods, 1972, *J. Gen. Microbiol.* 72:339-348; Bard et al., 1972, *J. Bacteriol.* 111:649-657). Therefore, ERG28 encodes a novel gene product involved in sterol biosynthesis that could not have been identified by the typical primary screen for ergosterol-related mutants.

During the course of these experiments, a human homolog of ERG28 (referred to herein as hERG28) was identified (Veitia et al., 1999, *Cytogenet. Cell Genet.* 85:217-220). However, the function of this gene was not determined. The hypothesis that hERG28 functions in sterol biosynthesis was therefore tested by determining whether hERG28 could complement the yeast erg28Δ deletion mutant. To this end, the hERG28 open reading frame was PCR amplified and cloned in front of the yeast HOR7 promoter on a 2μ plasmid (see Section 6.1, above). hERG28 restored wild-type growth to an erg28Δ mutant (FIG. 11D), showing that the gene is functionally conserved. hERG28 is therefore potentially a novel component of the human cholesterol biosynthetic pathway.

6.4.2. Dyclonine Inhibits a Yeast Homolog of the Sigma Receptor

In an effort to identify unknown drug targets using the compendium, a number of expression profiles were generated by treating yeast with uncharacterized drugs (i.e., drugs without known targets). Among these, treatment with the commonly-used topical anaesthetic dyclonine resulted in an expression profile that most closely resembled profiles resulting from perturbation of the ergosterol pathway (correlation with the erg24 profile is shown in FIG. 11E). GC analysis confirmed that the sterol content of dyclonine-treated cells was abnormal (FIG. 11F, center), and featured a buildup of fecosterol, indicating inhibition of Erg2p, the sterol C-8 isomerase (FIG. 11F, right).

The human gene with the greatest sequence similarity to the yeast Erg2 protein is not the human sterol isomerase, but rather the sigma receptor (Hanner et al., 1996, *Proc. Natl. Acad. Sci. U.S.A.* 93:8072-8077; Kekuda et al., 1996, *Biochem. Biophys. Res. Commun.* 229:553-558). The sigma receptor is a neurosteroid-interacting protein that positively regulates potassium conductance (Nguyen et aL, 1998, *Eur. J. Pharmacol.* 361:157-163; Wilke et al., 1999, *J. Physiol.* (Lond.) 517:391-406) and binds a number of neuroactive drugs, including haloperidol and cocaine (both anaesthetics). Several inhibitory compounds target both the yeast Erg2 protein and the mammalian sigma receptor. For example, the known Erg2 inhibitor fenpropimorph binds the sigma receptor (Moebius et al., 1997, *Br. J. Pharmacol* 121:1-6), and haloperidol binds and inhibits the yeast Erg2 enzyme (Moebius et al., 1996, *Biochemistry* 35:16871-16878). Thus, a novel mechanism for the anaesthetic property of dyclonine is that it binds the sigma receptor and inhibits nerve conductance by reducing potassium current.

6.4.3. YER083c is Involved in Yeast Cell Wall Function

Unlike the profiles resulting from perturbation of ergosterol biosynthesis, which feature a group of ergosterol-specific transcript inductions, no transcripts could be identified that were induced only by mutants involved in cell wall function (FIGS. 9B and 11A). Nonetheless, the pattern of combined inductions and repressions was sufficiently unique to cause profiles from cell wall related mutants gas1Δ, spf1Δ, and amp1Δ to form a discrete cluster together with tunicamycin, glucosamine, and 2-deoxy-D-glucose treatments, all of which impact cell wall function (FIG. 11A). Grouped together with these cell wall related profiles is that of yer083cΔ, suggesting that YER083c is required for normal cell wall function. Indeed, yer083cΔ has additional properties characteristic of cell wall mutants: yer083cΔ mutants grow slowly (~80% of wild-type growth rate) (Smith et al., 1996, *Science* 274:2069-2074; Winzeler et al., 1999, *Science* 285: 901-906), and are hypersensitive to calcofluor white (FIG. 12A), a compound frequently used to identify cell wall-related mutants because it binds chitin and interferes with cell wall function (Roncero et al., 1988, *J. Bacteriol.* 170:1950-1954; Ram et al., 1994, *Yeast* 10:1019-1030; Lussier et al., 1997, *Genetics* 147:435-450). Furthermore, yer083cΔ cells suffer an increased spheroplast lysis rate (FIG. 12B), also indicating alterations in the cell wall (Lipke et al., 1976, *J Bacteriol.* 127:610-618; Ovalle et al., 1998, *Yeast* 14:1159-1166). Thus, YER083c is required for proper cell wall function. The fact that the function of this gene was identified based solely on the composite expression pattern of many genes shows that discovery of novel gene functions via the compendium is independent of pathway-specific reporters. In addition, because the regulation of the YER083c transcript itself does not suggest involvement in cell wall function, this example shows that identifying a gene's function using the compendium does not require any information on the transcriptional regulation of the gene in question.

6.4.4. Identification of New Proteins Required for Mitochondrial Respiration The compendium analysis described herein further demonstrates that transcript profiles can yield more specific information regarding the molecular consequences of a perturbation. In particular, defects in mitochondrial respiration are known to be associated with at least two types of nuclear mutations in yeast: those that directly compromise mitochondrial function, and those that are primarily involved in iron regulation, which is in turn required for mitochondrial function (Raguzzi et al., 1988, *FEBS Lett.* 231:253-258; Eide et al., 1993, *Mol. Gen. Genet.* 241:447-456). The data presented herein shows that the established physiological difference between these two classes of respiratory mutations is mirrored by the expression profile. Specifically, two distinct clusters arise from the profiles of respiratory-deficient mutants: a larger group corresponding to mutations in mitochondrial components, and a smaller group composed of deletions mutants in MAC1, VMA8 and CUP5, all required for iron metabolism (FIGS. 9B and 13A) (Raguzzi et al., supra; Eide et al., supra; Jungmann et al., 1993, *EMBO J.* 12:5051-5056; Szczypka et al., 1997, *Yeast* 13:1423-1435). The two branches are distinct at P≦0.001. The major difference between the two groups of profiles is that while all respiratory mutants specifically induce a category of transcripts including iron-homeostatic regulators and a set of major facilitator super-family genes (FIG. 13A), only the larger cluster of profiles corresponding to mutations in mitochondrial components features up-regulation of a set of transcripts that includes several genes encoding citric acid cycle enzymes (FIG. 13A). This shows that gross phenotypes (in this example, respiratory deficiency) can be sub-classified by the expression profile into groups that reflect the source of the defect.

To further confirm this sub-classification capability, laboratory phenotypes of novel mutants were investigated to determine whether these phenotypes followed classifications assigned by the profile clustering tree. Expression profiles displayed by uncharacterized ORF deletions yhr011wΔ, yer05cΔ, and ymr293cΔ are interleaved in the profile cluster tree with those of deletions of mitochondrial components (FIGS. 9B and 13A), suggesting that these mutants should be unable to grow on nonfermentable carbon sources such as glycerol. The specific pattern of transcript inductions, including the set encompassing citric acid-cycle genes, furthermore leads to the prediction that they are not primarily involved in iron regulation and thus will not display the calcium- (Ohya et al., 1991, *J. Biol. Chem.* 266:13971-13977) or iron- sensitivity phenotypes exhibited by the vma8Δ and cup5Δ mutants. Both of these predictions were confirmed (FIG. 13B), verifying the predictive capacity of sub-classifications on the profile clustering tree. Further consistent with a role in mitochondrial function, these genes all have close homologs in bacteria: Yer050cp is similar to bacterial ribosomal subunit S18, Yhr011wp is similar to bacterial seryl-tRNA synthases, and Ymr293cp is similar to bacterial glutamyl-tRNA amidotransferases.

Although none of the transcripts of these three new respiratory-related genes (YHR011, YER050c, YMR293c) is strongly regulated in the compendium data set presented herein (none of them is up- or down-regulated more than two-fold in any of the 300 experiments), a search for transcripts most closely regulated with each of them revealed that they are all co-regulated with numerous components of the mitochondrial ribosome. In fact, at least 37 components of the mitochondrial ribosome are members of a previously undescribed group of approximately 114 genes that are co-regulated over all 300 experiments. The overwhelming majority of these regulations are less than 2-fold.

Nearly two-thirds of the genes in this group (67/114) have known mitochondrial functions. The majority of the others (41/46) are uncharacterized ORFs. These uncharacterized ORFs might, therefore, also be required for mitochondrial function, providing an opportunity to test the efficacy of determining gene functions by transcript co-regulations. Deletion mutants in eight of the mitochondrial ribosome components in this gene cluster all resulted in respiratory deficiency, based on their inability to grow with glycerol as the sole carbon source (Table 4, below). Among the uncharacterized ORFs were five genes with similarity to prokaryotic and/or chloroplast ribosomal proteins. Deletion mutants in four of these ORFs were tested and were likewise respiratory-deficient, suggesting that they are previously unidentified components of the mitochondrial ribosome (Table 4). Among five randomly-selected uncharacterized ORFS in this group, however, deletion mutants in only three were respiratory-deficient (Table 4). This shows that coordinated transcriptional regulations can be used to enrich for novel genes with a given phenotype, but that there is potential for false positives. This example also suggests that the size and quality of the data set improve detection of such co-regulations. Because of the low magnitude of the changes involved, this co-regulated group of genes would have been difficult or impossible to detect without the benefit of a substantial collection of profiles.

TABLE 4

| Deleted Gene | Growth on glycerol | Sequence homologs |
| --- | --- | --- |
| MRPS5 | − | prokaryotic ribosomal protein S5 |
| MRPL6 | − | prokaryotic ribosomal protein L6 |
| MRPL13 | − | prokaryotic ribosomal protein L13 |
| MRPL16 | − | prokaryotic ribosomal protein L16 |
| MRPL24 | − | prokaryotic ribosomal protein L24 |
| MRPL31 | − | prokaryotic ribosomal protein L31 |
| MRPL37 | − | prokaryotic ribosomal protein L37 |
| MRPL38 | − | prokaryotic ribosomal protein L38 |
| YDR115W | − | prokaryotic ribosomal protein L34 |
| YDR116C | +/− (sick) | prokaryotic ribosomal protein L1 |
| YMR188C | − | prokaryotic ribosomal protein S17 |
| YNL177C | − | *T. maritima* ribosomal protein L22 |
| YGR165W | − | — |
| YHR116W | − | — |
| YDR175C | − | — |
| YML030W | + | — |
| YMR157C | + | — |

6.4.5. Identification of new Gene Products Involved in Protein Synthesis

The unexpected identification of physiologically relevant but very low-magnitude transcriptional regulation of the mitochondrial ribosome suggests that low-amplitude but meaningful regulatory patterns may be common and, further, that such patterns may be sufficient to cause correlations among related experiments. To test this hypothesis, data from the yeast compendium was further analyzed to determine whether similarity between experiments driven by such low-magnitude changes could be biologically significant. Ribosome subunit deletions provide an exemplary test case for examining this hypothesis. Although profiles from a number of ribosome subunit deletions from a discrete cluster, only a handful of genes (fewer than 10) are significantly up-regulated or down-regulated more than three-fold in any of these profiles (see FIG. 9B). In fact, the profile associations do not rely on these outliers, because the association of all these experiments is retained in the profile clustering tree even when all regulations greater than 1.5-fold are masked from the 300-experiment data structure. Furthermore, when such small regulations are used as the basis of clustering analysis, this profile cluster gains additional translation-related experiments that are otherwise exclude, such as tet-YEF3 and cycloheximide treatment. These results show that low-magnitude expression changes can indeed be used to group profiles from related mutants.

Like the cell wall and mitochondrial respiration profile clusters described above, the translation related cluster includes mutants with deletions in uncharacterized ORFs (specifically, yor078wΔ, ymr269Δ and yhr034cΔ) together with known ribosome subunit deletions rps24aΔ, rp127aΔ, rp18aΔ and rp112Δ. The cluster also includes a partial deletion of translation elongation factor 5A (encoded by YEL034w) produced by deletion of the overlapping ORF YEL033w. Although the comprehensive biochemical analyses to which ribosomes have been subject (Link et al., 1999, Nat. Biotecdhnol. 17:676-682) make it seem unlikely that the products of these uncharacterized ORFs are ribosomal proteins, each of these knew mutants has both a reduced growth rate and a reduced protein synthesis rate, similar to ribosome subunit deletion strains. Other slow-growth mutants tested do not have reduced protein synthesis rates (shown in FIG. 14B). YOR078w, YMR269w and YBRO34c could conceivably encode previously unidentified ribosome assembly or stability factors, translational regulatory factors or nucleolar proteins. The analysis shows that even low-magnitude expression patterns can be used to discover the cellular functions of novel genes.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for characterizing a cellular constituent as being associated or not being associated with a biological function, said method comprises on a suitably programmed computer identifying one or more response profiles associated with a known biological function as either correlating or not correlating with a response profile for the cellular constituent being characterized, wherein:
    (a) each of said one or more response profiles associated with said known biological function comprises changes of a plurality of cellular constituents in a biological sample in which a particular cellular constituent, other than the cellular constituent being characterized, that is associated with said known biological function is perturbed,
    (b) said response profile for the cellular constituent being characterized comprises changes of measured amounts of a plurality of cellular constituents in a biological sample in which the cellular constituent being characterized is perturbed, and
    (c) either the cellular constituent being characterized is characterized as being associated with said known biological function if said response profile for said cellular constituent being characterized correlates with said response profile associated with said known biological function, or the cellular constituent being characterized is characterized as not being associated with said known biological function if said response profile for said cellular constituent being characterized does not correlate with said response profile associated with said known biological function, and wherein the one or more response profiles associated with a known biological function that correlate with the response profile for the cellular constituent being characterized are identified by a method which comprises:

clustering a plurality of response profiles so that response profiles that are correlated are located within a particular cluster; and identifying response profiles that cluster with the response profile for the cellular constituent being characterized.

2. The method of claim 1 wherein the cellular constituent being characterized is a gene or gene product.

3. The method of claim 2 wherein the perturbation to the cellular constituent being characterized comprises a mutation of said gene.

4. The method of claim 2 wherein the perturbation to the cellular constituent being characterized comprises modifying abundances of mRNA transcripts of said gene.

5. The method of claim 4 wherein abundances of mRNA transcripts are modified by antisense nucleic acids.

6. The method of claim 4 wherein abundances of mRNA transcripts are modified by ribozymes.

7. The method of claim 2 wherein the perturbation to the cellular constituent being characterized comprises modifying abundances or activities of said gene product.

8. The method of claim 7 wherein abundances or activities of said gene product are modified by antibodies.

9. The method of claim 1 wherein a particular cellular constituent associated with a known biological function is a gene or gene product associated with said known biological function.

10. The method of claim 9 wherein the perturbation to said gene or gene product associated with said known biological function comprises a mutation of said gene associated with said known biological function.

11. The method of claim 9 wherein the perturbation to said gene or gene product associated with said known biological function comprises modifying abundances of mRNA transcripts of said gene associated with said known biological function.

12. The method of claim 11 wherein abundances of mRNA transcripts are modified by antisense nucleic acids.

13. The method of claim 11 wherein abundances of mRNA transcripts are modified by ribozymes.

14. The method of claim 9 wherein the perturbation to the gene or gene product associated with said known biological function comprises modifying abundances or activities of said gene product associated with said known biological function.

15. The method of claim 14 wherein abundances or activities of said gene product associated with said known biological function are modified by antibodies.

16. The method of claim 1 wherein said changes of measured amounts of a plurality of cellular constituents in a biological sample comprise changes in abundances of mRNA species in said biological sample.

17. The method of claim 16 wherein abundances of mRNA species in said biological sample are provided by a method comprising:
    (a) reverse transcribing mRNA species extracted from cells to form cDNA species; and
    (b) measuring abundances of said cDNA species.

18. The method of claim 16 wherein abundances of mRNA species in said biological sample are provided by a method comprising:
(a) reverse transcribing mRNA species extracted from cells to form cDNA species;
(b) transcribing said cDNA species to form cRNA species; and
(c) measuring abundances of said cRNA species.

19. The method of claim 16 wherein abundances of mRNA species in said biological sample are provided by a method which comprises measuring abundances of polynucleotide species on a microarray, said microarray comprising
(a) a surface, and
(b) binding sites for a plurality of polynucleotide species attached to said surface
wherein said binding sites are attached to said surface such that the identity of a binding site can be determined from its position on the surface.

20. The method of claim 1 wherein said changes of measured amounts of a plurality of cellular constituents in a biological sample comprise changes in protein abundances in said biological sample.

21. The method of claim 1 wherein said plurality of response profiles is clustered by means of an agglomerative hierarchical clustering algorithm.

22. The method of claim 1, wherein said one or more response profiles associated with said known biological function that either correlates or does not correlate with said response profile for the cellular constituent being characterized is a consensus profile associated with said known biological function.

23. The method of claim 1, wherein the clustering a plurality of response profiles so that response profiles that are correlated are located within a particular cluster comprises clustering a plurality of response profiles so that response profiles that are correlated are located within a hyperspherical cluster distribution.

24. A method for characterizing a cellular constituent as being associated or not associated with a particular biological function, in which said method comprises:
on a suitably programmed computer:
(a) clustering a plurality of response profiles, wherein each response profile in said plurality of response profiles comprises changes in measured amounts of a plurality of cellular constituents in a biological sample in which a particular cellular constituent is perturbed or modified, and
said plurality of response profiles includes a response profile for the cellular constituent being characterized, said response profile for the cellular constituent being characterized comprising changes in measured amounts of a plurality of cellular constituents expressed in a biological sample in which the cellular constituent being characterized is perturbed or modified; and
(b) identifying one or more response profiles in said plurality of response profiles that cluster with the response profiles for the cellular constituent being characterized, said identified response profiles being associated with a known biological function, or identifying one or more response profiles in said plurality of response profiles that do not cluster with the response profiles for the cellular constituent being characterized, said identified response profiles being associated with a known biological function,
wherein if said response profile associated with the cellular constituent being characterized is identified as clustering with said response profiles being associated with a known biological function, said cellular constituent is characterized as being associated with said known biological function, and if said response profile associated with the cellular constituent being characterized is identified as not clustering with said response profiles being associated with a known biological function, said cellular constituent is characterized as not being associated with said known biological function.

25. The method of claim 24, wherein the cellular constituent being characterized is a gene or gene product.

26. The method of claim 25 wherein the perturbation to the cellular constituent being characterized comprises a mutation of said gene.

27. The method of claim 25 wherein the perturbation to the cellular constituent being characterized comprises modifying abundances of mRNA transcripts of said gene.

28. The method of claim 27 wherein said abundances of mRNA transcripts are modified by antisense nucleic acids.

29. The method of claim 27 wherein said abundances of mRNA transcripts are modified by ribozymes.

30. The method of claim 24 wherein said changes of measured amounts of a plurality of cellular constituents in a biological sample comprise changes in abundances of mRNA species in said biological sample.

31. The method of claim 30 wherein said changes in abundances of a plurality of mRNA species in said biological sample are provided by a method comprising:
(a) reverse transcribing mRNA species extracted from cells to form cDNA species; and
(b) measuring abundances of said cDNA species.

32. The method of claim 30 wherein said changes in abundances of mRNA species in said biological sample are provided by a method comprising:
(a) reverse transcribing mRNA species extracted from cells to form cDNA species;
(b) transcribing said cDNA species to form cRNA species; and
(c) measuring abundances of said cRNA species.

33. The method of claim 30 wherein abundances of mRNA species in said biological sample are provided by a method which comprises measuring abundances of polynucleotide species on a microarray, said microarray comprising:
(a) a surface; and
(b) binding sites for a plurality of polynucleotide species attached to said surface,
wherein said binding sites are attached to said surface such that the identity of a binding site can be determined from its position on the surface.

34. The method of claim 24, wherein said one or more response profiles associated with a known biological function that either cluster or do not cluster with said response profile for said cellular constituent being characterized is a consensus profile associated with said known biological function.

35. The method of claim 24, wherein the clustering a plurality of response profiles comprises clustering a plurality of response profiles so that response profiles are located within a hyperspherical cluster distribution.

36. A computer system for characterizing cellular constituents, said computer system comprising:
one or more processor units; and
one or more memory units connected to said one or more processor units,
said one or more memory units containing one or more programs which cause said one or more processor units to execute steps of:

(a) receiving a data structure for a response profile of a cellular constituent to be characterized, said response profile of a cellular constituent to be characterized comprising changes of measured amounts of a plurality of cellular constituents in a biological sample in which the cellular constituent to be characterized is perturbed; and (b) identifying one or more response profiles associated with a known biological function that correlate or do not correlate with said response profile of the cellular constituent to be characterized, wherein each of the one or more response profiles associated with said known biological function comprises changes of a plurality of cellular constituents in a biological sample in which a particular cellular constituent, other than the cellular constituent to be characterized, that is associated with said known biological function is perturbed, wherein if said response profile of the cellular constituent to be characterized correlates with said one or more response profiles associated with a known biological function, the cellular constituent to be characterized is characterized as being associated with said known biological function, and if said response profile of the cellular constituent to be characterized does not correlate with said one or more response profiles associated with a known biological function, the cellular constituent to be characterized is characterized as not being associated with said known biological function, and wherein said programs further cause the one or more processor units to execute steps of:

clustering a plurality of response profiles so that response profiles that are correlated are located within a particular cluster; and identifying response profiles that cluster with the response profile for the cellular constituent to be characterized.

37. The computer system of claim 36 wherein said programs cause the one or more processor units to execute said step of clustering by means of an agglomerative hierarchical clustering algorithm.

38. The method of claim 36, wherein the clustering a plurality of response profiles so that response profiles that are correlated are located within a particular cluster comprises clustering a plurality of response profiles so that response profiles that are correlated are located within a hyperspherical cluster distribution.

39. A computer program product not consisting of a signal for use in conjunction with a computer having one or more memory units and one or more processor units, the computer program product comprising a computer readable storage medium having a computer program mechanism encoded thereon, wherein said computer program mechanism can be loaded into the one or more memory units of a computer and cause the one or more processor units of the computer to execute steps of:

(a) receiving a data structure for a response profile of a cellular constituent to be characterized, said response profile of a cellular constituent to be characterized comprising changes of measured amounts of a plurality of cellular constituents in a biological sample in which the cellular constituent to be characterized is perturbed; and (b) identifying one or more response profiles associated with a known biological function that correlate with said response profile of the cellular constituent to be characterized, wherein each of the one or more response profiles associated with said known biological function comprises changes of a plurality of cellular constituents in a biological sample in which a particular cellular constituent, other than the cellular constituent to be characterized, that is associated with said known biological function is perturbed, and wherein said computer program mechanism can further cause the one or more processor units to execute steps of:

clustering a plurality of response profiles so that response profiles that are correlated are located within a particular cluster; and identifying response profiles that cluster with the response profile for the cellular constituent to be characterized.

40. The computer program product of claim 39 wherein said computer program mechanism causes the one or more processor units to execute said step of clustering by means of an agglomerative hierarchical clustering algorithm.

41. The method of claim 39, wherein the clustering a plurality of response profiles so that response profiles that are correlated are located within a particular cluster comprises clustering a plurality of response profiles so that response profiles that are correlated are located within a hyperspherical cluster distribution.

* * * * *